US009138318B2

(12) United States Patent
Yao et al.

(10) Patent No.: US 9,138,318 B2
(45) Date of Patent: Sep. 22, 2015

(54) APPARATUS FOR FORMING AN IMPLANT

(75) Inventors: Jian Q. Yao, Austin, TX (US); Ben Walthall, Austin, TX (US); Jizong Gao, Cedar Park, TX (US); Victor Zaporojan, Austin, TX (US)

(73) Assignee: Zimmer, Inc., Warsaw, IN (US)

( * ) Notice: Subject to any disclaimer, the term of this patent is extended or adjusted under 35 U.S.C. 154(b) by 0 days.

(21) Appl. No.: 13/327,265

(22) Filed: Dec. 15, 2011

(65) Prior Publication Data

US 2012/0107384 A1 May 3, 2012

Related U.S. Application Data

(63) Continuation of application No. 12/101,553, filed on Apr. 11, 2008.

(60) Provisional application No. 60/911,429, filed on Apr. 12, 2007.

(51) Int. Cl.
*A61F 2/02* (2006.01)
*A61F 2/30* (2006.01)
(Continued)

(52) U.S. Cl.
CPC ......... *A61F 2/30756* (2013.01); *A61L 27/3604* (2013.01); *A61L 27/38* (2013.01); *A61L 27/3817* (2013.01); *A61L 27/54* (2013.01); *A61F 2/3094* (2013.01); *A61F 2/3859* (2013.01);
(Continued)

(58) Field of Classification Search
CPC . A61F 2/30756; A61F 2/30957; A61L 27/38; A61L 27/3604

USPC ............ 623/11.11, 23.1, 20.16, 23.51, 23.56, 623/23.58; 264/313, 314, 316; 424/548
See application file for complete search history.

(56) References Cited

U.S. PATENT DOCUMENTS

| 1,347,622 A | 7/1920 | Deininger |
| 2,533,004 A | 12/1950 | Ferry et al. |

(Continued)

FOREIGN PATENT DOCUMENTS

| AU | 2006282754 A2 | 3/2007 |
| AU | 2008240191 B2 | 1/2014 |

(Continued)

OTHER PUBLICATIONS

Langer, F. and Gross, A.E., Immunogenicity of Allograft Articular Cartilage, JBJS, 1974, pp. 297-304, vol. 56-A, No. 2.

(Continued)

*Primary Examiner* — Gregory Anderson
*Assistant Examiner* — Christina Lauer
(74) *Attorney, Agent, or Firm* — Schwegman Lundberg & Woessner, P.A.

(57) ABSTRACT

Implants for repairing tissue defects, such as cartilage tissue defects, and methods of their preparation and use are disclosed. A mold of a tissue defect is prepared by pressing upon the defect a substrate having shape memory, such as aluminum foil. The mold, which has contours substantially conforming to those of the defect, is removed from the defect, and tissue particles are added to the mold ex vivo. A biological carrier such as biocompatible glue is also added to the mold. The combination of tissue particles and the biological carrier thereby form an implant, which retains its shape after separation from the mold. The implant can be transferred to the tissue defect, with contours of the mold matching corresponding contours of the defect.

20 Claims, 4 Drawing Sheets

(51) Int. Cl.
*A61L 27/36* (2006.01)
*A61L 27/38* (2006.01)
*A61L 27/54* (2006.01)
*A61F 2/38* (2006.01)
*A61F 2/28* (2006.01)
*A61F 2/46* (2006.01)

(52) U.S. Cl.
CPC ............... *A61F2002/2817* (2013.01); *A61F 2002/30764* (2013.01); *A61F 2002/30957* (2013.01); *A61F 2002/30971* (2013.01); *A61F 2002/4635* (2013.01); *A61F 2310/00365* (2013.01); *A61L 2300/25* (2013.01); *A61L 2300/414* (2013.01); *A61L 2300/64* (2013.01)

(56) References Cited

U.S. PATENT DOCUMENTS

| | | |
|---|---|---|
| 2,621,145 A | 12/1952 | Sano |
| 3,302,289 A * | 2/1967 | Spaulding ............... 433/214 |
| 3,400,199 A | 9/1968 | Balassa |
| 3,474,146 A | 10/1969 | Balassa |
| 3,476,855 A | 11/1969 | Balassa |
| 3,478,146 A | 11/1969 | Balassa |
| 3,772,432 A | 11/1973 | Balassal |
| RE28,093 E | 7/1974 | Balassa |
| 3,966,908 A | 6/1976 | Balassa |
| 4,440,680 A | 4/1984 | Cioca |
| 4,453,939 A | 6/1984 | Zimmerman et al. |
| 4,479,271 A | 10/1984 | Bolesky et al. |
| 4,522,096 A | 6/1985 | Niven, Jr. |
| 4,566,138 A | 1/1986 | Lewis et al. |
| 4,587,766 A | 5/1986 | Miyatake et al. |
| 4,609,551 A | 9/1986 | Caplan et al. |
| 4,627,879 A | 12/1986 | Rose et al. |
| 4,640,834 A | 2/1987 | Eibl et al. |
| 4,641,651 A | 2/1987 | Card |
| 4,642,120 A | 2/1987 | Nevo et al. |
| 4,656,137 A | 4/1987 | Balassa |
| 4,660,755 A | 4/1987 | Farling |
| 4,714,457 A | 12/1987 | Alterbaum |
| 4,773,418 A | 9/1988 | Hettich |
| 4,818,633 A * | 4/1989 | Dinwoodie et al. .......... 428/614 |
| 4,846,835 A | 7/1989 | Grande |
| 4,851,354 A | 7/1989 | Winston et al. |
| 4,863,474 A | 9/1989 | Brown et al. |
| 4,863,475 A | 9/1989 | Andersen et al. |
| 4,904,259 A | 2/1990 | Itay |
| 4,911,720 A | 3/1990 | Collier |
| 4,928,603 A | 5/1990 | Rose et al. |
| 4,952,403 A | 8/1990 | Vallee et al. |
| 4,963,489 A | 10/1990 | Naughton et al. |
| 4,997,444 A | 3/1991 | Farling |
| 4,997,445 A | 3/1991 | Hodorek |
| 5,002,071 A | 3/1991 | Harrell |
| 5,002,582 A | 3/1991 | Guire et al. |
| 5,013,324 A | 5/1991 | Zolman et al. |
| 5,018,285 A | 5/1991 | Zolman et al. |
| 5,030,215 A | 7/1991 | Morse et al. |
| 5,032,508 A | 7/1991 | Naughton et al. |
| 5,041,138 A | 8/1991 | Vacanti et al. |
| 5,053,050 A | 10/1991 | Itay |
| 5,067,963 A | 11/1991 | Khouri et al. |
| 5,067,964 A | 11/1991 | Richmond et al. |
| 5,069,881 A | 12/1991 | Clarkin |
| 5,080,674 A | 1/1992 | Jacobs et al. |
| 5,092,887 A | 3/1992 | Gendler |
| 5,130,418 A | 7/1992 | Thompson |
| 5,139,527 A | 8/1992 | Redl et al. |
| 5,189,148 A | 2/1993 | Akiyama et al. |
| 5,198,308 A | 3/1993 | Shetty et al. |
| 5,206,023 A | 4/1993 | Hunziker |
| 5,217,954 A | 6/1993 | Foster et al. |
| 5,219,363 A | 6/1993 | Crowninshield et al. |
| 5,226,914 A | 7/1993 | Caplan et al. |
| 5,236,457 A | 8/1993 | Devanathan |
| 5,254,471 A | 10/1993 | Mori et al. |
| 5,269,785 A | 12/1993 | Bonutti |
| 5,270,300 A | 12/1993 | Hunziker |
| 5,281,422 A | 1/1994 | Badylak et al. |
| 5,282,861 A | 2/1994 | Kaplan |
| 5,290,552 A | 3/1994 | Sierra et al. |
| 5,290,558 A | 3/1994 | O'Leary et al. |
| 5,312,417 A | 5/1994 | Wilk |
| 5,323,954 A | 6/1994 | Shetty et al. |
| 5,326,357 A | 7/1994 | Kandel |
| 5,345,927 A | 9/1994 | Bonutti |
| 5,356,629 A | 10/1994 | Sander et al. |
| 5,368,858 A | 11/1994 | Hunziker |
| 5,372,821 A | 12/1994 | Badylak et al. |
| 5,387,243 A | 2/1995 | Devanathan |
| 5,403,317 A | 4/1995 | Bonutti |
| 5,405,607 A | 4/1995 | Epstein |
| 5,410,016 A | 4/1995 | Hubbell et al. |
| 5,443,454 A | 8/1995 | Tanabe et al. |
| 5,443,510 A | 8/1995 | Shetty et al. |
| 5,443,512 A | 8/1995 | Parr et al. |
| 5,445,833 A | 8/1995 | Badylak et al. |
| 5,456,723 A | 10/1995 | Steinemann et al. |
| 5,456,828 A | 10/1995 | Tersi et al. |
| 5,461,953 A | 10/1995 | Mccormick |
| 5,475,052 A | 12/1995 | Rhee et al. |
| 5,482,929 A | 1/1996 | Fukunaga et al. |
| 5,496,375 A | 3/1996 | Sisk et al. |
| 5,504,300 A | 4/1996 | Devanathan et al. |
| 5,510,396 A | 4/1996 | Prewett et al. |
| 5,514,536 A | 5/1996 | Taylor |
| 5,516,532 A | 5/1996 | Atala et al. |
| 5,516,533 A | 5/1996 | Badylak et al. |
| 5,535,810 A | 7/1996 | Compton et al. |
| 5,545,222 A | 8/1996 | Bonutti |
| 5,549,704 A | 8/1996 | Sutter |
| 5,549,904 A | 8/1996 | Juergensen et al. |
| 5,554,389 A | 9/1996 | Badylak et al. |
| 5,556,429 A | 9/1996 | Felt |
| 5,565,519 A | 10/1996 | Rhee et al. |
| 5,571,187 A | 11/1996 | Devanathan |
| 5,577,517 A | 11/1996 | Bonutti |
| 5,578,492 A | 11/1996 | Fedun |
| 5,585,007 A | 12/1996 | Antanavich et al. |
| 5,605,887 A | 2/1997 | Pines et al. |
| 5,612,028 A | 3/1997 | Sackier et al. |
| 5,618,925 A | 4/1997 | Dupont et al. |
| 5,624,463 A | 4/1997 | Stone et al. |
| 5,639,280 A | 6/1997 | Warner et al. |
| 5,643,192 A | 7/1997 | Hirsh et al. |
| 5,650,494 A | 7/1997 | Cerletti et al. |
| 5,654,166 A | 8/1997 | Kurth |
| 5,655,546 A | 8/1997 | Halpern |
| 5,656,587 A | 8/1997 | Sporn et al. |
| 5,662,710 A | 9/1997 | Bonutti |
| 5,669,544 A | 9/1997 | Schulze et al. |
| 5,672,284 A | 9/1997 | Devanathan et al. |
| 5,673,840 A | 10/1997 | Schulze et al. |
| 5,673,841 A | 10/1997 | Schulze et al. |
| 5,680,982 A | 10/1997 | Schulze et al. |
| 5,681,353 A | 10/1997 | Li et al. |
| 5,692,668 A | 12/1997 | Schulze et al. |
| 5,694,951 A | 12/1997 | Bonutti |
| 5,695,998 A | 12/1997 | Badylak et al. |
| 5,709,854 A | 1/1998 | Griffith-Cima et al. |
| 5,713,374 A | 2/1998 | Pachence et al. |
| 5,714,371 A | 2/1998 | Ramanathan et al. |
| 5,723,010 A | 3/1998 | Yui et al. |
| 5,723,011 A | 3/1998 | Devanathan et al. |
| 5,723,331 A | 3/1998 | Tubo et al. |
| 5,734,959 A | 3/1998 | Krebs et al. |
| 5,735,875 A | 4/1998 | Bonutti et al. |
| 5,736,132 A | 4/1998 | Juergensen et al. |
| 5,736,396 A | 4/1998 | Bruder et al. |
| 5,749,968 A | 5/1998 | Melanson et al. |
| 5,753,485 A | 5/1998 | Dwulet et al. |
| 5,755,791 A | 5/1998 | Whitson et al. |
| 5,769,899 A | 6/1998 | Schwartz et al. |

(56) References Cited

U.S. PATENT DOCUMENTS

| | | |
|---|---|---|
| 5,770,194 A | 6/1998 | Edwardson et al. |
| 5,782,835 A | 7/1998 | Hart et al. |
| 5,782,915 A | 7/1998 | Stone |
| 5,786,217 A | 7/1998 | Tubo et al. |
| 5,788,662 A | 8/1998 | Antanavich et al. |
| 5,795,571 A | 8/1998 | Cederholm-Williams et al. |
| 5,795,780 A | 8/1998 | Cederholm-Williams et al. |
| 5,811,094 A | 9/1998 | Caplan et al. |
| 5,824,093 A | 10/1998 | Ray et al. |
| 5,826,776 A | 10/1998 | Schulze et al. |
| 5,827,217 A | 10/1998 | Silver et al. |
| 5,830,741 A | 11/1998 | Dwulet et al. |
| 5,842,477 A | 12/1998 | Naughton et al. |
| 5,853,746 A | 12/1998 | Hunziker |
| 5,853,976 A | 12/1998 | Hesse et al. |
| 5,864,016 A | 1/1999 | Eibl et al. |
| 5,866,415 A | 2/1999 | Villeneuve |
| 5,866,630 A | 2/1999 | Mitra et al. |
| 5,876,208 A | 3/1999 | Mitra et al. |
| 5,876,451 A | 3/1999 | Yui et al. |
| 5,876,452 A | 3/1999 | Athanasiou et al. |
| 5,879,398 A | 3/1999 | Swarts et al. |
| 5,888,219 A | 3/1999 | Bonutti |
| 5,888,491 A | 3/1999 | Mitra et al. |
| 5,890,898 A | 4/1999 | Wada et al. |
| 5,891,455 A | 4/1999 | Sittinger et al. |
| 5,899,936 A | 5/1999 | Goldstein |
| 5,902,741 A | 5/1999 | Purchio et al. |
| 5,919,702 A | 7/1999 | Purchio et al. |
| 5,921,987 A | 7/1999 | Stone |
| 5,922,027 A | 7/1999 | Stone |
| 5,922,846 A | 7/1999 | Cerletti et al. |
| 5,926,685 A | 7/1999 | Krebs et al. |
| 5,928,945 A | 7/1999 | Seliktar et al. |
| 5,935,131 A | 8/1999 | Bonutti |
| 5,944,754 A | 8/1999 | Vacanti |
| 5,944,755 A | 8/1999 | Stone |
| 5,948,384 A | 9/1999 | Filler |
| 5,952,215 A | 9/1999 | Dwulet et al. |
| 5,962,405 A | 10/1999 | Seelich |
| 5,964,752 A | 10/1999 | Stone |
| 5,964,805 A | 10/1999 | Stone |
| 5,968,556 A | 10/1999 | Atala et al. |
| 5,985,315 A | 11/1999 | Patat et al. |
| 5,989,269 A | 11/1999 | Vibe-Hansen et al. |
| 5,989,888 A | 11/1999 | Dwulet et al. |
| 6,022,361 A | 2/2000 | Epstein et al. |
| 6,025,334 A | 2/2000 | Dupont et al. |
| 6,041,723 A | 3/2000 | Peterson |
| 6,045,990 A | 4/2000 | Baust et al. |
| 6,048,966 A | 4/2000 | Edwardson et al. |
| 6,051,249 A | 4/2000 | Samuelsen |
| 6,059,198 A | 5/2000 | Moroi et al. |
| 6,060,053 A | 5/2000 | Atala |
| 6,077,989 A | 6/2000 | Kandel et al. |
| 6,080,194 A | 6/2000 | Pachence et al. |
| 6,080,579 A | 6/2000 | Hanley, Jr. et al. |
| 6,083,383 A | 7/2000 | Huang et al. |
| 6,087,553 A | 7/2000 | Cohen et al. |
| 6,107,085 A | 8/2000 | Coughlin et al. |
| 6,110,209 A | 8/2000 | Stone |
| 6,110,210 A | 8/2000 | Norton et al. |
| 6,110,212 A | 8/2000 | Gregory |
| 6,110,482 A | 8/2000 | Khouri et al. |
| 6,120,514 A | 9/2000 | Vibe-Hansen et al. |
| 6,129,761 A | 10/2000 | Hubbell |
| 6,132,465 A | 10/2000 | Ray et al. |
| 6,132,472 A | 10/2000 | Bonutti |
| 6,140,123 A | 10/2000 | Demetriou et al. |
| 6,140,452 A | 10/2000 | Felt et al. |
| 6,143,214 A | 11/2000 | Barlow |
| 6,150,163 A | 11/2000 | McPherson et al. |
| 6,152,142 A | 11/2000 | Tseng |
| 6,162,241 A | 12/2000 | Coury et al. |
| 6,171,610 B1 | 1/2001 | Vacanti et al. |
| 6,174,313 B1 | 1/2001 | Bonutti |
| 6,179,871 B1 | 1/2001 | Halpern |
| 6,183,737 B1 | 2/2001 | Zaleske et al. |
| 6,187,329 B1 | 2/2001 | Agrawal et al. |
| 6,197,575 B1 | 3/2001 | Griffith et al. |
| 6,200,330 B1 | 3/2001 | Benderev et al. |
| 6,203,526 B1 | 3/2001 | McBeth et al. |
| 6,224,893 B1 | 5/2001 | Langer et al. |
| 6,235,316 B1 | 5/2001 | Adkisson |
| 6,242,247 B1 | 6/2001 | Rieser et al. |
| 6,248,114 B1 | 6/2001 | Ysebaert |
| 6,264,659 B1 | 7/2001 | Ross et al. |
| 6,271,320 B1 | 8/2001 | Keller et al. |
| 6,274,090 B1 | 8/2001 | Coelho et al. |
| 6,280,993 B1 | 8/2001 | Yamato et al. |
| 6,294,656 B1 | 9/2001 | Mittl et al. |
| 6,306,169 B1 | 10/2001 | Lee et al. |
| 6,306,177 B1 | 10/2001 | Felt et al. |
| 6,312,668 B2 | 11/2001 | Mitra et al. |
| 6,322,563 B1 | 11/2001 | Cummings et al. |
| 6,327,257 B1 | 12/2001 | Khalifa |
| 6,336,930 B1 | 1/2002 | Stalcup et al. |
| 6,338,878 B1 | 1/2002 | Overton et al. |
| 6,358,266 B1 | 3/2002 | Bonutti |
| 6,361,565 B1 | 3/2002 | Bonutti |
| 6,368,298 B1 | 4/2002 | Beretta et al. |
| 6,368,784 B1 | 4/2002 | Murray |
| 6,370,920 B1 | 4/2002 | Overton et al. |
| 6,378,527 B1 | 4/2002 | Hungerford et al. |
| 6,395,327 B1 | 5/2002 | Shetty |
| 6,417,320 B1 | 7/2002 | Otto et al. |
| 6,423,063 B1 | 7/2002 | Bonutti |
| 6,425,704 B2 | 7/2002 | Voiers et al. |
| 6,436,143 B1 | 8/2002 | Ross et al. |
| 6,437,018 B1 | 8/2002 | Gertzman et al. |
| 6,443,988 B2 | 9/2002 | Felt et al. |
| 6,444,228 B1 | 9/2002 | Baugh et al. |
| 6,447,514 B1 | 9/2002 | Stalcup et al. |
| 6,464,713 B2 | 10/2002 | Bonutti |
| 6,468,289 B1 | 10/2002 | Bonutti |
| 6,468,527 B2 | 10/2002 | Austin et al. |
| 6,472,162 B1 | 10/2002 | Coelho et al. |
| 6,475,764 B1 | 11/2002 | Burtscher et al. |
| 6,482,235 B1 | 11/2002 | Lambrecht et al. |
| 6,485,723 B1 | 11/2002 | Badylak et al. |
| 6,492,163 B1 | 12/2002 | Yoo et al. |
| 6,497,903 B1 | 12/2002 | Hennink et al. |
| 6,503,267 B2 | 1/2003 | Bonutti et al. |
| 6,503,277 B2 | 1/2003 | Bonutti |
| 6,504,079 B2 | 1/2003 | Tucker et al. |
| 6,511,958 B1 | 1/2003 | Atkinson et al. |
| 6,514,514 B1 | 2/2003 | Atkinson et al. |
| 6,514,522 B2 | 2/2003 | Domb |
| 6,528,052 B1 | 3/2003 | Smith et al. |
| 6,533,817 B1 | 3/2003 | Norton et al. |
| 6,534,084 B1 | 3/2003 | Vyakarnam et al. |
| 6,534,591 B2 | 3/2003 | Rhee et al. |
| 6,543,455 B2 | 4/2003 | Bonutti |
| 6,544,472 B1 | 4/2003 | Compton et al. |
| 6,551,355 B1 | 4/2003 | Lewandrowski et al. |
| 6,559,119 B1 | 5/2003 | Burgess et al. |
| 6,575,982 B1 | 6/2003 | Bonutti |
| 6,576,265 B1 | 6/2003 | Spievack |
| 6,579,538 B1 | 6/2003 | Spievack |
| 6,582,960 B1 | 6/2003 | Martin et al. |
| 6,592,531 B2 | 7/2003 | Bonutti |
| 6,596,180 B2 | 7/2003 | Baugh et al. |
| 6,599,515 B1 | 7/2003 | Delmotte |
| 6,607,534 B2 | 8/2003 | Bonutti |
| 6,610,033 B1 | 8/2003 | Melanson et al. |
| 6,620,169 B1 | 9/2003 | Peterson et al. |
| 6,626,859 B2 | 9/2003 | Von Segesser |
| 6,626,945 B2 | 9/2003 | Simon et al. |
| 6,626,950 B2 | 9/2003 | Brown et al. |
| 6,630,000 B1 | 10/2003 | Bonutti |
| 6,632,246 B1 | 10/2003 | Simon et al. |
| 6,632,648 B1 | 10/2003 | Kampinga et al. |
| 6,637,437 B1 | 10/2003 | Hungerford et al. |
| 6,638,309 B2 | 10/2003 | Bonutti |

(56) References Cited

U.S. PATENT DOCUMENTS

| | | |
|---|---|---|
| 6,645,316 B1 | 11/2003 | Brouwer et al. |
| 6,645,764 B1 | 11/2003 | Adkisson |
| 6,649,168 B2 | 11/2003 | Arvinte et al. |
| 6,652,532 B2 | 11/2003 | Bonutti |
| 6,652,872 B2 | 11/2003 | Nevo et al. |
| 6,652,883 B2 | 11/2003 | Goupil et al. |
| 6,653,062 B1 | 11/2003 | DePablo et al. |
| 6,662,805 B2 | 12/2003 | Frondoza et al. |
| 6,663,616 B1 | 12/2003 | Roth et al. |
| 6,676,971 B2 | 1/2004 | Goupil et al. |
| 6,685,987 B2 | 2/2004 | Shetty |
| 6,697,143 B2 | 2/2004 | Freeman |
| 6,705,790 B2 | 3/2004 | Quintero et al. |
| 6,713,772 B2 | 3/2004 | Goodman et al. |
| 6,719,803 B2 | 4/2004 | Bonutti |
| 6,719,901 B2 | 4/2004 | Dolecek et al. |
| 6,730,299 B1 | 5/2004 | Tayot et al. |
| 6,733,515 B1 | 5/2004 | Edwards et al. |
| 6,736,853 B2 | 5/2004 | Bonutti |
| 6,737,072 B1 | 5/2004 | Angele et al. |
| 6,740,186 B2 | 5/2004 | Hawkins et al. |
| 6,743,232 B2 | 6/2004 | Overaker et al. |
| 6,773,458 B1 | 8/2004 | Brauker et al. |
| 6,773,713 B2 | 8/2004 | Bonassar et al. |
| 6,776,938 B2 | 8/2004 | Bonutti |
| 6,797,006 B2 | 9/2004 | Hodorek |
| 6,800,663 B2 | 10/2004 | Asgarzadeh et al. |
| 6,818,008 B1 | 11/2004 | Cates et al. |
| 6,830,762 B2 | 12/2004 | Baugh et al. |
| 6,833,408 B2 | 12/2004 | Sehl et al. |
| 6,835,198 B2 | 12/2004 | Bonutti |
| 6,835,277 B2 | 12/2004 | Park |
| 6,840,960 B2 | 1/2005 | Bubb |
| 6,852,330 B2 | 2/2005 | Bowman et al. |
| 6,860,904 B2 | 3/2005 | Bonutti |
| 6,884,428 B2 | 4/2005 | Binette et al. |
| 6,886,568 B2 | 5/2005 | Frondoza et al. |
| 6,893,466 B2 | 5/2005 | Trieu |
| 6,905,517 B2 | 6/2005 | Bonutti |
| 6,919,067 B2 | 7/2005 | Filler et al. |
| 6,919,172 B2 | 7/2005 | DePablo et al. |
| 6,921,633 B2 | 7/2005 | Baust et al. |
| 6,942,880 B1 | 9/2005 | Dolecek |
| 6,949,252 B2 | 9/2005 | Mizuno et al. |
| 6,965,014 B1 | 11/2005 | Delmotte et al. |
| 6,979,307 B2 | 12/2005 | Beretta et al. |
| 6,990,982 B1 | 1/2006 | Bonutti |
| 6,991,652 B2 | 1/2006 | Burg |
| 7,009,039 B2 | 3/2006 | Yayon et al. |
| 7,045,601 B2 | 5/2006 | Metzner et al. |
| 7,067,123 B2 | 6/2006 | Gomes et al. |
| 7,081,125 B2 | 7/2006 | Edwards et al. |
| 7,083,964 B2 | 8/2006 | Kurfurst et al. |
| 7,087,227 B2 | 8/2006 | Adkisson |
| RE39,321 E | 10/2006 | MacPhee et al. |
| 7,134,437 B2 | 11/2006 | Bonutti |
| 7,147,471 B2 | 12/2006 | Frey et al. |
| 7,217,294 B2 | 5/2007 | Kusanagi et al. |
| 7,235,255 B2 | 6/2007 | Austin et al. |
| 7,273,756 B2 | 9/2007 | Adkisson et al. |
| 7,276,235 B2 | 10/2007 | Metzner et al. |
| 7,276,481 B2 | 10/2007 | Golembo et al. |
| 7,299,805 B2 | 11/2007 | Bonutti |
| 7,316,822 B2 | 1/2008 | Binette et al. |
| 7,375,077 B2 | 5/2008 | Mao |
| 7,468,192 B2 | 12/2008 | Mizuno et al. |
| 7,488,348 B2 | 2/2009 | Truncale et al. |
| 7,537,780 B2 | 5/2009 | Mizuno et al. |
| 7,720,533 B2 | 5/2010 | Behravesh et al. |
| 7,824,711 B2 | 11/2010 | Kizer et al. |
| 7,838,040 B2 | 11/2010 | Malinin |
| 7,875,296 B2 | 1/2011 | Binette et al. |
| 7,879,604 B2 | 2/2011 | Seyedin et al. |
| RE42,208 E | 3/2011 | Truncale et al. |
| 7,897,384 B2 | 3/2011 | Binette et al. |
| 7,901,457 B2 | 3/2011 | Truncale et al. |
| 7,901,461 B2 | 3/2011 | Harmon et al. |
| 8,017,394 B2 | 9/2011 | Adkisson, IV et al. |
| 8,025,901 B2 | 9/2011 | Kao et al. |
| 8,137,702 B2 | 3/2012 | Binette et al. |
| 8,163,549 B2 | 4/2012 | Yao et al. |
| 8,480,757 B2 | 7/2013 | Gage et al. |
| 8,497,121 B2 | 7/2013 | Yao et al. |
| 8,518,433 B2 | 8/2013 | Kizer et al. |
| 8,524,268 B2 | 9/2013 | Kizer et al. |
| 8,652,507 B2 | 2/2014 | Kizer et al. |
| 8,765,165 B2 | 7/2014 | Kizer et al. |
| 8,784,863 B2 | 7/2014 | Kizer et al. |
| 8,834,914 B2 | 9/2014 | Kizer et al. |
| 2001/0004710 A1 | 6/2001 | Felt et al. |
| 2001/0006634 A1 | 7/2001 | Zaleske et al. |
| 2001/0014473 A1 | 8/2001 | Rieser et al. |
| 2001/0014475 A1 | 8/2001 | Frondoza et al. |
| 2001/0051834 A1 | 12/2001 | Frondoza et al. |
| 2001/0055621 A1 | 12/2001 | Baugh et al. |
| 2002/0004038 A1 | 1/2002 | Baugh et al. |
| 2002/0009805 A1 | 1/2002 | Nevo et al. |
| 2002/0012705 A1 | 1/2002 | Domb |
| 2002/0028192 A1 | 3/2002 | Dimitrijevich et al. |
| 2002/0029055 A1 | 3/2002 | Bonutti |
| 2002/0045940 A1 | 4/2002 | Giannetti et al. |
| 2002/0055755 A1 | 5/2002 | Bonutti |
| 2002/0062151 A1 | 5/2002 | Altman et al. |
| 2002/0064512 A1 | 5/2002 | Petersen et al. |
| 2002/0082623 A1 | 6/2002 | Osther et al. |
| 2002/0095160 A1 | 7/2002 | Bonutti |
| 2002/0099401 A1 | 7/2002 | Bonutti |
| 2002/0099448 A1 | 7/2002 | Hiles et al. |
| 2002/0106625 A1 | 8/2002 | Hung et al. |
| 2002/0123142 A1 | 9/2002 | Hungerford et al. |
| 2002/0128683 A1 | 9/2002 | Epstein |
| 2002/0133235 A1 | 9/2002 | Hungerford et al. |
| 2002/0150550 A1 | 10/2002 | Petersen |
| 2002/0151974 A1 | 10/2002 | Bonassar et al. |
| 2002/0159982 A1 | 10/2002 | Bonassar et al. |
| 2002/0159985 A1 | 10/2002 | Baugh et al. |
| 2002/0183850 A1* | 12/2002 | Felt et al. .................. 623/20.16 |
| 2002/0198490 A1 | 12/2002 | Wirt et al. |
| 2002/0198599 A1 | 12/2002 | Haldimann |
| 2003/0009147 A1 | 1/2003 | Bonutti |
| 2003/0009235 A1 | 1/2003 | Manrique et al. |
| 2003/0039695 A1 | 2/2003 | Geistlich et al. |
| 2003/0040113 A1 | 2/2003 | Mizuno et al. |
| 2003/0065389 A1 | 4/2003 | Petersen |
| 2003/0069605 A1 | 4/2003 | Bonutti et al. |
| 2003/0077244 A1 | 4/2003 | Petersen |
| 2003/0099620 A1 | 5/2003 | Zaleske et al. |
| 2003/0114936 A1 | 6/2003 | Sherwood et al. |
| 2003/0134032 A1 | 7/2003 | Chaouk et al. |
| 2003/0151974 A1 | 8/2003 | Kutty et al. |
| 2003/0153078 A1 | 8/2003 | Libera et al. |
| 2003/0176602 A1 | 9/2003 | Schmidt et al. |
| 2003/0181939 A1 | 9/2003 | Bonutti |
| 2003/0187387 A1 | 10/2003 | Wirt et al. |
| 2003/0195628 A1 | 10/2003 | Bao et al. |
| 2003/0199979 A1 | 10/2003 | Mcguckin, Jr. |
| 2003/0211073 A1 | 11/2003 | Goupil et al. |
| 2003/0220649 A1 | 11/2003 | Bao et al. |
| 2003/0223956 A1 | 12/2003 | Goupil et al. |
| 2004/0030404 A1 | 2/2004 | Noll et al. |
| 2004/0030406 A1 | 2/2004 | Ochi et al. |
| 2004/0033212 A1 | 2/2004 | Thomson et al. |
| 2004/0042960 A1 | 3/2004 | Frey et al. |
| 2004/0044408 A1 | 3/2004 | Hungerford et al. |
| 2004/0048796 A1 | 3/2004 | Hariri et al. |
| 2004/0059416 A1 | 3/2004 | Murray et al. |
| 2004/0064192 A1 | 4/2004 | Bubb |
| 2004/0064193 A1 | 4/2004 | Evans et al. |
| 2004/0073308 A1 | 4/2004 | Kuslich et al. |
| 2004/0078073 A1 | 4/2004 | Bonutti |
| 2004/0078077 A1 | 4/2004 | Binette et al. |
| 2004/0078090 A1 | 4/2004 | Binette et al. |
| 2004/0092946 A1 | 5/2004 | Bagga et al. |
| 2004/0097714 A1 | 5/2004 | Maubois et al. |

(56) References Cited

U.S. PATENT DOCUMENTS

| | | |
|---|---|---|
| 2004/0097829 A1 | 5/2004 | McRury et al. |
| 2004/0117033 A1 | 6/2004 | Frondoza et al. |
| 2004/0127987 A1 | 7/2004 | Evans et al. |
| 2004/0134502 A1 | 7/2004 | Mizuno et al. |
| 2004/0138522 A1 | 7/2004 | Haarstad et al. |
| 2004/0151705 A1 | 8/2004 | Mizuno et al. |
| 2004/0172045 A1 | 9/2004 | Eriksson et al. |
| 2004/0175690 A1 | 9/2004 | Mishra et al. |
| 2004/0176787 A1 | 9/2004 | Mishra et al. |
| 2004/0181240 A1 | 9/2004 | Tseng et al. |
| 2004/0191900 A1 | 9/2004 | Mizuno et al. |
| 2004/0193181 A1 | 9/2004 | Bonutti |
| 2004/0219182 A1 | 11/2004 | Gomes et al. |
| 2004/0228901 A1 | 11/2004 | Trieu et al. |
| 2004/0230303 A1 | 11/2004 | Gomes et al. |
| 2004/0230309 A1 | 11/2004 | DiMauro et al. |
| 2005/0026133 A1 | 2/2005 | Nakatsuji et al. |
| 2005/0032015 A1 | 2/2005 | Mcsurdy, Jr. |
| 2005/0038520 A1 | 2/2005 | Binette et al. |
| 2005/0043805 A1 | 2/2005 | Chudik |
| 2005/0043814 A1 | 2/2005 | Kusanagi et al. |
| 2005/0054595 A1 | 3/2005 | Binette et al. |
| 2005/0064042 A1 | 3/2005 | Vunjak-Novakovic et al. |
| 2005/0079159 A1 | 4/2005 | Shastri et al. |
| 2005/0095235 A1 | 5/2005 | Austin et al. |
| 2005/0095666 A1 | 5/2005 | Jhavar et al. |
| 2005/0113736 A1 | 5/2005 | Orr et al. |
| 2005/0113937 A1 | 5/2005 | Binette et al. |
| 2005/0119754 A1 | 6/2005 | Trieu et al. |
| 2005/0123520 A1 | 6/2005 | Eavey et al. |
| 2005/0124038 A1 | 6/2005 | Aguiar et al. |
| 2005/0125077 A1 | 6/2005 | Harmon et al. |
| 2005/0136046 A1 | 6/2005 | Pines et al. |
| 2005/0137600 A1 | 6/2005 | Jacobs et al. |
| 2005/0139656 A1 | 6/2005 | Arnouse |
| 2005/0152882 A1* | 7/2005 | Kizer et al. .................. 424/93.7 |
| 2005/0152886 A1 | 7/2005 | Baugh et al. |
| 2005/0152961 A1 | 7/2005 | Austin et al. |
| 2005/0171470 A1 | 8/2005 | Kucklick et al. |
| 2005/0175657 A1 | 8/2005 | Hunter et al. |
| 2005/0175704 A1 | 8/2005 | Petersen |
| 2005/0175711 A1 | 8/2005 | Kralovee et al. |
| 2005/0177249 A1 | 8/2005 | Kladakis et al. |
| 2005/0186247 A1 | 8/2005 | Hunter |
| 2005/0186283 A1 | 8/2005 | Geistlich et al. |
| 2005/0186673 A1 | 8/2005 | Geistlich et al. |
| 2005/0192532 A1 | 9/2005 | Kucklick et al. |
| 2005/0196387 A1 | 9/2005 | Seyedin et al. |
| 2005/0196460 A1 | 9/2005 | Malinin |
| 2005/0203342 A1 | 9/2005 | Kucklick et al. |
| 2005/0209601 A1 | 9/2005 | Bowman et al. |
| 2005/0209602 A1 | 9/2005 | Bowman et al. |
| 2005/0222687 A1 | 10/2005 | Vunjak-Novakovic et al. |
| 2005/0226856 A1 | 10/2005 | Ahlfors |
| 2005/0234298 A1 | 10/2005 | Kucklick et al. |
| 2005/0234485 A1 | 10/2005 | Seegert et al. |
| 2005/0244454 A1 | 11/2005 | Elson et al. |
| 2005/0250697 A1 | 11/2005 | Maubois et al. |
| 2005/0250698 A1 | 11/2005 | Maubois et al. |
| 2005/0251268 A1 | 11/2005 | Truncale |
| 2005/0265980 A1 | 12/2005 | Chen et al. |
| 2005/0267584 A1 | 12/2005 | Burdulis, Jr. et al. |
| 2005/0273129 A1 | 12/2005 | Michels et al. |
| 2005/0287218 A1 | 12/2005 | Chaouk et al. |
| 2005/0288796 A1 | 12/2005 | Awad et al. |
| 2006/0008530 A1 | 1/2006 | Seyedin et al. |
| 2006/0009779 A1 | 1/2006 | Collins et al. |
| 2006/0019389 A1 | 1/2006 | Yayon et al. |
| 2006/0024373 A1 | 2/2006 | Shahar et al. |
| 2006/0024826 A1 | 2/2006 | Bonassar et al. |
| 2006/0029679 A1 | 2/2006 | Dolecek |
| 2006/0041270 A1 | 2/2006 | Lenker et al. |
| 2006/0073588 A1 | 4/2006 | Adkisson et al. |
| 2006/0078872 A1 | 4/2006 | Taguchi et al. |
| 2006/0099706 A1 | 5/2006 | Massey et al. |
| 2006/0111738 A1 | 5/2006 | Wenchell |
| 2006/0111778 A1 | 5/2006 | Michalow |
| 2006/0128016 A1 | 6/2006 | Tokushima et al. |
| 2006/0134093 A1 | 6/2006 | Ronfard |
| 2006/0134094 A2 | 6/2006 | Delmotte et al. |
| 2006/0147547 A1 | 7/2006 | Yayon |
| 2006/0153815 A1 | 7/2006 | Seyda et al. |
| 2006/0183224 A1 | 8/2006 | Aerts et al. |
| 2006/0195188 A1 | 8/2006 | O'Driscoll et al. |
| 2006/0210643 A1 | 9/2006 | Truncale et al. |
| 2006/0216822 A1 | 9/2006 | Mizuno et al. |
| 2006/0228391 A1 | 10/2006 | Seyedin et al. |
| 2006/0240064 A9 | 10/2006 | Hunter et al. |
| 2006/0240555 A1 | 10/2006 | Ronfard |
| 2006/0251631 A1 | 11/2006 | Adkisson, IV et al. |
| 2006/0264966 A1 | 11/2006 | Armstrong |
| 2006/0275273 A1 | 12/2006 | Seyedin et al. |
| 2006/0281173 A1 | 12/2006 | Fukuda et al. |
| 2006/0292131 A1 | 12/2006 | Binette et al. |
| 2007/0014867 A1 | 1/2007 | Kusanagi et al. |
| 2007/0031471 A1 | 2/2007 | Peyman |
| 2007/0038299 A1 | 2/2007 | Stone et al. |
| 2007/0041952 A1 | 2/2007 | Guilak et al. |
| 2007/0077236 A1 | 4/2007 | Osther |
| 2007/0087032 A1 | 4/2007 | Chang et al. |
| 2007/0098759 A1 | 5/2007 | Malinin |
| 2007/0106394 A1 | 5/2007 | Chen |
| 2007/0128155 A1 | 6/2007 | Seyedin et al. |
| 2007/0184550 A1 | 8/2007 | Miyauchi et al. |
| 2007/0191781 A1 | 8/2007 | Richards et al. |
| 2007/0212389 A1 | 9/2007 | Weiss et al. |
| 2007/0213660 A1 | 9/2007 | Richards et al. |
| 2007/0250164 A1 | 10/2007 | Troxel |
| 2007/0292945 A1 | 12/2007 | Lin et al. |
| 2007/0299517 A1 | 12/2007 | Davisson et al. |
| 2008/0009942 A1 | 1/2008 | Mizuno et al. |
| 2008/0031934 A1 | 2/2008 | MacPhee et al. |
| 2008/0033331 A1 | 2/2008 | MacPhee et al. |
| 2008/0033332 A1 | 2/2008 | MacPhee et al. |
| 2008/0033333 A1 | 2/2008 | MacPhee et al. |
| 2008/0039940 A1 | 2/2008 | Hashimoto et al. |
| 2008/0039954 A1 | 2/2008 | Long et al. |
| 2008/0051624 A1 | 2/2008 | Bonutti |
| 2008/0065210 A1 | 3/2008 | McKay |
| 2008/0071385 A1 | 3/2008 | Binette et al. |
| 2008/0081369 A1 | 4/2008 | Adkisson, IV et al. |
| 2008/0103564 A1 | 5/2008 | Burkinshaw et al. |
| 2008/0113007 A1 | 5/2008 | Kurihara et al. |
| 2008/0153157 A1 | 6/2008 | Yao et al. |
| 2008/0154370 A1 | 6/2008 | Mathies |
| 2008/0199429 A1 | 8/2008 | Hollander et al. |
| 2008/0274157 A1 | 11/2008 | Vunjak-Novakovic et al. |
| 2008/0299214 A1 | 12/2008 | Seyedin et al. |
| 2009/0012629 A1 | 1/2009 | Yao et al. |
| 2009/0069901 A1 | 3/2009 | Truncale et al. |
| 2009/0143867 A1 | 6/2009 | Gage et al. |
| 2009/0149893 A1 | 6/2009 | Semler et al. |
| 2009/0155229 A1 | 6/2009 | Yayon |
| 2009/0181092 A1 | 7/2009 | Thorne et al. |
| 2009/0181093 A1 | 7/2009 | Thorne et al. |
| 2009/0181892 A1 | 7/2009 | Thorne et al. |
| 2009/0214614 A1 | 8/2009 | Everland et al. |
| 2009/0291112 A1 | 11/2009 | Truncale et al. |
| 2009/0319045 A1 | 12/2009 | Truncale et al. |
| 2010/0015202 A1 | 1/2010 | Semler et al. |
| 2010/0086594 A1 | 4/2010 | Amit et al. |
| 2010/0121311 A1 | 5/2010 | Seegert et al. |
| 2010/0168856 A1 | 7/2010 | Long et al. |
| 2010/0209397 A1 | 8/2010 | Maor |
| 2010/0209408 A1 | 8/2010 | Stephen A. et al. |
| 2010/0274362 A1 | 10/2010 | Yayon et al. |
| 2010/0303765 A1 | 12/2010 | Athanasiou et al. |
| 2010/0322994 A1 | 12/2010 | Kizer et al. |
| 2011/0009963 A1 | 1/2011 | Binette et al. |
| 2011/0052705 A1 | 3/2011 | Malinin |
| 2011/0070271 A1 | 3/2011 | Truncale et al. |
| 2011/0091517 A1 | 4/2011 | Binette et al. |
| 2011/0097381 A1 | 4/2011 | Binette et al. |
| 2011/0166669 A1 | 7/2011 | Truncale et al. |

(56) References Cited

U.S. PATENT DOCUMENTS

| | | | |
|---|---|---|---|
| 2011/0177134 A1 | 7/2011 | Harmon et al. | |
| 2011/0196508 A1 | 8/2011 | Truncale et al. | |
| 2011/0256095 A1 | 10/2011 | Seyedin et al. | |
| 2012/0009224 A1 | 1/2012 | Kizer et al. | |
| 2012/0009270 A1 | 1/2012 | Kizer et al. | |
| 2012/0156265 A1 | 6/2012 | Binette et al. | |
| 2012/0183586 A1 | 7/2012 | Yao et al. | |
| 2012/0239146 A1 | 9/2012 | Kizer et al. | |
| 2013/0330415 A1 | 12/2013 | Yao et al. | |
| 2014/0178343 A1 | 6/2014 | Yao et al. | |
| 2014/0335612 A1 | 11/2014 | Yao et al. | |

FOREIGN PATENT DOCUMENTS

| | | | | |
|---|---|---|---|---|
| CA | 2261292 A1 | 7/1997 | | |
| CA | 2261292 C | 7/1997 | | |
| CA | 2285382 A1 | 10/1998 | | |
| CA | 2441994 A1 | 3/2002 | | |
| CA | 2445356 A1 | 10/2003 | | |
| CA | 2445356 C | 10/2003 | | |
| CA | 2445558 A1 | 10/2003 | | |
| CA | 2445558 C | 10/2003 | | |
| CA | 2449227 A1 | 11/2003 | | |
| CA | 2449227 C | 11/2003 | | |
| CA | 2522133 A1 | 4/2004 | | |
| CA | 2522133 C | 4/2004 | | |
| CA | 2475905 A1 | 7/2004 | | |
| CA | 2475905 C | 7/2004 | | |
| CA | 2480712 A1 | 9/2004 | | |
| CA | 2487029 A1 | 11/2004 | | |
| CA | 2487042 A1 | 11/2004 | | |
| CA | 2496184 A1 | 2/2005 | | |
| CA | 2563082 A1 | 3/2005 | | |
| CA | 2563082 A1 | 11/2005 | | |
| CA | 2570521 A1 | 3/2006 | | |
| CA | 2631520 A1 | 6/2007 | | |
| CA | 2708147 A1 | 12/2008 | | |
| CA | 2717725 A1 | 3/2009 | | |
| EP | 0006216 A1 | 1/1980 | | |
| EP | 0133934 A2 | 3/1985 | | |
| EP | 0341007 A2 | 4/1989 | | |
| EP | 1142581 A2 | 11/1991 | | |
| EP | 0610423 B1 | 10/1992 | | |
| EP | 0654078 B1 | 6/1993 | | |
| EP | 0493387 B1 | 10/1993 | | |
| EP | 0641007 A2 | 1/1994 | | |
| EP | 0592242 A1 | 4/1994 | | |
| EP | 0669138 A2 | 2/1995 | | |
| EP | 0906069 B1 | 11/1996 | | |
| EP | 0877632 B1 | 9/1997 | | |
| EP | 0867193 | * | 3/1998 | .............. A61L 31/00 |
| EP | 01010356 A1 | 6/2000 | | |
| EP | 1132061 A2 | 9/2001 | | |
| EP | 1264607 A1 | 12/2002 | | |
| EP | 1003568 B1 | 4/2003 | | |
| EP | 0592242 B1 | 7/2003 | | |
| EP | 1538196 A1 | 8/2003 | | |
| EP | 1410810 A1 | 10/2003 | | |
| EP | 1410810 B1 | 10/2003 | | |
| EP | 1410811 A1 | 10/2003 | | |
| EP | 1410811 B1 | 10/2003 | | |
| EP | 1433423 A1 | 10/2003 | | |
| EP | 1433423 B1 | 10/2003 | | |
| EP | 1599126 | 3/2004 | | |
| EP | 1618178 B1 | 4/2004 | | |
| EP | 1506790 A1 | 8/2004 | | |
| EP | 1512739 A1 | 9/2004 | | |
| EP | 1471140 A1 | 10/2004 | | |
| EP | 1537883 A2 | 12/2004 | | |
| EP | 1537883 A3 | 12/2004 | | |
| EP | 1537883 B1 | 12/2004 | | |
| EP | 1691727 B1 | 12/2004 | | |
| EP | 1958651 B1 | 12/2004 | | |
| EP | 2335650 A1 | 12/2004 | | |
| EP | 2338441 A1 | 12/2004 | | |
| EP | 2338442 A1 | 12/2004 | | |
| EP | 2338533 A1 | 12/2004 | | |
| EP | 1561481 A2 | 2/2005 | | |
| EP | 1561481 A3 | 2/2005 | | |
| EP | 1561481 B1 | 2/2005 | | |
| EP | 1753860 B1 | 2/2005 | | |
| EP | 1535578 A1 | 6/2005 | | |
| EP | 1535633 A1 | 6/2005 | | |
| EP | 1387703 B1 | 7/2006 | | |
| EP | 1303184 B1 | 9/2006 | | |
| EP | 1788077 A1 | 5/2007 | | |
| EP | 0920490 | 2/2008 | | |
| EP | 2101681 B1 | 8/2011 | | |
| EP | 2335650 B1 | 10/2012 | | |
| EP | 2338441 B1 | 1/2013 | | |
| EP | 2338442 B1 | 1/2013 | | |
| GB | 2105198 A | 3/1983 | | |
| GB | 2175507 A | 5/1985 | | |
| GB | 2404607 A | 9/2005 | | |
| JP | 59135054 A | 8/1984 | | |
| JP | 10036534 A | 2/1998 | | |
| JP | 2001519700 T | 10/2001 | | |
| JP | 2002233567 A | 8/2002 | | |
| JP | 2004136096 A | 5/2004 | | |
| JP | 2006230749 A | 9/2006 | | |
| JP | 2003102755 A | 4/2008 | | |
| WO | 8002501 A1 | 5/1980 | | |
| WO | 8505274 A1 | 5/1985 | | |
| WO | 9000060 A1 | 1/1990 | | |
| WO | WO-9101711 A1 | 2/1991 | | |
| WO | WO-9209697 A1 | 6/1992 | | |
| WO | 9603160 A1 | 2/1996 | | |
| WO | WO-9603112 A1 | 2/1996 | | |
| WO | WO-9639170 A1 | 12/1996 | | |
| WO | 9711090 A1 | 3/1997 | | |
| WO | WO-9726847 A1 | 7/1997 | | |
| WO | 9804681 A1 | 2/1998 | | |
| WO | WO-9844874 A1 | 10/1998 | | |
| WO | WO-9907417 A1 | 2/1999 | | |
| WO | 9951164 A1 | 3/1999 | | |
| WO | 0029484 A1 | 11/1999 | | |
| WO | WO-0006216 A1 | 2/2000 | | |
| WO | WO-0048837 A1 | 8/2000 | | |
| WO | 0056251 | 9/2000 | | |
| WO | WO-0062832 A1 | 10/2000 | | |
| WO | WO-0074741 A2 | 12/2000 | | |
| WO | WO-0074741 A3 | 12/2000 | | |
| WO | WO-0102030 A2 | 1/2001 | | |
| WO | WO-0105443 A1 | 1/2001 | | |
| WO | WO-0110356 A2 | 2/2001 | | |
| WO | WO-0123014 A1 | 4/2001 | | |
| WO | WO-0123014 A1 | 4/2001 | | |
| WO | WO-0167961 A1 | 9/2001 | | |
| WO | WO-0168811 A2 | 9/2001 | | |
| WO | WO-0168811 A3 | 9/2001 | | |
| WO | WO-0185225 A2 | 11/2001 | | |
| WO | WO-0197872 A1 | 12/2001 | | |
| WO | 0224244 A2 | 3/2002 | | |
| WO | 0276285 A2 | 3/2002 | | |
| WO | WO-0185225 A3 | 3/2002 | | |
| WO | 0280991 A2 | 4/2002 | | |
| WO | 0267856 A2 | 9/2002 | | |
| WO | WO-02089868 A1 | 11/2002 | | |
| WO | 03077794 A2 | 3/2003 | | |
| WO | 2004028584 A1 | 9/2003 | | |
| WO | WO-03093433 A2 | 11/2003 | | |
| WO | WO-03100417 A1 | 12/2003 | | |
| WO | 2004078032 A2 | 3/2004 | | |
| WO | 2004078032 A3 | 3/2004 | | |
| WO | 2004096983 A2 | 4/2004 | | |
| WO | WO-2004028547 A1 | 4/2004 | | |
| WO | 2004105576 A2 | 5/2004 | | |
| WO | WO-03093433 A3 | 7/2004 | | |
| WO | WO-2004078035 A2 | 9/2004 | | |
| WO | WO-2004078955 A1 | 9/2004 | | |
| WO | WO-2004110308 A2 | 12/2004 | | |
| WO | WO-2004110512 A2 | 12/2004 | | |
| WO | 2005081870 A2 | 2/2005 | | |

(56) References Cited

FOREIGN PATENT DOCUMENTS

| | | |
|---|---|---|
| WO | WO-2005011765 A1 | 2/2005 |
| WO | 2005018491 A2 | 3/2005 |
| WO | 2005092208 A1 | 3/2005 |
| WO | 2005092405 A1 | 3/2005 |
| WO | 2005110278 A2 | 3/2005 |
| WO | WO-2004110512 A3 | 5/2005 |
| WO | WO-2005044326 A1 | 5/2005 |
| WO | 2005058207 A1 | 6/2005 |
| WO | 2006002253 A2 | 6/2005 |
| WO | 2005060987 A1 | 7/2005 |
| WO | 2005061018 A1 | 7/2005 |
| WO | 2006033698 A2 | 7/2005 |
| WO | WO-2005061019 A2 | 7/2005 |
| WO | WO-2005065079 A2 | 7/2005 |
| WO | 2006068972 A2 | 12/2005 |
| WO | WO-2005113751 A1 | 12/2005 |
| WO | WO-2006002253 A3 | 1/2006 |
| WO | 2006090372 A2 | 2/2006 |
| WO | 2006090372 A3 | 2/2006 |
| WO | WO-2006017176 A2 | 2/2006 |
| WO | 2006113642 A1 | 4/2006 |
| WO | WO-2006039484 A2 | 4/2006 |
| WO | WO-2006033698 A3 | 7/2006 |
| WO | WO-2006121612 A1 | 11/2006 |
| WO | WO-2005081870 A3 | 12/2006 |
| WO | WO-2006039484 A3 | 1/2007 |
| WO | 2007025290 A2 | 3/2007 |
| WO | 2007102149 A2 | 3/2007 |
| WO | 2007115336 A2 | 4/2007 |
| WO | 2007054939 A2 | 5/2007 |
| WO | 2007067637 A2 | 6/2007 |
| WO | 2007143726 A2 | 6/2007 |
| WO | WO-2007089942 A2 | 8/2007 |
| WO | WO-2007089948 A2 | 8/2007 |
| WO | WO-2008019127 A2 | 8/2007 |
| WO | WO-2007025290 A3 | 10/2007 |
| WO | 2007143726 A2 | 12/2007 |
| WO | 2008106254 A2 | 1/2008 |
| WO | WO-2007089948 A3 | 1/2008 |
| WO | 2008021127 A2 | 2/2008 |
| WO | WO-2008019128 A2 | 2/2008 |
| WO | WO-2008019129 A2 | 2/2008 |
| WO | 2008128075 A1 | 4/2008 |
| WO | 2008079194 A1 | 7/2008 |
| WO | WO-2008079613 A1 | 7/2008 |
| WO | 2009039469 A1 | 3/2009 |
| WO | 2009111069 A1 | 3/2009 |
| WO | 2009076164 A2 | 6/2009 |
| WO | 2010078040 A1 | 7/2010 |

OTHER PUBLICATIONS

Langer, F. et al, The Immunogenicity of Fresh and Frozen Allogeneic Bone, JBJS, 1975, pp. 216-220, vol. 57-A, No. 2.

Lavrishcheva, G.I., Filling Bone Cavities with Minced Cartilage, Ortopediia travmatologiia I protezirovanie, 1955, pp. 80, vol. 1.

Lee, J.W., Preplanned correction of enophthalmos using diced cartilage grafts, British J. Plastic Surg, 2000, pp. 17-23, vol. 53.

Lemperg, R., et al, Transplantation of diced rib cartilage to the hip joint. Experimental study on adult dogs, Acta Soc Med Ups, 1965, pp. 197-212, vol. 70, No. 3.

Lennert, K.H. and Haas, H.G., Fibrin Adhesive in the Surgical Treatment of the Pseudoarthrosis of the Scaphoid Bone- Methods and Results, Unfallchirurgie, 1988, pp. 158-160, vol. 14, No. 3.

Leopold, G., XIV. Experimental Studies into the Etiology of Tumors, Archiv f. path. Anat., 1881, pp. 283-324, vol. LXXXV, No. 2.

Limberg, A.A., Supporting and Contour Plastic Repair by Needle Administration of Minced Carthage, Vestnik khirurgii imemi I.I. Grekova, 1957, pp. 68-73, vol. 78, No. 4.

Limberg, A.A., The use of diced cartilage by injection with a needle. Part 1. Clinical investigations, Plast Reconstr Surg Transplant Bull., 1961, pp. 523-36, vol. 28.

Limberg, A.A., The use of diced cartilage by injection with a needle. Part 2. Morphologic Changes in the Diced Human Cartilage After Auto- and Homoplasty, Plast Reconstr Surg Transplant Bull., 1961, pp. 649-655, vol. 28.

Loeb, L, Autotransplantation and Homoiotransplantation of Cartilage in the Guinea-Pig, Am. J. Pathology, 1926, pp. 111-122, vol. II.

Lu, Y. et al, Minced Cartilage without Cell Culture Serves as an Effective Intraoperative Cell Source for Cartilage Repair, J Orthop Res., 2006, pp. 1261-1270, vol. 24, No. 6.

Lucht, U. et al, Fibrin sealant in bone transplantation. no. effects on blood flow and bone formation in dogs, Acta Orthop Scand., 1986, pp. 19-24, vol. 57, No. 1.

Mahomed, M.N. et al, The long-term success of fresh, small fragment osteochondral allografts used for intraarticular post-traumatic defects in the knee joint, Orthopedics, 1992, pp. 1191-1199, vol. 15, No. 10.

Maletius, W. and Lundberg, M., Refixation of large chondral fragments on the weight-bearing area of the knee joint: a report of two cases, Arthroscopy., 1994, pp. 630-633, vol. 10, No. 6.

Mankin, H.J., Localization of Tritiated Thymidine in Articular Cartilage of Rabbits: II. Repair in Immature Cartilage, JBJS, 1962, pp. 688-698, vol. 44.

Mankin, H.J., Localization of Tritiated Thymidine in Articular Cartilage of Rabbits: III. Mature Articular Cartilage, JBJS, 1963, pp. 529-540, vol. 45.

Mankin, H.J., Current Concepts Review, The Response of Articular Cartilage to Mechanical Injury, JBJS, 1982, pp. 460-466, vol. 64, No. 3.

Marcacci, M. et al, Articular cartilage engineering with Hyalograft C: 3-year clinical results, Clin Orthop Relat Res., 2005, pp. 96-105, No. 435.

Marcacci, M. et al, Use of autologous grafts for reconstruction of osteochondral defects of the knee, Orthopedics, 1999, pp. 595-600, vol. 22, No. 6.

Marchac, D. and Sandor, G., Face lifts and sprayed fibrin glue: an outcome analysis of 200 patients, Br J Plast Surg., 1994, pp. 306-309, vol. 47, No. 5.

Marchac, D. et al, Fibrin glue fixation in forehead endoscopy: evaluation of our experience with 206 cases, Plast Reconstr Surg., 1997, pp. 713-714, vol. 100, No. 3.

Matras, H., Fibrin Seal: The State of the Art, J. Oral Maxilofac Surg, 1985, pp. 605-611, vol. 43.

Matsusue, Y. et al, Biodegradable Pin Fixation of Osteochondral Fragments of the Knee, Clin Ortho Rel Res, 1996, pp. 166-173, No. 322.

McDermott, A.G.P. et al, Fresh Small-Fragment Osteochondral Allografts, Clin Orthop Relat Res., 1985, pp. 96-102, No. 197.

McKibbin, B, Immature Joint Cartilage and the Homograft Reaction, JBJS, 1971, pp. 123-135, vol. 53B, No. 1.

Meachim, G. and Roberts, C., Repair of the joint surface from subarticular tissue in the rabbit knee, J Anat., 1971, pp. 317-327, vol. 109, Part 2.

Meyers, M.H. and Herron, M., A Fibrin Adhesive Seal for the Repair of Osteochondral Fracture Fragments, Clin Ortho Rel Res, 1984, pp. 258-263, No. 182.

Mitchell, N. and Shepard, N., The resurfacing of adult rabbit articular cartilage by multiple perforations through the subchondral bone, JBJS, 1976, pp. 230-3, vol. 58, No. 2.

Mithofer, K. et al, Functional outcome of knee articular cartilage repair in adolescent athletes, Am J Sports Med., 2005, pp. 1147-1153, vol. 33, No. 8.

Miura, Y et al, Brief exposure to high-dose transforming growth factor-beta1 enhances periosteal chondrogenesis in vitro: a preliminary report, JBJS, 2002, pp. 793-799, vol. 84-A, No. 5.

Murray, M.M. and Spector, M, The migration of cells from the ruptured human anterior cruciate ligament into collagen-glycosaminoglycan regeneration templates in vitro, Biomaterials, 2001, pp. 2393-2402, vol. 22.

Nageotte, J., The Organization of Matter in its Connections with Life. Studies of General Anatomy and Experimental Morphology on teh Connective Tissue and the Nerve, L'Organisation De La Matiere, 1922, pp. 95-98.

(56) References Cited

OTHER PUBLICATIONS

Niekisch, V.R., English Summary only of Possible methods of using fibrin-glue protection in maxillo facial surgery, Zahn Mund Kieferheilkd Zentralbl, 1980, pp. 555-561, vol. 68, No. 6.
Nixon, A.J., et al, Isolation, propagation, and cryopreservation of equine articular chondrocytes, Am J Vet Res, 1992, pp. 2364-2370, vol. 53, No. 12.
Nixon, A.J., and Fortier, L.A, New Horizons in Articular Cartilage Repair, AAEP Proceedings, 2001, pp. 217-226, vol. 47.
O'Driscoll, S.W. et al, The chondrogenic potential of free autogenous periosteal grafts for biological resurfacing of major full-thickness defects in joint surfaces under the influence of continuous passive motion. An experimental investigation in the rabbit, J Bone Joint Surg Am, 1986, pp. 1017-1035, vol. 68, No. 7.
O'Driscoll, S.W. and Salter, R.B., The Repair of Major Osteochondral Defects in Joint Surfaces by Neochondrogenesis with Autogenous Osteoperiosteal Grafts Stimulated by Continuous Passive Motion, Clin Ortho Rel Res, 1986, pp. 131-140, No. 208.
Oegema, T.R. and Thompson, R.C. Jr, Characterization of a hyaluronic acid-dermatan sulfate proteoglycan complex from dedifferentiated human chondrocyte cultures, J Biol Chem., 1981, pp. 1015-1022, vol. 256, No. 2.
Ohlsen, L. and Widenfalk, B., The Early Development of Articular Cartilage After Perichondrial Grafting, Scand J. Plast Reconstr Surg, 1983, pp. 163-177, vol. 17.
Outerbridge, H.K. et al, The Use of a Lateral Patellar Autologous Graft for the Repair of a Large Osteochondral Defect in the Knee, J Bone Joint Surg Am., 1995, pp. 65-72, vol. 77, No. 1.
Paar, O. et al,Cartilage Adhesion at the Knee Joint, Clinical Follow up Examination, Akt. Traumatol, 1984, pp. 15-19, vol. 14.
Paccola, C.A. et al, Fresh Immature Articular Cartilage Allografts—A Study on the Integration of Chondral and Osteochondral Grafts Both in Normal and in Papain-Treated Knee Joints of Rabbits, Arch Orthop Traumat Surg., 1979, pp. 253-259, vol. 93.
Park, J.J. et al, Comparison of the Bonding Power of Various Autologous Fibrin Tissue Adhesives, Am J Otology, 1997, pp. 655-659, vol. 18, No. 5.
Park, M.S., Tympanoplasty using autologous crushed cartilage, Rev Laryngol Otol Rhinol, 1995, pp. 365-368, vol. 116, No. 5.
Pascone, M. and Dioguardi, D., Fibrin Sealant in Plastic Surgery of the Head, Plastic Surgery Nerve Repair Burns, Fibring Sealing in Surgical and Nonsurgical Fields, 1995, pp. 11-15, vol. 3, Springer-Verlag, Berlin Heidelberg.
Passl, R. et al, Problems of Pure Homologous Articular Cartilage Transplantation, Verh Anat Ges, 1976, pp. 675-678, vol. 70.
Punzet, G. et al, Morphological and Therapeutic Aspects of Osteochondrosis dissecans and Aseptic Bone Necroses, Acta Medica Austriaca, 1978, pp. 17-18, Suppl. No. 11.
Passl, R. et al, Fibrin Gluing of Cartilage Surfaces—Experimental Studies and Clinical Results, Med. u. Sport, 1979, pp. 23-28, vol. 19 (1/2).
Passl, R. et al, Homologous Cartilage Transplants in Animal Experiments, 4th Orthopedics Symposium, Heidelberg, 1981, pp. 102-105, Horst Cotta and Arnim Braun (eds), Georg Thieme Verlag Stuttgart, New York.
Passl, R. and Plenk, H. Jr, Histological observations after replantation of articular cartilage, Unfallchirurgie, 1986, pp. 194-199, vol. 12, No. 4.
Passl, R. and Plenk, H. Jr, Fibrin Sealing of Cartilage Surfaces, Beitr. Orthop. Traumatol, 1989, pp. 503-507, vol. 36, No. 10.
Pech, A., et al, Tissuecol in Septorhinoplasties, Ann. Oto-Laryng., 1988, pp. 629-634, vol. 105.
Peer, L.A., Extended Use of Diced Cartilage Grafts, Meeting of the American Association of Plastic Surgeons, Apr. 21, 23, 1954, pp. 178-185.
Peer, L.A., The Fate of Living and Dead Cartilage Transplanted in Humans, Surg, Gynec, and Obst., 1939, pp. 603-610, vol. 68.

Peer, L.A., Fate of Autogenous Septal Cartilage After Transplantation in Human Tissues, Archv of Otolaryngology, 1941, pp. 696-709, vol. 34, No. 4.
Peer, L.A., The Neglected Septal Cartilage Graft (With Experimental Observations on the Growth of Human Cartilage Grafts), Arch Otolaryngol Head Neck Surg.,1945, pp. 384-396, vol. 42, No. 5.
Peretti, G.M. et al, Bonding of Cartilage Matrices with Cultured Chondrocytes: An Experimental Model, J. Orthopaedic Res, 1998, pp. 89-95, vol. 16.
Peretti, G.M. et al, Biomechanical Analysis of a Chondrocyte-Based Repair Model of Articular Cartilage, Tissue Engineering, 1999, pp. 317-326, vol. 5, No. 4.
Peretti, G.M. et al, Cell-Based Tissue-Engineered Allogeneic Implant for Cartilage Repair, Tissue Engineering, 2000, pp. 567-576, vol. 6, No. 5.
Peretti, G.M. et al, Cell-Based bonding of articular cartilage: An extended Study, J. Biomed Mater Res, 2003, pp. 517-524, vol. 64A.
Peretti, G.M. et al, In vitro bonding of pre-seeded chondrocytes, Sport Sci Health, 2007, pp. 29-33, vol. 2.
Phemister, D.B. and Miller, E.M., The Method of New Joint Formation in Arthroplasty, Surgery, Gynecology and Ostetrics, 1918, pp. 406-447, vol. 26.
Pierce, G.W. and O'Connor, G.B., XXXVI. Reconstruction Surgery of the Nose, Ann. Otol. Rhin. and Laryng., 1938, pp. 437-452, vol. 47.
Piragine, F. et al, Use of Bovine Heterologous Cartilage and Fibrin Sealant in Middle Ear Reconstructive Surgery, Neurosurgery Ophthalmic Surgery ENT, Fibrin Sealing in Surgical and Nonsurgical Fields, 1994, pp. 193-198, vol. 5, Springer-Verlag, New York, USA.
Pitman, M.I. et al, The Use of Adhesives in Chondrocyte Transplantation Surgery: In-Vivo Studies, Bull Hosp Jt Dis Orthop Inst., 1989, pp. 213-220, vol. 49, No. 2.
Plaga, B.R. et al, Fixation of osteochondral fractures in rabbit knees. A comparison of Kirschner wires, fibrin sealant, and polydioxanone pins, J Bone Joint Surg Br., 1992, pp. 292-296, vol. 74, No. 2.
Plenk, H. Jr and Passl, R., Trans- and Replantation of Articular Cartilage Using the Fibrinogen Adhesive System, Gastpar, H. (ed.): Biology of the articular cartilage in health and disease, 1980, pp. 439-447, Schattauer, Stuttgart-New York, USA.
Plenk, H. Jr and Passl, R., Articular Cartilage Transplants in Experiments and Clinical Practice, ACA, Acta Chirurgica Austriaca 21st Seminar of the Austrian Association of Surgical Research, Nov. 13-15, 1997, pp. 1-4, vol. 29, Suppl. No. 137.
Pridie, K.H., A method of resurfacing osteoarthritic knee joints, JBJS, 1959, pp. 618-619, vol. 41B, No. 3.
Prin, A. et al, Effect of purified growth factors on rabbit articular chondrocytes in Monolayer Culture, I. DNA Synthesis, Arthritis & Rheumatism, 1982, pp. 1217-1227, vol. 25, No. 10.
Prudden, T., Article IV. Experimental Studies on the Transplantation, American Journal of the Medical Sciences: Oct. 1881, pp. 360-370, vol. 82, No. 164.
Vachon, A., et al, Neochondrogenesis in free intra-articular, periosteal, and perichondrial autografts in horses, Am J Vet Res, 1989, pp. 1787-1794, vol. 50, No. 10.
Redl, H. et al, Methods of Fibrin Seal Application, Thorac. Cardiovasc. Surgeon, 1982, pp. 223-227, vol. 30.
Roberts, S. et al, Autologous chondrocyte implantation for cartilage repair: monitoring its success by magnetic resonance imaging and histology, Arthritis Res and Therapy, 2003, pp. R60-R73, vol. 5.
Robinson, D. et al, Regenerating hyaline cartilage in articular defects of old chickens using implants of embryonal chick chondrocytes embedded in a new natural delivery substance, Calcif Tissue Int., 1990, pp. 246-253, vol. 46, No. 4.
Ruano-Ravina, A. and Diaz, M.J., Autologous chondrocyte implantation: a systematic review, Osteoarthritis and Cartilage, 2006, pp. 47-51, vol. 14.
Rudderman, R.H., et al, The Fate of Fresh and Preserved, Noncrushed and Crushed Autogenous Cartilage in the Rabbit Model, Ann Plast Surg, 1994, pp. 250-254, vol. 32.
Rupp, G. et al, Fibrin Adhesion of Transposed Autologous Cartilage Bone Grafts to Repair Knee-Joint Defects, Langenbeck's Archives of Surgery, 1978, pp. 676-677, vol. 347, No. 1.

(56) References Cited

OTHER PUBLICATIONS

Saidi, K. et al, Articular Knee Transplant in the Rabbit: Experimental Study and Clinical Projections, Union Medicale du Canada, 1971, pp. 88-99, vol. 100, No. 1.
Salter, R.B., et al, The Biological Effect of Continuous Passive Motion on the Healing of Full-Thickness Defects in ARticular Cartilage, JBJS, 1980, pp. 1232-1251, vol. 62-A, No. 8.
Sampath, T.K., et al, In vitro transformation of mesenchymal cells derived from embryonic muscle into cartilage in response to extracellular matrix components of bone, Proc Natl Acad Sci U S A, 1984, pp. 3419-23, vol. 81, No. 11.
Schlag, G. and Redl, H., Fibrin Sealant in Orthopedic Surgery, Clin Ortho Rel Res, 1988, pp. 269-285, vol. 227.
Schlag, G. and Redl, H., Fibrin adhesive system in bone healing, Acta Orthop Scand., 1983, pp. 655-658, vol. 54, No. 4.
Schobel, H., Compound Prosthesis and Cartilage Layer: Two New Applications of Fibrin Sealing in Reconstructive Middle Ear Surgery, Neurosurgery Ophthalmic Surgery ENT, Fibrin Sealing in Surgical and Nonsurgical Fields, 1994, pp. 186-192, vol. 5, Springer-Verlag, New York, USA.
Schreiber, R.E. et al, A Method for Tissue Engineering of Cartilage by Cell Seeding on Bioresorbable Scaffolds, Ann N Y Acad Sci., 1999, pp. 398-404, vol. 875.
Schwam, B.L., Human Amniotic Membrane Transplantation for the Treatment of Ocular Surface Disease, Northeast Florida Medicine Journal, http://www.dcmsonline.org/jax-medicine/2002journals/augsept2002/amniotic.htm, 2002, print date Mar. 3, 2009, pp. 1-7.
Schwartz, E.R., et al, Sulfate Metabolism in Human Chondrocyte Cultures, J. Clin Investigation, 1974, pp. 1056-1063, vol. 54.
Schwarz, N., et al, The Influence of Fibrin Sealant on Demineralized Bone Matrix-Dependent Osteoinduction, Clin Ortho Rel Re, 1989, pp. 282-287, No. 238.
Shoemaker, S. et al, Effects of fibrin sealant on incorporation of autograft and xenograft tendons within bone tunnels. A preliminary study, J Am J Sports Med., 1989, pp. 318-24, vol. 17, No. 3.
Silverman, R.P., et al, Injectable Tissue-Engineered Cartilage Using a Fibrin Glue Polymer, American Society of Plastic Surgeons, 1999, pp. 1809-1818, vol. 103, No. 7.
Simms, G.F., et al, Diced Homologous Cartilage in Hernioplasty, Jour. Med. Soc. J.J., 1952, pp. 406-407, vol. 49, No. 9.
Sosna, A. and Vavra, J., Use of Fibrin Glue in Orthopedics, Acta Chir. Orthop. Traum., 1984, pp. 8-91, vol. 51, No. 2.
Specchia, N. et al, Fetal chondral homografts in the repair of articular cartilage defects, Blletin Hospital for Joint Diseases, 1996, pp. 230-235, vol. 54, No. 4.
Stoksted, P. and Ladefoged, C., Crushed cartilage in nasal reconstruction, J. Laryngology and Otology, 1986, pp. 897-906, vol. 100.
Tanaka, H. et al, A Study on Experimental Homocartilage Transplantation, Arch Orthop Traumat Surg, 1980, pp. 165-169, vol. 96.
Tanaka, H. and Shinno, N., Histochemical Studies on Regeneration of Articular Cartilage, Tokushima J Exp Med., 1971, pp. 63-73, vol. 18.
Temenoff, J.S. and Mikos, A.G., Review: Tissue engineering for regeneration of articular cartilage, Biomaterials, 2000, pp. 431-440, vol. 21, No. 5.
Tuan, R.S., A second-generation autologous chondrocyte implantation approach to the treatment of focal articular cartilage defects, Arthritis Res Ther., 2007, pp. 109 (1-4), vol. 9, No. 5.
Peretti, G.M. et al, A Biomechanical Analysis of an Engineered Cell-Scaffold Implant for Cartilage Repair, 2001, Ann Plast Surg, pp. 533-537, vol. 46.
Schaffer, D.J. et al, English abstract only of foreign patent No. WO00/74741 A2, international filed, Jun. 8, 2000, one page.
Schaffer, D.J. et al, English abstract only of foreign patent No. WO00/74741 A3, international filed, Jun. 8, 2000, one page.
Cherubine, P. et al, English abstract only of Autologous chondrocyte implantation using a bilayer collagen membrane: a preliminary report, J. Orthop Surg (Hong)Kong), 3002, pp. 10-15, vol. 11, No. 1.
Yamamoto, K, et al, English abstract only of Japanese publication No. 2006230749A, publication date Sep. 7, 2006, one page.

Verwerd, C.D.A. et al, Wound Healing of Autologous Implants in the Nasal Septal Cartilage, ORL, 1991, pp. 310-314, vol. 53.
Wilflingseder, P., Cancellous Bone Grafts, S Afr Med J., 1957, pp. 1267-1271, vol. 31, No. 50.
Wilfingseder, P., Treatment of Mandibular Facial Dysostosis, S Afr Med J., 1957, pp. 1296-1298, vol. 31, No. 51.
Pirsig, W., English Abstract only of Regeneration of septal cartilage in children after septoplasty. A histological study, Acta Otolaryngol, 1975, pp. 451-459, vol. 79, No. 5-6.
Passl, R. et al, Homologous articular cartilage transplantation in animal experiments. Preliminary studies on sheep (author's transl), Arch Orthop Unfallchir., 1976, pp. 243-256, vol. 86, No. 2.
Hunter, W., VI. Of the Structure and Difeafes of Articulating Cartilages, Academiae Grypeswaldensis Bibliotheca, 1775, pp. 514-521, vol. 1.
Wikipedia print out of website—http://en.wikipedia.org/wiki/Alpha-2-Macroglobulin, 8 pages.
Kallio, K.E., Arthroplastia Cutanea, Discussion by T. Heirtom, ACTA Orhtopaedica Scandinavica, 1957, pp. 327-328, vol. 26.
Peer, L.A., Transplanation of Tissues—Cartilage, Bone, Fascia, Tendon, and Muscle, The Williams & Wilkins Company, 1955, pp. 69-137 and 392-393, vol. 1, Baltimore, Maryland, USA.
Mannhelm, A., Abstract—Free Autoplastic Cartilage Transplantation, J. Am Med Assoc., 1926, pp. 2132, vol. 87, No. 25.
Nehrer, S. and Minas, T., Treatment of Articular Cartilage Defects, Investigative Radiology, 2000, pp. 639-646, vol. 35, No. 10.
Prudden, T.M., Experimental studies on the transplantation of cartilage, Am. J. M. Sc., 1881, pp. 360-370, vol. 82.
Shands, A.R., Jr., The regeneration of hyaline cartilage in joints. An experimental study, Arch. Surg., 1931, pp. 137-178, vol. 22.
Cheung, H.S. and Haak, M.H., Growth of osteoblasts on porous calcium phosphate ceramic: an in vitro model for biocompatibility study, Biomaterials, 1989, pp. 63-67, vol. 10.
Sittinger, M. et al, Engineering of cartilage tissue using bioresorbable polymer carriers in perfusion culture, Biomaterials, 1994, pp. 451-456, vol. 15, No. 6.
Polettini, B., English abstract only Experimental Grafts of Cartilage and Bone, J.A.M.A., 1923, p. 360, vol. 80.
Braun, A and Heine, W.D., Abstract of the Use of Fibrin Adhesive in Fixation of Osteochondral Fragments, Year unknown, Canadian Orthopaedic Research Society, pp. 215-216.
Rohrbach, JM et al, Abstract only of Biological corneal replacement an alternative to keratoplasty and keratoprosthesis? A pilot study with heterologous hyaline cartilage in the rabbit model, 1995, Klin Monatsbl. Augenheilkd., pp. 191-196, vol. 207, No. 3.
Fontana, A et al, Abstract only of Cartilage chips synthesized with fibrin glue in rhinoplasty, Aestetic Plast Surg, 1991, pp. 237-240, vol. 15, No. 3.
Mainil-Varlet, P et al, Abstract only of Articular cartilage repair using a tissue engineered cartilage like implant: an animal study, Osteoarthritis Cartilage, 2001, pp. s:6-15, vol. 9.
Erol, OO, The Turkish delight: A pliable graft for rhinoplasty, Plast Reconstro Surg, 2000, pp. 2229-2241, vol. 105, No. 6.
Degroot, J. et al, Age related decrease in Proteoglycan synthesis of human articular chondrocytes, 1999, Arthritis & Rheumatism, pp. 1003-1009, vol. 42, No. 5.
Feder, J. et al, The promise of chondral repair using neocartilage, 2004, Tissue engineering in musculoskeletal clinical practice, 1st Edition, American Academy of Orthopaedic Surgeons, pp. 219-226, Chapter 22, Section 3.
Morales, T.I., Review: Chondrocyte moves: clever strategies?, Osteoarthritis and Cartilage, 2007, pp. 861-871, vol. 15.
Namba, R.S. et al, Spontaneous repair of superficial defects in articular cartilage in a fetal lamb model, 1998, JBJS, pp. 4-10, vol. 80, No. 1.
Williamson, A.K., et al, Compressive properties and function composition relationships of developing bovine articular cartilage, J. Orthopaedic Research, 2001, pp. 1113-1121, vol. 19.
Specchia, N. et al, Fetal chondral homografts in the repair of articular cartilage defects, Bulletin Hospital for Joint Diseases, 1996, pp. 230-235, vol. 54, No. 4.
Brown, K.R. et al, English Abstract of Japanese publication No. 2003-102755, 1 page.

(56) References Cited

OTHER PUBLICATIONS

Cheung, H.S. and Haak, M.H., Growth of osteoblasts on porous calcium phosphate ceramic: an in vitro model for biocompatibility study, Biomaterials, 1989, pp. 63-67., vol. 10.
Lapchinsky, A.G., et al., English abstract only of Apparatus for grinding cartilage in plastic surgery, 1960, primenenija Moskva, pp. 209-213, No. 4.
Imbert, L. et al, English translated Abstract only of Research on cartilage grafts hetero-plastic, 1916, Rev. de chir., pp. 111-128, vol. 52.
Iwamoto, Y. et al, English abstract of WO2005/011765, published Feb. 10, 2005, 1 page.
Ochi, M. et al, English abstract of Japanese publication No. 2002-233567, 1 page.
Sengupta, S. and Lumpur, K., The fate of transplants of articular cartilage in the rabbit, 1974, JBJS, pp. 167-177, vol. 56B, No. 1.
Didier R., English translated Abstract only of the production of cartilage and bone grafts in living and dead rabbits, 1928, Compt. rend. Soc de biol, pp. 443-445, vol. 98.
Dupertuis, S.M., Growth of Young Human Autogenous Cartilage Grafts, Plast Reconstr Surg, 1946, pp. 486-493, vol. 5, No. 6.
Albrecht, F. et al, Closure of Osteochondral Lesions Using Chondral Fragments and Fibrin Adhesive, Arch Orthop Trauma Surg, 1983, pp. 213-217, vol. 101.
Albrecht, F., English Abstract of German article Closure of joint cartilage defects using cartilage fragments and fibrin glue, Fortschr Med., 1983, pp. 1650-1652, vol. 101, No. 37.
Dupertuis, S. M., Actual Growth of Young Cartilage Transplants in Rabbits, Archives of Surgery, 1941, pp. 32-63, vol. 43.
Eberlin, J.L. et al, Osteocartilagenous Reconstruction, Plastic Surgery Nerve Repair Burns, Fibrin Sealing in Surgical and Nonsurgical Fields, 1995, pp. 20-24, vol. 3 Springer-Verlag, Berlin, Heidelberg.
De Kleine, E.H., The Chondrojet, A Simplified Method for Handling of Diced Cartilage, Plast Reconstr Surg, 1946, pp. 95-102, vol. 3, No. 1.
Aston, J.E. and Bentley G., Repair of Articular Surfaces by Allografts of Articular and Growth-Plate Cartilage, J Bone Joint Surg Br.,1986, pp. 29-35, vol. 68, No. 1.
Bacsich, P. and Wyburn, G.M., XXXVIII. The Significance of the Mucoprotein Content on the Survival of Homografts of Cartilage and Cornea, 1947, P.R.S.E., pp. 321-327, vol. LXII, B, Part III.
Bayliss, M.T. and Roughley, P.J., The properties of proteoglycan prepared from human articular cartilage by using associative caesium chloride gradients of high and low starting densities, Biochem. J., 1985, pp. 111-117, vol. 232.
Gently, G. and Greer, R.B. III, Homotransplantation of Isolated Epiphyseal and Articular Cartilage Chondrocytes into Joint Surfaces of Rabbits, Nature, 1971, pp. 385-388, vol. 230.
Berlet, G.C. et al, Treatment of Unstable Osteochondritis Dissecans Lesions of the Knee Using Autogenous Osteochondral Grafts (Mosaicplasty), J. Arthroscopic and Related Surgery, 1999, pp. 312-316, vol. 15, No. 3.
Decher, H., Reduction of Radical Cavities by Means of Homologous Cartilage Chips, Larying. Rhinol. Otol., 1985, pp. 423-426, vol. 64.
Bodo, G. et al, Arthroscopic Autologous Osteochondral Mosaicplasty for the Treatment of Subchondral Cystic Lesion in the Medial Femoral Condyle in a Horse, Acta Veterinaria Hungarica, 2000, pp. 343-354, vol. 48, Vo. 3.
Craigmyle, M.B.L., Cellular Survival in Long-Term Cartilage Grafts in the Rabbit, Transplantation Bulletin, 1958, pp. 123, vol. 5, No. 1.
Craigmyle, M.B.L., An Autoradiographic and Histochemical Study of Long-Term Cartilage Grafts in the Rabbit, J. of Anatomy, 1954, pp. 467-473, vol. 92, Part 3.
Coster, D.J. and Galbraith, J.E.K., Diced cartilage grafts to correct enophthalmos, British J. Ophthalmology, 1980, pp. 135-136, vol. 64.
Cooke, M.E. et al, Manuscript entitled Structured three-dimensional co-culture of mesenchymal stem cells with chondrocyts promotes chondrogenic differentiation without hypertrophy, pp. 1-19.

Chesterman, P.J. et al, Homotransplantation of Articular Cartilage and Isolated Chondrocytes, An Experimental Study in Rabbits, JBJS, 1968, pp. 184-197.
Breadon, G.E., et al, Autografts of Uncrushed and Crushed Bone and Cartilage, Bone and Cartilage Autografts, 1979, pp. 75-80, vol. 105.
Brighton, C.T., et al, Articular Cartilage Preservation and Storage I. Application of Tissue Culture Techniques to the Storage of Viable Articular Cartilage, Arthritis Rheum., 1979, pp. 1093-1101, vol. 22, No. 10.
Brittberg, M. et al, Treatment of Deep Cartilage Defects in the Knee With Autologous Chondrocyte Transplantation, The New England Journal of Medicine, 1994, pp. 889-95, vol. 331, No. 14.
Brittberg, M. Autologous Chondrocyte Transplantation, Clinical Orthopaedics and Related Research, 1999, pp. 5147-5155, No. 367S.
Brittberg, M. et al, Treatment of Deep Cartilage Defects in the Knee with Autologous Chondrocyte Transplantation, N Engl J Med., 1994, pp. 889-895, vol. 331, No. 14.
Brodkin, H.A. and Peer, L.A., Diced Cartilage for Chest Wall Defects, 1954, pp. 97-102, vol. 28, No. 1.
Brown, B.L. et al, Transplantation of Fresh Allografts (Homografts) of Crushed and Uncrushed Cartilage and Bone: A 1-Year Analysis in Rabbits, The Laryngoscope, 1980, pp. 1521-1532, vol. 90.
Bruns, J. et al, Long-Term Follow up Results after Gluing Osteochondral Fragments in Patients with Osteochondrosis Dissecans Langenbecks Arch Chir, 1993, pp. 160-166, vol. 378.
Bruns, J. et al, Autologous rib perichondrial grafts in experimentally induced osteochondral lesions in the sheep-knee joint: morphological results, Virchows Archiv A. Pathol Anat, 1992, pp. 1-8, vol. 421.
Bruns, J. and Henne-Bruns, D., Autologous Perichondrial Transplantation for the Repair of Experimentally Induced Cartilage Defects in the Sheep Knee—Two Glueing Techniques, Orthopedic Surgery Maxillofacial Surgery, Fibrin Sealing in Surgical and Nonsurgical fields, Oct. 27, 1994, pp. 50-60, Springer, Berlin, Heidelberg.
Buckwalter, J.A., Articular Cartilage Injuries, Clinical Orthopaedics and Related Research, 2002, pp. 21-37, vol. 402.
Bujia, J. et al, Culture and Cryopreservation of Chondrocytes from Human Cartilage Relevance for Cartilage Allografting in Otolaryngology, ORL, 1992, pp. 80-84, vol. 54.
Bujia, J., Determination of the Viability of Crushed Cartilage Grafts: Clinical Implications for Wound Healing in Nasal Surgery, Ann Plast Surg, 1994, pp. 261-265, vol. 32.
Cherubino, P. et al, Autologous chondrocyte implantation using a bilayer collagen membrane: A preliminary report, J. Ortho Surg, 2003, pp. 10-15, vol. 11, No. 1.
Calandruccio, R. A. and Gilmer, W.S., Proliferation, Regeneration, and Repair of Articular Cartilage of Immature Animals, JBJS, 1962, pp. 431-455, vol. 44A, No. 3.
Chen, F.S. et al, Repair of Articular Cartilage Defects: Part II. Treatment Options, Am. J. Ortho, 1999, pp. 88-96.
Wagner, P.D. and Westen, E., et al, Improved blood buffering in high-altitude natives?, J Appl Physiol, 2002, pp. 2214-2215, vol. 93.
Wakitani, S., et al, Repair of Rabbit Articular Surfaces With Allograft Chondrocytes Embedded in Collagen Gel, JSJS, 1989, pp. 74-80, vol. 71-B.
Wei, X., et al, The Effect of Sodium Selenite on Chondrocytes in Monolayer Culture, Arthritis and Rheumatism, 1986, pp. 660-664, vol. 29, No. 5.
Welsh, F., The alar cartilage morseler: a new instrument, Br. J. Plastic Surgery, 1983, pp. 483-484, vol. 36.
Wilfilingseder, P., Cranioplasties by means of diced cartilage and split rib grafts, Min Chir, 1983, pp. 837-843, vol. 38, No. 12.
Wischhofer, E., et al, English abstract only of the Behaviour of Autologous Spongiosa Transplants from the Dial Crest With and Without Fibrinadhesive in the Canine Femoral Epiphysis, Unfallheilkunde, 1982, pp. 250-252, vol. 85.
Xu, J.W. et al, Injectable Tissue-Engineered Cartilage with Different Chondrocyte Sources, Plast. Reconstr. Surg., 2004, pp. 1361-1371, vol. 113.
Yamamoto, E. et al, Use of Micro-Sliced Homograft Cartilage Plates in Tympanoplasty, Acta Otolaryngol, 1985, pp. 123-129, vol. 419.
Yamashita, F. et al, The Transplantation of an Autogeneic Osteochondral Fragment for Osteochondritis Dissecans of the Knee, Clin Ortho Rel Res, 1985, pp. 43-50, vol. 201.

(56) References Cited

OTHER PUBLICATIONS

Yilmaz, S. et al, Viability of Diced, Crushed Cartilage Grafts and the Effects of Surgicel (Oxidized Regenerated Cellulose) on Cartilage Grafts, Plast. Reconstru. Surg. 2001, pp. 1054-1060, vol. 108.
Young, F., Autogenous Cartilage Grafts, An Experimental Study, Surgery, 1941, pp. 7-20, vol. 10.
Young, F., The use of autogenous rib cartilage grafts to repair surface defects in dog joints, Surgery, 1940, pp. 254-263, vol. 7.
Zahn, F., On the Fate of Tissues Implanted in the Organism, Int. Med. Congr. In Geneva, Biology Section—Meeting of Sep. 11, 1877, pp. 1-4.
Zalzal, G.H. et al, Cartilage Grafts-Present Status, Head and Neck Surgery, 1986, pp. 363-374, vol. 8.
Zilch, V.H. and Talke, M., Gluing Small Osteochondral Fragments with Fibrin Glue in Hand Surgery. Clinical Experiences, Handchirurgie, 1980, pp. 77-81, vol. 12.
Zilch, V.H., Animal Experiments Investigating the Fixation of Small Osteochondral Fragments by Means of Fibrin Glue, Handchirurgie, 1980, pp. 71-75, vol. 12.
Zilch, H. and Friedebold, G., English summary only of Fixing of Osteochondral Fragments with Fibrinogen Clue. Clinical Experiences, Akt. Traumatol., 1981, pp. 136, vol. 11.
Zilch, H. and Talke, M., English summary only of Fibrin sealant in cases of little osteochondral fragments of the upper limb, Ann. Chir. Main, 1987, pp. 173-176, vol. 6, No. 2.
Zilch, H. and Talke, M., English summary only of Fixation of Small Osteochondral Fragments with the Fibrinogen Adhesive, Clinical Report, Ann. Chir. Main, 1980, pp. 77-81, vol. 12.
Adkisson, H.D., IV et al, In Vitro Generation of Scaffold Independent Neocartilage, Clin Ortho Rel Res, 2001, pp. S280-S294, No. 391S.
Caruso, E. et al, Repopulation of Laser-Perforated Chondroepiphyseal Matrix with Xenogeneic Chondrocytes: An Experimental Model, JBJS, 1996, pp. 102-107, vol. 14.
Cheng, N.C. et al, Chondogenic Differentiation of Adipose-Derived Adult Stem Cells by a Porous Scaffold Derived from Native Articular Cartilage Extracellular Matrix, Tissue Engineering, Part A, 2009, pp. 231-241, vol. 15, No. 2.
Davis, J.S., Some of the Problems of Plastic Surgery, Ann Surg., 1917, pp. 88-94, vol. 66, No. 1.
Davis, W.B. and Gibson, T., Absorption of Autogenous Cartilage Grafts in Man, British Journal of Plastic Surgery, 1957, pp. 177-185, vol. 9.
Gelse, K. et al, Paracrine Effect of Transplanted Rib Chondrocyte Spheroids Supports Formation of Secondary Cartilage Repair Tissue, J. Ortho Res, 2009, pp. 1216-1225, vol. 27.
Hendrickson, D.A. et al, Chondrocyte-Fibrin Matrix Transplants for Resurfacing Extensive Articular Cartilage Defects, J. Ortho Res, 1994, pp. 485-497, vol. 12 No. 4.
Homminga, G.N. et al, Chondrocyte behavior in fibrin glue in vitro, Acta Orthop Scand, 1993, pp. 441-445, vol. 64, No. 4.
Howard, R.D., et al, Long-term fate and effects of exercise on sternal cartilage autografts used for repair of large osteochondral defects in horses, Am J Vet Res, 1994, pp. 1158-1167, vol. 55, No. 8.
Hutchinson, J., Observations on bone transplants in the anterior chamber of the eye, Glasgow Med J., 1949, pp. 357-363, vol. 30, No. 10.
Jeffries, D.J.R., and Evans, P.H.R., Cartilage regeneration following septal surgery in young rabbits, J. Laryngology and Otology, 1984, pp. 577-583, vol. 98.
Gu, J.D., et al, True Denisity of Normal and Enzymatically Treated Bovine Articular Cartilage, Trans Orthop Res Soc., 1999, pp. 642, vol. 24.
Kim, M.K. et al, Autologous chondrocyte implantation in the knee using fibrin, Knee Surg. Sports Traumatol. Arthrosc., 2010, pp. 528-534, vol. 18.
Libera, J., et al, Cartilage Engineering, Fundamentals of Tissue Engineering and Regenerative Medicine, 2009, pp. 233-242, Chapter 18, Springer-Verlag, Berlin Heidelberg.
Liu, X., et al, In vivo ectopic chondrogenesis of BMSCs directed by mature chondrocytes, Biomaterials, 2010, pp. 9406-9414, vol. 31.

Longacre, J.J. et al, Further observations of the behavior of autogenous split-rib grafts in reconstruction of extensive defects of the cranium and face, Plas Reconstr Surg, 1957, pp. 281-296, vol. 20, No. 4.
Marmotti, A., et al, One-Step osteochondral repair with cartilage fragments in a composite scaffold, Knee Surg Sports Traumatol Arthrosc., Feb. 21, 2012, [Epub ahead of print], 12 pages.
McKibbin B. and Holdsworth, F.W., The dual nature of epiphysial cartilage, J Bone Joint Surg Br., 1967, pp. 351-361, vol. 49, No. 2.
Medawar, P.B., Immunity to homologous grafted skin; the fate of skin homografts transplanted to the brain, to subcutaneous tissue, and to the anterior chamber of the eye, Br J Exp Pathol., 1948, pp. 58-69, vol. 29, No. 1.
Munirah, S. et al, Articular cartilage restoration in load-bearing osteochondral defects by implantation of autologous chondrocyte-fibrin constructs: an experimental study in sheep, J Bone Joint Surg Br., 2007, pp. 1099-1109, vol. 89, No. 8.
Nehrer, S. et al, Three-year clinical outcome after chondrocyte transplantation using a hyaluronan matrix for cartilage repair, Eur J Radiol., 2006, pp. 3-8, vol. 57, No. 1.
Obradovic, B., et al, Integration of engineered cartilage, J Orthop Res., 2001, pp. 1089-1097, vol. 19, No. 6.
Verwoerd, C.D.A. et al, Stress and woundhealing of the cartilaginous nasal septum, Acta Otolaryngol., 1989, pp. 441-445, vol. 107, Nos. 5-6.
Pierce, A. et al, Surgicel: macrophage processing of the fibrous component, Int J Oral Maxillofac Surg., 1987, pp. 338-445, vol. 16, No. 3.
Roemhildt, M.L. et al, Material properties of articular cartilage in the rabbit tibial plateau, J. Biomech, 2006, pp. 2331-2337, vol. 39, No. 12.
Schubert, T. et al, Long-term effects of chondrospheres on cartilage lesions in an autologous chondrocyte implantation model as investigated in the SCID mouse model, International Journal of Molecular Medicine, 2009, pp. 455-460, vol. 23.
Selktar, D., Lecture Bulletin Nature's Healing Matrix, Technion Focus, May 2006, 1 page.
Silverman, R.P., et al, Adhesion of Tissue-Engineered Cartilage to Native Cartilage, Plast. Reconstr Surg, 2000, pp. 1393-1398, vol. 105.
Sin, Y.M. et al, Studies on the mechanism of cartilage degradation, J Pathol., 1984, pp. 23-30, vol. 142, No. 1.
Van Susante, J.L.C. et al, Resurfacing potential of heterologous chondrocytes suspended in fibrin glue in large full-thickness defects of femoral articular cartilage: an experimental study in the goat, Biomaterials, 1999, pp. 1167-1175, vol. 20, No. 13.
Egkher, E., Indications and Limits of Fibrin Adhesive Applied to Traumatological Patients, Traumatology and Orthopaedics, 1986, pp. 144-151, vol. 7, Springer-Verlag, Berlin Heidelberg.
Erikson, U. et al, English abstract only, A roentgenological method for the determination of renal blood flow. A preliminary report, Acta Soc Med Ups, 1965, pp. 213-6, vol. 70, No. 3.
Erol, O.O., The Turkish Delight: A Pliable Graft for Rhinoplasty, Plast. Reconstr. Surg., 2000, pp. 2229-2241, vol. 105.
Evans, C.H., et al, Experimental Arthritis Induced by Intraarticular Injection of Allogenic Cartilageinous Particles into Rabbit Knees, Arthritis and Rheumatism, 1984, pp. 200-207, vol. 27, No. 2.
Farrior, R.T., Implant Materials in Restoration of Facial Contour, Laryngoscope, 1966, pp. 934-954, vol. 76, No. 5.
Feldman, M.D., et al, Compatibility of Autologous Fibrin Adhesive With Implant Materials, Arch Otolaryngol Head Neck Surg, 1988, pp. 182-185, vol. 114.
Fontana, A., et al, Cartilage Chips Synthesized with Fibrin Glue in Rhinoplasty, Aesth Plast Surg, 1991, pp. 237-240, vol. 15.
Furukawa, T. et al, Biochemical Studies on Repair Cartilage Resurfacing Experimental Defects in the Rabbit Knee, J Bone Joint Surg Am, 1980, pp. 79-89, vol. 62, No. 1.
Gaudernak, T., et al, Clinical Experiences Using Fibrin Sealant in the Treatment of Osteochondral Fractures, Fibrin Sealant in Operative Medicine-Traumatology and Orthopaedics, 1986, pp. 91-102, vol. 7, Springer-Verlag, Berlin Heidelberg.

(56) References Cited

OTHER PUBLICATIONS

Gerngross, H. et al, Experimental Studies on the Influence of Fibrin Adhesive, Factor XIII, and Calcitonin on the Incorporation and Remodeling of Autologous Bone Grafts, Arch Orthop Trauma Surg, 1986, pp. 23, 31, vol. 106.
Gersdorff, M.C.H., and Robillard, T.A., "How I Do It"—Otology and Neurotology. A Specific Issue and Its Solution. A New Procedure for Bone Reconstruction in Oto-Microsurgery: A Mixture of Bone Dust and Fibrinogen Adhesive, Laryngoscope, 1985, pp. 1278-1280, vol. 95.
Ghadially, J.A. and Ghadially, F.N., Evidence of Cartilage Flow in Deep Defects in Articular Cartilage, Virchows Arch B. Cell Path, 1975, pp. 193-204, vol. 18.
Ghadially, J.A. et al, Long-Term Results of Deep Defects in Articular Cartilage, Virchows Arch B. Cell Path, 1977, pp. 125-136, vol. 25.
Ghazavi, M.T. et al, Fresh Osteochondral Allografts for Post-Traumatic Osteochondral Defects of the Knee, JBJS, 1997, pp. 1008-1013, vol. 79-B.
Gibson, T. et al, The Long-Term Survival of Cartilage Homografts in Man, British Journal of Plastic Surgery, 1958, pp. 177-187, vol. 11.
Gooding, C.R. et al, Abstract only of a prospective, randomised study comparing two techniques of autologous chondrocyte implantation for osteochondral defects in the knee: Periosteum covered versus type I/III collagen covered, Knee, 2006, pp. 203-210, vol. 13, No. 3.
Greco, F. et al, Experimental Investigation into Reparative Osteogenesis With Fibrin Adhesive, Arch Orthop Trauma Surg, 1988, pp. 99-104, vol. 107.
Hamra, S.T., Crushed Cartilage Grafts over Alar Dome Reduction in Open Rhinoplasty, Plast Reconstr Surg., 1993, pp. 352-356, vol. 92, No. 2.
Hangody, L. et al, English Abstract only, Autogenous Osteochondralf Craft Technique for Replacing Knee Cartilage Defects in Dogs, Autogenous Osteochondral Mosaicplasty, Orthop Int, 1997, pp. 175-181, vol. 5, No. 3.
Hangody, L. and Fules, P., Autologous Osteochondral Mosaicplasty for the Treatment of Full-Thickness Defects of Weght-Bearing Joints: Ten Years of Experimental and clinical Experience, JBJS, 2003, pp. 25-32, vol. 85.
Hangody, L. et al, Mosaicplasty for the Treatment of Articular Defects of the Knee and Ankle, Clin Orthopaedics and Rel Res, 2001, pp. S328-S336, No. 391S.
Harbin, M. and Moritz, A.R., Autogenous Free Cartilage Transplanted into Joints, Archives of Surgery, 1930, pp. 885-896, vol. 20, No. 6.
He, Q. et al, Repair of flexor tendon defects of rabbit with tissue engineering method, Chinese Journal of Traumatology, 2002, pp. 200-208, vol. 5, No. 4.
Helidonis, E. et al, Laser Shaping of Composite Cartilage Grafts, Am. J. Otolaryngology, 1993, pp. 410-412, vol. 14, No. 6.
Homminga, G.N. et al, Perichondral Grafting for Cartilage Lesions of the Knee, British Editorial Society of Bone and Joint Surgery, 1990, pp. 1003-1007, vol. 72B.
Homminga, G.N., Repair of Chrondral Lesions of the Knee with a Perichondrial Graft, Fibrin Sealant in Operative Medicine-Orthopedic Surgery Maxillofacial Surgery, 1986, pp. 61-69, vol. 4, Springer-Verlag, Berlin Heidelberg.
Hoover, N.W. et al, Skin Arthroplasty of the Hip, An Experimental Study in Dogs, JBJS, 1961, pp. 1155-1166, vol. 43-A, No. 8.
Horas, U. et al, Autologous Chondrocyte Implantation and Osteochondral Cylinder Transplantation in Cartilage Repair of the Knee Joint: A Prospective, Comparative Trial, JBJS, 2003, pp. 185-192, vol. 85.
Horton, W.A. et al, Characterization of a type II collagen gene (COL2A1) mutation identified in cultured chondrocytes from human hypochondrogenesis, PNAS, 1992, pp. 4583-4587, vol. 89.
Hunziker, E.B., Articular cartilage repair: basic science and clinical progress. A review of the current status and prospects, Osteoarthritis and Cartilage, 2001, pp. 432-463, vol. 10.
Hurtig, M.B. et al, Effects of Lesion Size and Location on Equine Articular Cartilage Repair, Can J. Vet Res, 1988, pp. 137-146, vol. 52.
Hurtig, M.B., Use of autogenous cartilage particles to create a model of naturally occurring degenerative joint disease in the horse, Equine Vet J Suppl, 1988, pp. 19-22, No. 6.
Imhoff, A.B., et al, English Abstract only of Autologous Osteochondral transplantation on various joints, Orthopade, 1999, pp. 33-44, vol. 28, No. 1.
Ishida, T., English Abstract only of the Use of a Fibrin Adhesive for a Cartilage Graft Basic and Clinical Studies, Japanese J. of Plastic and Reconstructive Surgery, 1990, pp. 215-230, vol. 33, No. 1.
Ishizaki, Y. et al, Autocrine Signals Enable Chondrocytes to Survive in Culture, J. Cell Biol. 1994, pp. 1069-1077, vol. 126, No. 4.
Ito, Y. et al, Localization of chondrocyte precursors in periosteum, Osteoarthritis and Cartilage, 2001, pp. 215-223, vol. 9.
Ittner, G. et al, English Abstract only of Treatment of flake fracture of the talus, Z. Orthop Ihre Grenzgeb, 1989, pp. 183-186, vol. 127, No. 2.
Jakob, R.P. et al, Autologous Osteochondral Grafting in the Knee: Indication, Results and Reflections, Clinical Orthopaedics and Rel Res, 2002, pp. 170.184, No. 401.
Jin, C.Z. et al, Human Amniotic Membrane as a Delivery Matrix for Articular Cartilage Repair, Tissue Engineering, 2007, pp. 693-702, vol. 13, No. 4.
Johnson, L.L., Arthroscopic Abrasion Arthroplasty Historical and Pathologic Perspective: Present Status, Arthroscopy: The Journal of Arthroscopic and Related Surgery, 1986, pp. 54-69, vol. 2, No. 1.
Kanzaki, J. et al, Use of Fibrin Glue in Intracranial Procedures Following Acoustic Neuroma Surgery: Application in Facial Nerve Reconstruction and Prevention of Cerebrospinal Fluid Rhinorrhea, Fibrin Sealing in Surgical and Nonsurgical Fields-Neurosurgery Ophthalmic Surgery Ent, 1994, pp. 162-168, vol. 5, Springer-Verlag, Berlin Heidelberg.
Kaplonyi, G. et al, The use of fibrin adhesive in the repair of chondral and osteochondral injuries, Injury, 1988, pp. 267-272, vol. 19.
Kawamura, M. and Urist, M.R., Human Fibrin Is a Physiologic Delivery System for Bone Morphogenetic Protein, Clin Ortho Rel Res, 1988, pp. 302-310, No. 235.
Keller, J. et al, Fixation of osteochondral fractures, Acta Orthop Scand, 1985, pp. 323-326, vol. 56.
Kettunen, K.O., Skin Arthroplasty in the Light of Animal Experiments With Special Reference to Functional Metaplasia of Connective Tissue, Acta Ortho Scand, 1958, pp. 9-69, Suppl. XXIX.
Kirilak, Y. et al, Fibrin sealant promotes migration and proliferation of human articular chondrocytes: possible involvement of thrombin and protease-activated receptors, Int. J. Mol. Med, 2006, pp. 551-558, vol. 17, No. 4.
Knutsen, G. et al, Autologous Chondrocyte Implantation Compared with Microfracture in the Knee. A Randomized Trial, JBJS, 2004, pp. 455-464, vol. 86.
Kon, E. et al, Second Generation Issues in Cartilage Repair, Sports Med Arthrosc Rev., 2008, pp. 221-229, vol. 16.
Korhonen, R.K. et al, Importance of the superficial tissue layer for the indentation stiffness of articular cartilage, Medical Eng. Phys, 2002, pp. 99-108, vol. 24.
Lane, J.M. et al, Joint Resurfacing in the Rabbit Using an Autologous Osteochondral Graft, JBJS, 1977, pp. 218-222, vol. 59-A, No. 2.
"U.S. Appl. No. 11/613,319, Non Final Office Action mailed Jun. 19, 2014", 12 pgs.
"U.S. Appl. No. 12/861,404, Notice of Allowance mailed Feb. 13, 2014", 7 pgs.
"U.S. Appl. No. 12/976,689, Notice of Allowance mailed Mar. 25, 2014", 5 pgs.
"U.S. Appl. No. 12/976,704, Notice of Allowance mailed Feb. 6, 2014", 8 pgs.
"U.S. Appl. No. 12/976,704, Supplemental Notice of Allowability mailed Apr. 14, 2014", 4 pgs.
"U.S. Appl. No. 13/799,452, Non Final Office Action mailed May 21, 2014", 11 pgs.
"U.S. Appl. No. 13/951,762, Examiner Interview Summary mailed Apr. 16, 2014", 3 pgs.
"U.S. Appl. No. 13/951,762, Final Office Action mailed Mar. 14, 2014", 7 pgs.
"U.S. Appl. No. 13/951,762, Non Final Office Action mailed Jun. 9, 2014", 5 pgs.

(56) References Cited

OTHER PUBLICATIONS

"U.S. Appl. No. 13/951,762, Response filed May 14, 2014 to Final Office Action dated Mar. 14, 2014", 10 pgs.
"U.S. Appl. No. 14/299,314, Preliminary Amendment mailed Jun. 10, 2014", 4 pgs.
"Canadian Application Serial No. 2,684,040, Office Action mailed Mar. 3, 2014", 3 pgs.
"International Application Serial No. PCT/US2004/041591, International Search Report and Written Opinion mailed May 18, 2005", 4 pgs.
"International Application Serial No. PCT/US2008/060078, International Preliminary Report on Patentability mailed Oct. 13, 2009", 9 pgs.
"U.S. Appl. No. 12/063,291, Notice of Allowance mailed Mar. 4, 2013", 7 pgs.
"U.S. Appl. No. 12/101,553, Response filed Mar. 13, 2013 to Final Office Action mailed Dec. 28, 2012", 15 pgs.
"U.S. Appl. No. 12/861,404, Final Office Action mailed Dec. 6, 2013", 7 pgs.
"U.S. Appl. No. 12/861,404, Response filed Jan. 10, 2014 to Final Office Action dated Dec. 6, 2013", 6 pgs.
"U.S. Appl. No. 12/861,404, Response filed Apr. 1, 2013 to Non Final Office Action mailed May 16, 2012", 6 pgs.
"U.S. Appl. No. 12/976,689, Response filed Apr. 1, 2013 to Non Final Office Action mailed May 17, 2012", 7 pgs.
"U.S. Appl. No. 12/976,704, Non Final Office Action mailed Sep. 12, 2013", 10 pgs.
"U.S. Appl. No. 12/976,704, Response filed Dec. 10, 2013 to Non-Final Office Action dated Sep. 12, 2013", 7 pgs.
"U.S. Appl. No. 12/976,711, Examiner Interview Summary mailed Apr. 8, 2013", 3 pgs.
"U.S. Appl. No. 12/976,711, Examiner Interview Summary mailed Jul. 25, 2013", 3 pgs.
"U.S. Appl. No. 12/976,711, Final Office Action mailed Apr. 17, 2013", 6 pgs.
"U.S. Appl. No. 12/976,711, Non Final Office Action mailed Aug. 1, 2013", 5 pgs.
"U.S. Appl. No. 12/976,711, Notice of Allowance mailed Aug. 23, 2013", 6 pgs.
"U.S. Appl. No. 12/976,711, Response filed Apr. 2, 2013 to Non Final Office Action mailed Dec. 12, 2012", 8 pgs.
"U.S. Appl. No. 12/976,711, Response filed Jul. 22, 2013 to Final Office Action mailed Apr. 17, 2013", 6 pgs.
"U.S. Appl. No. 12/976,711, Response filed Aug. 9, 2013 to Non Final Office Action mailed Aug. 1, 2013", 6 pgs.
"U.S. Appl. No. 12/976,711, Supplemental Notice of Allowability mailed Nov. 21, 2013", 2 pgs.
"U.S. Appl. No. 12/976,711, Supplemental Notice of Allowability mailed Dec. 20, 2013", 2 pgs.
"U.S. Appl. No. 13/327,238, Notice of Allowance mailed Apr. 30, 2013", 6 pgs.
"U.S. Appl. No. 13/327,238, Response filed Apr. 2, 2013 to Non Final Office Action mailed Apr. 2, 2013", 6 pgs.
"U.S. Appl. No. 13/327,286, Non Final Office Action mailed Feb. 7, 2013", 9 pgs.
"U.S. Appl. No. 13/327,286, Notice of Allowance mailed Apr. 24, 2013", 6 pgs.
"U.S. Appl. No. 13/327,286, Response filed Apr. 2, 2013 to Non Final Office Action mailed Feb. 7, 2013", 6 pgs.
"U.S. Appl. No. 13/327,286, Supplemental Notice of Allowability mailed May 15, 2013", 2 pgs.
"U.S. Appl. No. 13/327,286, Supplemental Notice of Allowability mailed May 28, 2013", 4 pgs.
"U.S. Appl. No. 13/428,873, Notice of Allowance mailed Mar. 25, 2013", 6 pgs.
"U.S. Appl. No. 13/428,873, Response filed Feb. 12, 2013 to Final Office Action mailed Dec. 12, 2012", 6 pgs.
"U.S. Appl. No. 13/799,452, Response filed Jan. 28, 2014 to Restriction Requirement mailed Dec. 24, 2013", 5 pgs.

"U.S. Appl. No. 13/799,452, Restriction Requirement mailed Dec. 24, 2013", 9 pgs.
"U.S. Appl. No. 13/951,762, Non Final Office Action mailed Sep. 20, 2013", 10 pgs.
"U.S. Appl. No. 13/951,762, Preliminary Amendment filed Jul. 26, 2013", 3 pgs.
"U.S. Appl. No. 13/951,762, Response filed Jan. 21, 2014 to Non-Final office Action dated Sep. 20, 2013", 8 pgs.
"U.S. Appl. No. 13/951,762, Supplemental Preliminary Amendment filed Aug. 22, 2013", 4 pgs.
"Australian Application Serial No. 2006282754, Response filed May 7, 2013 to First AU Examiner Report mailed Nov. 8, 2011", 13 pgs.
"Australian Application Serial No. 2006282754, Subsequent Examiners Report mailed Jun. 14, 2013", 3 pgs.
"Australian Application Serial No. 2008240191, Response filed Aug. 22, 2013 to First Examination Report mailed Sep. 21, 2012", 12 pgs.
"Canadian Application Serial No. 2,684,040, Office Action mailed May 13, 2013", 4 pgs.
"Canadian Application Serial No. 2,684,040, Response filed Oct. 29, 2013 to Office Action mailed May 13, 2013", 20 pgs.
"European Application Serial No. 04813849.9, Office Action mailed Jun. 10, 2011", 3 pgs.
"European Application Serial No. 04813849.9, Office Action mailed Jul. 21, 2006", 2 pgs.
"European Application Serial No. 04813849.9, Office Action mailed Dec. 30, 2010", 4 pgs.
"European Application Serial No. 04813849.9, Response filed Aug. 21, 2006 to Office Action mailed Jul. 21, 2006", 4 pgs.
"European Application Serial No. 08745639.8, Extended European Search Report mailed Apr. 3, 2013", 7 pgs.
"European Application Serial No. 08745639.8, Response filed Oct. 18, 2013 to Extended European Search Report mailed Apr. 3, 2013", 9 pgs.
"European Application Serial No. 11154746.9, Office Action mailed Jan. 7, 2013", 3 pgs.
"European Application Serial No. 11154746.9, Office Action mailed Mar. 5, 2012", 33 pgs.
"European Application Serial No. 11154746.9, Office Action mailed Nov. 15, 2012", 1 pg.
"European Application Serial No. 11154746.9, Response filed Jul. 5, 2012 to Office Action mailed Mar. 5, 2012", 7 pgs.
"European Application Serial No. 11154747.7, Office Action mailed Mar. 5, 2012", 4 pgs.
"European Application Serial No. 11154747.7, Office Action mailed Jul. 23, 2012", 3 pgs.
"European Application Serial No. 11154747.7, Office Action mailed Nov. 21, 2012", 4 pgs.
"European Application Serial No. 11154747.7, Response filed Jun. 25, 2012 to Office Action mailed Mar. 5, 2012", 8 pgs.
"European Application Serial No. 11154747.7, Response filed Sep. 5, 2012 to Office Action mailed Jul. 23, 2012", 3 pgs.
"European Application Serial No. 11154747.7, Response filed Dec. 13, 2011 to Extended European Search Report mailed May 23, 2011", 3 pgs.
"European Application Serial No. 11154748.5, Office Action mailed Apr. 13, 2012", 5 pgs.
"International Application Serial No. PCT/US2008/60078, International Search Report mailed Sep. 3, 2008", 3 pgs.
"NPL text search results cited by USPTO in U.S. Appl. No. 13/951,762", (Sep. 17, 2013), 1 pg.
Adibi, Siamak A, et al., "Removal of Glycylglutamine from Plasma by Individual Tissues: Mechanism and Impact on Amino Acid Fluxes in Postabsorption and Starvation", The Journal of Nutrition, Symposium: Nutritional and Hormonal Regulation of Amino Acid Metabolism, (1993), 325-331.
Brighton, Carl T, et al., "In Vitro Rabbit Articular Cartilage Organ Model II. 35S Incorporation in Various Oxygen Tensions", Arthritis and Rheumatism vol. 17, No. 3, (May 1974), 245-252.
Butler, M, et al., "Nutritional aspects of the growth of animal cells in culture", Journal of Biotechnology 12, (1989), 97-110.
Butler, Michael, et al., "Adaptation of mammalian cells to non-ammoniagenic media", Cytotechnology 15, (1994), 87-94.

(56) References Cited

OTHER PUBLICATIONS

Chesterman, P. J, et al., "Cartilage as a Homograft", The Journal of Bone and Joint Surgery. Proceedings and reports of councils and associations, (1968), 878.
Christie, A, et al., "Glutamine-based dipeptides are unilized in mammalian cell culture by extracellular hydrolysis catalyzed by a specific peptidase", Journal of Biotechnology 37, (1994), 277-290.
Frisbie, David D, et al., "In Vivo Evaluation of Autologous Cartilage Fragment-Loaded Scaffolds Implanted Into Equine Articular Defects and Compared With Autologous Chondrocyte Implantation", The American Journal of Sports Medicine 37, (Nov. 24, 2009), 71S-80S.
Glacken, Michael W, "Catabolic Control of Mammalian Cell Culture", Biotechnology vol. 6, (Sep. 1998), 1041-1050.
Hammarqvist, Folke, et al., "Alanyl-glutamine Counteracts the Depletion of Free Glutamine and the Postoperative Decline in Protein Synthesis in Skeletal Muscle", Ann. Surg, (Nov. 1990), 637-644.
Hassell, T, et al., "Growth Inhibition in Animal Cell Culture: The Effect of Lactate and Ammonia", Applied Biochemistry and Biotechnology, vol. 30, (1991), 29-41.
McCormick, F., "Minced Articular Cartilage—Basic Science, Surgical Technique, and Clinical Application", Sports Med. Arthrosc. Rev., vol. 16, No. 4, (Dec. 2008), 217-220.
McIlwraith, C W, et al., "In-Vivo Evaluation of a One-Step Autologous Cartilage Resurfacing Technique (CAIS)—Comparison of Three Different Scaffolds", 6th Symposium of the International Cartilage Repair Society, (Jan. 2006), p. 3-6.
Minamoto, Yoshiki, et al., "Development of a serum-free and heat-sterilizable medium and continuous high-density cell culture", Cytotechnology, vol. 5, (1991), S35-S51.
Newland, M, et al., "Hybridoma growth limitations: The roles of energy metabolism and ammonia production", Cytotechnology, vol. 3, (1990), 215-229.
Reitzer, Lawrence J, et al., "Evidence that Glutamine, Not Sugar, is the Major Energy Source for Cultured HeLa Cells", The Journal of Biological Chemistry, vol. 254, No. 8, (Apr. 1979), 2669-2676.
Roth, E, et al., "Influence of Two Glutamine-Containing Dipeptides on Growth of Mammalian Cells", In Vitro Cellular & Developmental Biology, vol. 24, No. 7, (Jul. 1988), 696-698.
Zielke, Ronald H, et al., "Glutamine: a major energy source for mammalian cells", Federation Proceedings, vol. 43, No. 1, (Jan. 1984), 121-125.
"U.S. Appl. No. 12/101,553, Non Final Office Action mailed Nov. 19, 2014", 8 pgs.
"U.S. Appl. No. 13/951,762, Final Office Action mailed Nov. 12, 2014", 6 pgs.
"U.S. Appl. No. 13/951,762, Response filed Sep. 9, 2014 to Non-Final Office Action mailed Jun. 9, 2014", 12 pgs.
"European Application Serial No. 08745639.8, Examination Notification Art. 94(3) mailed Oct. 24, 2014", 4 pgs.
"U.S. Appl. No. 10/374,772, 1.132 Declaration of Julia Hwang filed Jan. 5, 2009", 3 pgs.
"U.S. Appl. No. 10/374,772, Response filed Jan. 6, 2009 to Non-Final Office Action mailed Sep. 2, 2008", 5 pgs.
"U.S. Appl. No. 10/874,402, Final Office Action mailed Feb. 22, 2011", 10 pgs.
"U.S. Appl. No. 10/874,402, Final Office Action mailed Apr. 17, 2009", 17 pgs.
"U.S. Appl. No. 10/874,402, Final Office Action mailed Apr. 19, 2010", 13 pgs.
"U.S. Appl. No. 10/874,402, Non Final Office Action mailed Apr. 10, 2008", 9 pgs.
"U.S. Appl. No. 10/874,402, Non Final Office Action mailed Sep. 22, 2010", 11 pgs.
"U.S. Appl. No. 10/874,402, Non Final Office Action mailed Oct. 27, 2009", 15 pgs.
"U.S. Appl. No. 11/010,779, Examiner Interview Summary mailed Apr. 5, 2010", 4 pgs.
"U.S. Appl. No. 11/010,779, Examiner Interview Summary mailed Dec. 7, 2009", 3 pgs.
"U.S. Appl. No. 11/010,779, Non Final Office Action mailed Feb. 7, 2010", 4 pgs.
"U.S. Appl. No. 11/010,779, Non Final Office Action mailed Apr. 15, 2009", 8 pgs.
"U.S. Appl. No. 11/010,779, Notice of Allowance mailed Jul. 8, 2010", 4 pgs.
"U.S. Appl. No. 11/010,779, Response filed Feb. 12, 2009 to Restriction Requirement mailed Jan. 12, 2009", 3 pgs.
"U.S. Appl. No. 11/010,779, Response filed Apr. 19, 2010 to Non Final Office Action mailed Feb. 17, 2010", 13 pgs.
"U.S. Appl. No. 11/010,779, Response filed Jul. 15, 2009 to Non Final Office Action mailed Apr. 15, 2009", 16 pgs.
"U.S. Appl. No. 11/010,779, Response filed Dec. 3, 2009 to Non Final Office Action mailed Apr. 15, 2009", 13 pgs.
"U.S. Appl. No. 11/010,779, Restriction Requirement mailed Jan. 12, 2009", 16 pgs.
"U.S. Appl. No. 11/413,419, Final Office Action mailed Aug. 25, 2009", 13 pgs.
"U.S. Appl. No. 11/413,419, Non Final Office Action mailed Jun. 26, 2008", 12 pgs.
"U.S. Appl. No. 11/613,250, Advisory Action mailed Jul. 9, 2008", 13 pgs.
"U.S. Appl. No. 11/613,250, Final Office Action mailed Apr. 15, 2008", 9 pgs.
"U.S. Appl. No. 11/613,250, Non Final Office Action mailed Mar. 28, 2011", 9 pgs.
"U.S. Appl. No. 11/613,250, Non Final Office Action mailed May 28, 2009", 12 pgs.
"U.S. Appl. No. 11/613,250, Non Final Office Action mailed Sep. 20, 2007", 17 pgs.
"U.S. Appl. No. 11/613,250, Non Final Office Action mailed Sep. 21, 2010", 15 pgs.
"U.S. Appl. No. 11/613,250, Non Final Office Action mailed Oct. 16, 2008", 11 pgs.
"U.S. Appl. No. 11/613,250, Non Final Office Action mailed Dec. 23, 2009", 15 pgs.
"U.S. Appl. No. 11/613,250, Notice of Allowance mailed Dec. 23, 2011", 9 pgs.
"U.S. Appl. No. 11/613,250, Response filed Jan. 16, 2009 to Non Final Office Action mailed Oct. 16, 2008", 9 pgs.
"U.S. Appl. No. 11/613,250, Response filed Jan. 19, 2011 to Non Final Office Action mailed Sep. 21, 2010", 13 pgs.
"U.S. Appl. No. 11/613,250, Response filed Mar. 23, 2010 to Non Final Office Action mailed Dec. 23, 2009", 9 pgs.
"U.S. Appl. No. 11/613,250, Response filed Jun. 16, 2008 to Final Office Action mailed Apr. 15, 2008", 19 pgs.
"U.S. Appl. No. 11/613,250, Response filed Aug. 28, 2009 to Non Final Office Action mailed May 28, 2009", 12 pgs.
"U.S. Appl. No. 11/613,250, Response filed Sep. 28, 2011 to Non Final Office Action mailed Mar. 28, 2011", 9 pgs.
"U.S. Appl. No. 11/613,250, Response filed Dec. 20, 2007 to Non Final Office Action mailed Sep. 20, 2007", 19 pgs.
"U.S. Appl. No. 11/613,319, Advisory Action mailed Jan. 19, 2010", 3 pgs.
"U.S. Appl. No. 11/613,319, Final Office Action mailed Jun. 18, 2012", 11 pgs.
"U.S. Appl. No. 11/613,319, Final Office Action mailed Oct. 26, 2009", 7 pgs.
"U.S. Appl. No. 11/613,319, Information Disclosure Statement mailed Mar. 20, 2007", 9 pgs.
"U.S. Appl. No. 11/613,319, Information Disclosure Statement mailed Jun. 30, 2008", 6 pgs.
"U.S. Appl. No. 11/613,319, Information Disclosure Statement mailed Sep. 3, 2010", 5 pgs.
"U.S. Appl. No. 11/613,319, Information Disclosure Statement mailed Dec. 20, 2007", 6 pgs.
"U.S. Appl. No. 11/613,319, Non Final Office Action mailed Mar. 13, 2009", 7 pgs.
"U.S. Appl. No. 11/613,319, Non Final Office Action mailed Dec. 29, 2011", 9 pgs.
"U.S. Appl. No. 11/613,319, Response filed Jan. 26, 2009 to Restriction Requirement mailed Dec. 26, 2008", 7 pgs.

(56) References Cited

OTHER PUBLICATIONS

"U.S. Appl. No. 11/613,319, Response filed Jan. 26, 2010 to Advisory Action mailed Jan. 19, 2010", 9 pgs.
"U.S. Appl. No. 11/613,319, Response filed Mar. 29, 2012 to Non Final Office Action mailed Dec. 29, 2011", 15 pgs.
"U.S. Appl. No. 11/613,319, Response filed Jun. 11, 2009 to Non Final Office Action mailed Mar. 13, 2009", 8 pgs.
"U.S. Appl. No. 11/613,319, Response filed Sep. 17, 2012 to Final Office Action mailed Jun. 18, 2012", 19 pgs.
"U.S. Appl. No. 11/613,319, Response filed Dec. 7, 2009 to Final Office Action mailed Oct. 26, 2009", 8 pgs.
"U.S. Appl. No. 11/613,319, Restriction Requirement mailed Dec. 26, 2008", 6 pgs.
"U.S. Appl. No. 11/613,456, Advisory Action mailed Aug. 11, 2009", 3 pgs.
"U.S. Appl. No. 11/613,456, Final Office Action mailed Jun. 4, 2009", 7 pgs.
"U.S. Appl. No. 11/613,456, Non Final Office Action mailed Jan. 23, 2009", 6 pgs.
"U.S. Appl. No. 11/613,456, Non Final Office Action mailed Sep. 11, 2009", 5 pgs.
"U.S. Appl. No. 11/613,456, Notice of Allowance mailed Jan. 19, 2010", 5 pgs.
"U.S. Appl. No. 11/613,456, Response filed Apr. 3, 2009 to Non Final Office Action mailed Jan. 23, 2009", 8 pgs.
"U.S. Appl. No. 11/613,456, Response filed Aug. 4, 2009 to Final Office Action mailed Jun. 4, 2009", 9 pgs.
"U.S. Appl. No. 11/613,456, Response filed Nov. 6, 2008 to Restriction Requirement mailed Oct. 7, 2008", 7 pgs.
"U.S. Appl. No. 11/613,456, Response filed Dec. 7, 2009 to Non Final Office Action mailed Sep. 11, 2009", 9 pgs.
"U.S. Appl. No. 11/613,456, Restriction Requirement mailed Oct. 7, 2008", 6 pgs.
"U.S. Appl. No. 12/063,291, Final Office Action mailed Mar. 15, 2012", 10 pgs.
"U.S. Appl. No. 12/063,291, Final Office Action mailed Mar. 22, 2011", 8 pgs.
"U.S. Appl. No. 12/063,291, Non Final Office Action mailed Sep. 15, 2010", 6 pgs.
"U.S. Appl. No. 12/063,291, Notice of Allowance mailed Aug. 8, 2012", 9 pgs.
"U.S. Appl. No. 12/063,291, Notice of Allowance mailed Oct. 11, 2012", 8 pgs.
"U.S. Appl. No. 12/063,291, Preliminary Amendment filed Feb. 8, 2008", 9 pgs.
"U.S. Appl. No. 12/063,291, Response filed Jan. 21, 2011 to Non Final Office Action mailed Sep. 15, 2010", 12 pgs.
"U.S. Appl. No. 12/063,291, Response filed Jul. 16, 2012 to Final Office Action mailed Mar. 15, 2012", 13 pgs.
"U.S. Appl. No. 12/063,291, Response filed Sep. 22, 2011 to Final Office Action mailed Mar. 22, 2011", 10 pgs.
"U.S. Appl. No. 12/101,553, Response filed Aug. 15, 2011 to Restriction Requirement mailed Jul. 13, 2011", 11 pgs.
"U.S. Appl. No. 12/101,553, Final Office Action mailed Sep. 14, 2012", 9 pgs.
"U.S. Appl. No. 12/101,553, Final Office Action mailed Dec. 28, 2012", 9 pgs.
"U.S. Appl. No. 12/101,553, Non Final Office Action mailed Nov. 9, 2011", 8 pgs.
"U.S. Appl. No. 12/101,553, Response filed May 9, 2012 to Non Final Office Action mailed Nov. 9, 2011", 14 pgs.
"U.S. Appl. No. 12/101,553, Restriction Requirement mailed Jul. 13, 2011", 17 pgs.
"U.S. Appl. No. 12/751,230, Non Final Office Action mailed Sep. 1, 2010", 9 pgs.
"U.S. Appl. No. 12/751,230, Preliminary Amendment filed Mar. 31, 2010", 7 pgs.
"U.S. Appl. No. 12/751,230, Response filed Jul. 30, 2010 to Restriction Requirement mailed Jul. 21, 2010", 5 pgs.
"U.S. Appl. No. 12/751,230, Restriction Requirement mailed Jul. 21, 2010", 53 pgs.
"U.S. Appl. No. 12/861,404, Non Final Office Action mailed May 16, 2012", 6 pgs.
"U.S. Appl. No. 12/861,404, Preliminary Amendment filed Aug. 23, 2010", 6 pgs.
"U.S. Appl. No. 12/976,689, Non Final Office Action mailed May 17, 2012", 7 pgs.
"U.S. Appl. No. 12/976,711, Examiner Interview Summary mailed Nov. 15, 2012", 3 pgs.
"U.S. Appl. No. 12/976,711, Non Final Office Action mailed Dec. 12, 2012", 9 pgs.
"U.S. Appl. No. 12/976,711, Response filed Aug. 29, 2012 to Restriction Requirement mailed May 29, 2012", 4 pgs.
"U.S. Appl. No. 12/976,711, Response filed Dec. 3, 2012 to Restriction Requirement mailed Oct. 4, 2012", 6 pgs.
"U.S. Appl. No. 12/976,711. Restriction Requirement mailed May 29, 2012", 6 pgs.
"U.S. Appl. No. 12/976,711. Restriction Requirement mailed Oct. 4, 2012", 6 pgs.
"U.S. Appl. No. 13/327,238, Non Final Office Action mailed Jan. 2, 2013", 8 pgs.
"U.S. Appl. No. 13/327,238, Preliminary Amendment filed Jun. 1, 2012", 6 pgs.
"U.S. Appl. No. 13/327,238, Response filed Dec. 7, 2012 to Restriction Requirement mailed Sep. 7, 2012", 6 pgs.
"U.S. Appl. No. 13/327,238, Restriction Requirement mailed Sep. 7, 2012", 11 pgs.
"U.S. Appl. No. 13/327,286, Preliminary Amendment filed Jun. 1, 2012", 7 pgs.
"U.S. Appl. No. 13/428,873, Response filed Oct. 17, 2012 to Non Final Office Action mailed Jul. 18, 2012", 9 pgs.
"U.S. Appl. No. 13/428,873, Final Office Action mailed Dec. 12, 2012", 6 pgs.
"U.S. Appl. No. 13/428,873, Non Final Office Action mailed Jul. 18, 2012", 9 pgs.
"U.S. Appl. No. 13/428,873, Preliminary Amendment filed Mar. 23, 2012", 6 pgs.
"Application Serial No. 2008240191, First Examination Report mailed Sep. 21, 2012".
"Australian Application Serial No. 2006282754, Office Action mailed Nov. 8, 2011", 3 pgs.
"Combine", Merriam-Webster Online Dictionary, [Online] Retrieved From Internet: <http://www.merriam-webster.com/dictionary/combine>, (Jul. 13, 2011), 2 pgs.
"European Application Serial No. 04813849.9, Extended European Search Report mailed Apr. 8, 2008", 3 pgs.
"European Application Serial No. 04813849.9, Office Action mailed Feb. 16, 2009", 5 pgs.
"European Application Serial No. 04813849.9, Response filed Aug. 20, 2009 to Office Action mailed Feb. 16, 2009", 18 pgs.
"European Application Serial No. 07862720.5, Notice of Allowance mailed Feb. 25, 2011", 6 pgs.
"European Application Serial No. 07862720.5, Office Action mailed Feb. 26, 2010", 3 pgs.
"European Application Serial No. 07862720.5, Response filed Sep. 1, 2010 to Office Action mailed Feb. 26, 2010", 10 pgs.
"European Application Serial No. 11154746.9, Response filed Dec. 14, 2012 to Office Action mailed Nov. 15, 2012", 4 pgs.
"European Application Serial No. 11154746.9, Search Report mailed May 23, 2011", 4 pgs.
"European Application Serial No. 11154747.7, Response filed Dec. 14, 2012 to Office Action mailed Nov. 21, 2012", 4 pgs.
"European Application Serial No. 11154747.7, Search Report mailed May 23, 2011", 4 pgs.
"European Application Serial No. 11154748.5, Search Report mailed May 24, 2011", 4 pgs.
"International Application Serial No. PCT/US2008/60078, International Search Report mailed Sep. 3, 2008", 1 pg.
"International Application Serial No. PCT/US2004/041591, Written Opinion mailed Jun. 12, 2006", 4 pgs.

(56) References Cited

OTHER PUBLICATIONS

"International Application Serial No. PCT/US2006/33687, International Preliminary Report on Patentability mailed Feb. 26, 2008", 7 pgs.

"International Application Serial No. PCT/US2006/33687, Written Opinion mailed Aug. 8, 2007", 6 pgs.

"International Application Serial No. PCT/US2007/025252, International Preliminary Report on Patentability mailed Jun. 23, 2009", 8 pgs.

"International Application Serial No. PCT/US2007/025252, International Search Report mailed Apr. 18, 2008", 3 pgs.

"International Application Serial No. PCT/US2007/025252, International Search Report mailedApr. 18, 2008", 3 pgs.

"International Application Serial No. PCT/US2007/025252, Written Opinion mailed Apr. 18, 2008," 7 pgs.

"International Application Serial No. PCT/US2007/086468, International Preliminary Report on Patentability mailed Jun. 23, 2009", 10 pgs.

"International Application Serial No. PCT/US2007/086468, International Search Report Jun. 5, 2008", 4 pgs.

"International Application Serial No. PCT/US2007/086468, Written Opinion mailed Jun. 20, 2009", 9 pgs.

"Japanese Application Serial No. 2008-528250, Office Action mailed Jun. 22, 2012", 5 pgs.

"Japanese Application Serial No. 2008-528250, Response filed Nov. 22, 2012 to Office Action mailed Jun. 22, 2012", 9 pgs.

"Morsel", Merriam-Webster Online Dictionary, [Online] Retrieved From Internet: <http://www.merriam-webster.com/dictionary/morsel>, (Jul. 13, 2011), 2 pgs.

"Pulverize", Merriam-Webster Online Dictionary, [Online] Retrieved From Internet: <http://www.merriam-webster.com/dictionary/pulverize>, (Jul. 13, 2011), 2 pgs.

Adkisson, H. Davis, et al., "The Potential of Human Allogeneic Juvenile Chondrocytes for Restoration of Articular Cartilage", The American Journal of Medicine vol. 38, (Apr. 27, 2010), 1324-1333.

Adkisson, H.D.IV, et a)., "In Vitro Generation of Scaffold Independent Neocartilage", Clin Ortho Rel Res, No. 391S, (2001), S280-S294.

Akens, M K, et al., "In Vitro Studies of a Photo-oxidized Bovine Articular Cartlage", Journal of Veterinary Medicine, vol. 49, Blackwell Wissenschafts-Verlag, Berlin, (2002), 39-45.

Alfredson, Hakan, et al., "Superior results with continuous passive motion compared to active motion after periosteal transplantation", vol. 7, Knee Surg sports Trautnatol Arthrosc, Springer-Verlag, Germany, (1999), 232-238.

Alston, et al., "New method to prepare autologous fibrin glue on demand", Translational Research vol. 149, (2007), 187-195.

Augenstein, D C, et al., "Effect of Shear on the Death of Two Strains of Mammalian Tissue Cells", vol. XIII, Biotechnology and Bioengineering, USA, (1971), 409-418.

Aulthouse, Amy Lynn, et al., "Expression of the Human Chondrocyte Phenotype in Vitro", vol. 25, No. 7, In Vitro Cellular & Developmental Biology, USA, (1989), 659-668.

Azizkhan, et al., "Chondrocytes contain a growth factor that is localized in the nucleus and is associated with chomatin", Proc. Natl. Acad. Sci., vol. 77, No. 5, (1980), 2762-2766.

Bartlett, W, et al., "Autologous chondrocyte implantation at the knee using a bilayer collagen membrane with bone graft", vol. 87-B, The Journal of Bone & Joint Surgery [Br], London, (2005), 330-332.

Bartlett, W, et al., "Autologous chondrocyte implantation versus matrix-induced autologous chondrocyte implantation for osteochondral defects of the knee", vol. 87-B, No. 5, The Journal of Bone & Joint Surgery [Br], London, (2005), 640-645.

Bassleer, C, et al., "Human Chondrocytes in Tridimensional Culture", vol. 22, No. 3, PI. I, In Vitro Cellular & Developmental Biology, UK, (1986), 113-119.

Behrens, Peter, et al., "Matrix-associated autologous chondrocyte trnasplantationlimplantation (MACTIMACI)-5-year follow-up", vol. 13, The Knee, Elsevier, UK, (2006), 194-202.

Ben-Zeev, A, et al., "Protein synthesis requires cell-surface contact while nuclear events respond to cell shape in anchorage-dependent fibroblasts", Cell, vol. 21., (1980), 365-372.

Berlet, G.C., et al., "Treatment of Unstable Osteochondritis Dissecans Lesions of the Knee Using Autogenous Osteochondral Grafts (Mosaicplasty)", Arthroscopy 15-3, (1999), 312-316.

Binette, F, et al., "Tenninally Redifferentiated Human Articular Chondrocytes Express Hyaline Cartilage Markers without Hypertrophy", Genzyrne Tissue Repair, 43rd Annual Meeting, Orthopaedic Research Society, USA, (1997), 520 pgs.

Black, J., "Biological Performance of Tantalum", Clinical Materials, vol. 16., (1994), 167-173.

Bobyn, J D, et al., "Effect of pore size on the peel strength of attachment of fibrous tissue to porous-surfaced implants", J. Biomed. Mater. Res., vol. 16., (1982), 571-584.

Bobyn, JD, et al., "Characteristics of bone ingrowth and interface mechanics of a new porous tantalum biomaterial", J. Bone Joint Surg Br., 81, (1999), 907-914.

Bobyn, JD, et al., "Tissue response to porous tantalum acetabular cups", a canine model. J. Arthroplasty, 14, (1999), 347-54.

Boumediene, et al., "Modulation of rabbit articular chondrocyte (RAC) proliferation by TGF-B isoforms", Cell Prolif., vol. 28, (1995), 221-234.

Bujia, et al., "Synthesis of human cartilage using organotypic cell culture", ORL, vol. 55, (1993), 347-351.

Bujia, J, et al., "Effect of Growth Factors on Cell Proliferation by Human Nasal Septal Chondrocytes Cultured in Monolayer", Acta Otolaryngol, vol. 114, Scandinavian University Press, Sweden, (1994), 539-543.

Chang, et al., "Cartilage-Derived Morphogenetic Proteins", J. Biol. Chem., 269, (1994), 28227-28234.

Chawla, K, et al., "Short-term retention of labeled chondrocyte subpopulations in stratified tissue-engineered cartilaginous constructs implanted in vivo in mini-pigs", Tissue Engineering vol. 13, No. 7, (2007), 1525-1538.

Cherry, R S, et al., "Hydrodynamic effects on cells in agitated tissue culture reactors", Bioprocess Engineering, vol. I, Springer-Verlag, USA, (1986), 29-41.

Cherry, Robert S, et al., "Physical Mechanisms of Cell Damage in Microcarrier Cell Culture Bioreactors", Biotechnology and Bioengineering, vol. 32, John Wiley & Sons, Inc., USA, (1988), 1001-1014.

Cherry, Robert S, et al., "Understanding and Controlling Fluid-Mechanical Injury of Animal Cells in Bioreactors", Animal Cell Biotechnology, vol. 4, Academic Press Limited, USA, (1990), 71-121.

Choi, Ye Chin, et al., "Effect of Platelet Lysate on Growth and Sulfated Glycosaminoglycan Synthesis in Articular Chondrocyte Cultures", Arthritis and Rheumatism, vol. 22, No. 2, USA, (1980), 220-224.

Christel, P, et al., "Osteochondral Grafting using the Mosaicplasty Technique", [Online] Retrived from the internet Dec. 16, 2008: <www.maitrise-orthop.com/corpusmaitri/orthopaedic/mo76_mosaicplasty/index.shtm>, 20 pgs.

Convery, F.R., et al., "The Repair of Large Osteochondral Defects", An Experimental Study in Horses, Clin. Orthrop. 82., (1972), 253-262.

Coutts, Richard D, et al., "Rib Periochondrial Autografts in Full-Thickness Articular Cartilage Defects in Rabbits", Clinic Orthopaedics and Related Research, No. 275, USA, (1989), 263-273.

Craigmyle, M B, "Studies of cartilage autografts and homografts in the rabbit", British Journal of Plastic Surgery 8, (1955), 93-100.

Croughan, Matthew Shane, et al., "Hydrodynamic Effects on Animal Cells Grown in Microcarrier Cultures", Biotechnology and Bioengineering, vol. XXIX, John Wiley & Sons, Inc., USA, (1987), 130-141.

Delbruck, Axel, et al., "In-Vitro Culture of Human Chondrocytes from Adult Subjects", Connective Tissue Research, Gordon and Breach, Science Publishers, Inc., USA, (1986), 155-172.

Dewey, Jr, C F, et al., "The Dynamic Response of Vascular Endothelial Cells to Fluid Shear Stress", Journal of Biomechnical Engineering, vol. 103, USA, (1981), 177-185.

(56) References Cited

OTHER PUBLICATIONS

Didier, R, et al., "Production de cartilage et d'os, au sein de greffes vivantes et mortes, chez le lapin", Comptes Rendus Hebdomadaires, (1928), 5 pp.

Dogterom, A A, et al., "Matrix depletion of young and old human articular cartilage by cultured autologous synovium fragments; a chondrocyte-independent effect", Rheumatology International, vol. 5, Springer-Verlag, UK, (1985), 169-173.

Dowthwaite, Gary P, et al., "The surface of articular cartilage contains a progenitor cell population", Journal of Cell Science vol. 117, The Company of Biologists, 2004 UK, (2004), 889-897.

Drobnic, M. MD, et al., "Comparison of four techniques for the fixation of a collagen scaffold in the human cadaveric knee", Osteoarthritis and Cartilage, vol., 14 Elsevier Ltd., UK, (2006), 337-344.

Elima, Kati, et al., "Expression of mRNAs for collagens and other matrix components in dedifferentiating and redifferentiating human chondrocytes in culture", FEBS Letters, vol. 258 No. 2, Elsevier Science Publishers B.V. (Biomedical Division), UK, (1989), 195-198.

Evans, Robin C, et al., "Solute diffusivity correlates with mechanical properties and matrix density of compressed articular cartilage", Archives of Biochemistry and Biophysics, vol. 442, Elsevier, UK, (2005), 1-10.

Farmer, S R, et al., "Altered Translatability of Messenger RNA from Suspended Anchorage-Dependent Fibroblasts", Reversal upon Cell Attachment to a Surface, Cell, vol. 15., (1978), 627-637.

Feder, J, "Tissue Engineering in Musculoskeletal Clinical Practice: The Promise of Chondral Repair Using Neocartilage", Am. Acad. Orthop. Surg., Chapter 22., (2004), 219-226.

Feder, Joseph, et al., "The Large-Scale Cultivation of Mammalian Cells", Scientific American, Inc USA, (1983), 36-43.

Folkman, J, et al., "Role of cell shape in growth control", Nature, vol. 273., (1978), 345-349.

Frangos, John, et al., "Flow Effects on Prostacyclin Production by Cultured Human Endothelial Cells", Science, vol. 227, Texas, USA, (1985), 1477-1479.

Freed, L E, et al., "Neocartilage formation in virtro and invivo using cells cultured on synthetic biodegradable polymers", J. Biomed. Mater. Res. vol. 27 (1), (1993), 11-23.

Freed, L. E, et al., "Cartilage Tissue Engineering Based on Cell-Polymer Constructs", Tissue Engineering of Cartilage, CRC Press, Inc., USA, (1995), 1788-1806.

Freed, L. E, et al., "Composition of Cell-Polymer Cartilage Implants", Biotechnology and Bioengineering, vol. 43, John Wiley & Sons, Inc., USA, (1994), 605-614.

Freed, L. E, et al., "Cultivation of Cell-Polymer Cartilage Implants in Bioreactors", Journal of Cellular Biochemistry, vol. 51, Wiley-Liss, Inc., USA, (1993), 257-264.

Freed, L. E, et al., "Cultivation of Cell-Polymer Tissue Constructs in Simulated Microgravity", Biotechnology and Bioengineering, vol. 46, John Wiley & Sons, Inc., USA, (1995), 306-313.

Freed, Lisa E, et al., "Tissue engineering of cartilage in space", Proc. Natl. Acad. Sci., vol. 94, The National Academy of Sciences, USA, (1997), 13885-13890.

Fry, Donald, "Acutte Vascular Endothelial Changes Associated with Increased Blood Velocity Gradients,", Journal of the American Heart Association, vol. XXII, American Heart Association, USA, (1968), 165-197.

Fu?, M, et al., "Characteristics of human chondrocytes, osteoblasts and fibroblasts seeded onto a type I/II collagen sponge under different culture conditions", Annals of Anatomy, vol. 182, Urban & Fischer Verlag, Germany, (2000), 303-310.

Galera, et al., "Effect of transforming growth factor-B1 (TGF-B1) on matrix synthesis by monolayer cultures of rabbit chondrocytes during the dedifferentiating process", Experimental Cell Research, vol. 200, (1992), 379-392.

Gibble, et al., "Fibrin glue: the perfect operative sealant", Transfusion, 1990, vol. 30, No. 8., 741-747.

Gille, J, et al., "Migration pattern, morphology and viability of cells suspended in or sealed with fibrin glue: A histomorphologic study", Tissue and Cell, Vo. 37, Elsevier, UK, (2005), 339-348.

Girotto, Davide, et al., "Tissue-specific gene expression in chondrocytes grown on three-dimensional hyaluronic acid scaffolds", Biomaterials, vol. 24, Elsevier, UK, (2003), 3265-3275.

Gooch, K J, et al., "Effects of Mixing Intensity on Tissue-Engineered Cartilage", Biotechnology and Bioengineering, vol. 72, No. 4, John Wiley & Sons, Inc., USA, (2001), 402-407.

Guilak, F, et al., "Functional tissue engineering: the role of biomechanics in articular cartilage repair", Clin Orthop Relat Res, vol. 391S., (2001), 295-305.

Haart, et al., "Optimization of chondrocyte expansion in culture", Acta Orthop Scand, vol. 70, No. 1, (1999), 55-61.

Hacking, S A, et al., "Fibrous tissue ingrowth and attachment to porous tantalum", J. Biomed. Mater. Res., vol. 52, No. 4., (2000), 631-638.

Han, et al., "Scaffold-free Grafts for Articular Cartilage Defects", Clin Orthop Relat Res. vol. 466, (2008), 1912-1920.

Harrison, et al., "Osteogenin promotes reexpression of cartilage phenotype by dedifferentiated articular chondrocytes in serum-free medium", Experimental Cell Research, vol. 192, (1991), 340-345.

Harrison, et al., "Transforming growth factor-beta: Its effect on phenotype reexpression by dedifferentiated chondrocytes in the presence and absence of osteogenin", In Vitro Cell Dev. Biol., vol. 28A, (1992), 445-448.

Hiraki, et al., "Effect of transforming growth factor B on cell proliferation and glycosaminoglycen synthesis by rabbit growth-plate chondrocytes in culture", Biochimica et Biophysica Acta, vol. 969, (1988), 91-99.

Hollander, Anthony P, et al., "Maturation of Tissue Engineered Cartilage Implanted in Injured and Osteoarthritic Human Knees,", Tissue Engineering, vol. 12, No. 7, Mary Ann Leibert, Inc., UK, (2006), 1787-1798.

Hollinger, Jeffrey O, et al., "Poly(alpha-hydroxy acids): carriers for bon morphogenetic proteins", Biomaterial, vol. 17, (1996), 187-194.

Horton, et al., "Transforming growth factor-beta and fibroblast growth factor act synergistically to inhibit collagen II synthesis through a mechanism involving regulatory DNA sequences", Journal of Cellular Physiology, vol. 141, (1989), 8-15.

Hu, Wei-Shou, "Bioreactors for Animal Cell Cultivation", Recent Advances in Biotechnology, Kluwer Academic Publishers, Netherlands, (1992), 243-261.

Huang, et al., "Tissue Engineering", vol. 8, No. 3, (2002), 469-481.

Hunziker, E.B., et al., "Quantitative structural organization of normal adult human articular cartilage", Osteoarthritis and Cartilage 10, (2002), 564-572.

Iwasa, J, et al., "Clinical application of scaffolds for cartilage tissue engineering", Surg Sports Traumalol Arthorsc vol. 13, No. 4, (2007), 693-703.

Jones, C W, et al., "Matrix-induced autologous chondrocyte implantation in sheep: objective assessments including confocal arthroscopy", J. Orthopaedic Research vol. 26, (2008), 292-303.

Jurgensen, K, et al., "A New Biological Glue for Cartilage-Cartilage Interfaces: Tissue Transglutaminase", JBJS (Am), 1997, vol. 79., (1997), 185-193.

Kandel, et al., "Fetal bovine serum inhibits chondrocyte collagenase production: interleukin 1 reverses this effect", Biochim. Biophys. Acta.: 1053(2-3), (1990), 130-134.

Kato, Y, et al., "Sulfated Proteoglycan Synthesis by Conftuent Cultures of Rabbit Costal Chondrocytes Grown in the Presence of Fibroblast Growth Factor", J. Cell Biology, vol. 100., (1985), 477-485.

Kavalkovich, Karl W, et al., "Chondrogenic Differentiation of Human Mesenchymal Stem Cells Within an Alginate Layer Culture System", In Vitro Cell. Dev. Biol.-Animal, vol. 38, Society for In Vitro Biology, USA, (2002), 457-466.

Kim, et al., "OsteoArthritis and Cartilage", vol. 11, (2003), 653-664.

Kimura, Tomoatsu, et al., "Chondrocytes Embedded in CoHagen Gels Maintain Cartilage Phenotype During Long-term Cultures",?Clinical Orthopaedics and related Research, vol. 186, Japan, (1984), 231-239.

(56) References Cited

OTHER PUBLICATIONS

Klagsbrun, et al., "Purification of a cartilage-derived growth factor", The Journal of Biological Chemistry, vol. 255, No. 22, (1980), 10859-10866.
Klagsbrun, et al., "The stimulation of DNA synthesis and cell division in chondrocytes and 3T3 cells by a growth factor isolated from cartilage", Exp Cell Res, vol. 105, (1977), 99-108.
Klein, T J, et al., "Tailoring secretion of proteoglycan 4 (PRG4) in tissue-engineered cartilage", Tissue Engineering, vol. 12, No. 6., (2006), 1429-1439.
Klein, T J, et al., "Tissue engineering of stratified articular cartilage from chondrocyte subpopulations", OsteoArthritis and Cartilage vol. 11, (2003), 595-602.
Kon, E, et al., "Arthroscopic second generation autologous chondrocyte implantation at 48 months follow up", Osteoarthritis and Cartilage vol. 15, Suppl. B, (2007), B44-45.
Kon, E, et al., "Arthroscopic Second-generation Autologous Chondrocyte Implantation Compared with Microfracture of Chondral Lesions of the Knee", Am J. of Sports Medicine vol. 37, No. 1, (2009), 33-41.
Krueger, John W, et al., "An In Vitro Study of Flow Response by Cells", Journal of Biomechanics, vol. 4, Pergamon Press, Great Britain, (1971), 31-36.
Kuettner, Klaus E, et al., "Synthesis of Cartilage Matrix by Mammalizn Chondrocytes in Vitro.l. Isolation, Culture Characteristics, and Morphology", The Journal of Cell Biology, vol. 93, The RockefeHer University Press, USA, (1982), 743-750.
Kujawa, et al., "Hyaluronic acid bonded to cell culture surfaces inhibits the program of myogenesis", Developmental Biology, vol. 113, (1986), 10-16.
Kujawa, Mary J, et al., "Hyaluronic Acid Bonded to Cell-Culture Surfaces Timulates Chondrogenesis inStage 24 Limb Mesenchyme Cell Cultures", Developmental Biology, vol. 114, Academic Press, Inc., USA, (1986), 504-518.
Kujawa, Mary J, et al., "Substrate-Bonded Hyaluronic Acid Exhibits a Size-Dependent Stimulation of Chondrogenic Differentiation of Stage 24 Limb Mesenchymal Cells in Culture", Developmental Biology, vol. 114, Academic Press, Inc., USA, (1986), 519-528.
Lee, et al., "Primary cultured chondrocytes of different origins respond differently to bFGF and TGF-B", Life Sciences, vol. 61, No. 3, (1997), 293-299.
Lin, Z, et al., "Gene Expression Profiles of Human Chondrocytes during Passaged Monolayer Cultivation", J. Orthopaedic Research, vol. 26, (2008), 1230-1237.
Liu, Lin-Shu, et al., "An osteoconductive collagen/hyaluronate matrix for bone regeneration", Biomaterials vol. 20, Elsevier, UK, (1999), 1097-1108.
Lucas, Paul A, et al., "Ectopic induction of cartilage and bone by water-soluble proteins from bovine bone using a collagenous delivery vehicle", Journal of Biomedical Materials Research: Applied Biomaterials, vol. 23, No. Al, (1989), 23-39.
Luyten, Frank P, et al., "Articular Cartilage Repair: Potential Role of Growth and Differentiation Factors", Biological Regulation ofthe Chondrocytes, USA, 227-236.
MacKay, et al., "Chondrogenic differentiation of cultured human mesenchymal stem cells from marrow", Tissue Engineering, vol. 4, No. 4, (1998), 415-430.
Malemud, C J, et al., "The effect of chondrocyte growth factor on membrane transport by articular chondrocytes in monolayer culture", Connective Tissue Research, vol. 6, (1978), 1-9.
Mandl, E W, et al., "Multiplication of human chondrocytes with low seeding densities accelerates cell yield without losing redifferentiation capacity", Tissue Engineering, vol. 10, No. 1/2, (2004), 109-120.
Mandl, E W, et al., "Serum-free medium supplemented with high-concentration FGF2 for cell expansion culture of human ear chondrocytes promotes redifferentiation capacity", Tissue Engineering, vol. 8, No. 4, (2002), 573-582.
Mannheim, A, "Free Autoploastic Cartilage transplantation—Uber freie autoplastische Knorpeltransplantation", Arch. F klin Chir, (1926), 668-672.
Marcacci, M, et al., "Multiple Osteochondral Arthroscopic Grafting (Mosaicplasty) for Cartilage Defects of the Knee: Prospective Study Results at 2-Year Follow-up", J. Arthroscopic & Related Surgery, vol. 21, No. 4., (2005), 462-470.
Marlovits, S, et al., "Changes in the ratio of type-I and type-II collagen expression during monolayer culture of human chondrocytes", JBJS, vol. 86-B, (2004), 286-95.
Marlovits, Stefan, et al., "Early postoperative adherence of matrix-induced autologous chondrocyte implantation for the treatment of full-thickness cartilage defects of the femoral condyle", Knee Surg Sports Traumatol Arthorosc, vol. 13, Springer-Verlag, Austria, (2005), 451-457.
Marvin, H M, "The Value of the Xanthine Diuretics in Congestive Heart Failure", The Journal of the American Medical Association, vol. 87, No. 25, Abstract only, (Dec. 18, 1926), 2131-2132.
Mathiowitz, Edith, et al., "Biologically erodable microspheres as potential oral drug delivery systems", Nature, vol. 386, (Mar. 1997), 410-414.
McNickle, Allison G, et al., "Overview of Existing Cartilage Repair Technology", Sports Med Arthorosc Rev., vol. 16, No. 4, Lippincott Williams & Wilkins, USA, (2008), 196-201.
McQueen, Anne, et al., "Flow Effects on the Viability and Lysis of Suspended Mammalian Cells", Biotechnology Letters, vol. 9, No. 12, California Institute of Technology, USA, (1987), 831-836.
Merchuk, Jose Celman, "Shear Effects on Suspended Cells", Advances in Biochemical Engineering Biotechnology, vol. 44, Springer-Verlag Berlin Heidelberg, (1988).
Merchuk, Jose C, et al., "Why use air-lift bioreactors?", Tibtech, vol. 8, Elsevier Science Publishers Ltd., UK, (1990), 66-71.
Mienaltowski, M J, et al., "Differential gene expression associated with postnatal equine articular cartilage maturation", BMC Musculoskeletal Disorders, vol. 9., (2008), 149-162.
Minas, T, et al., "Current Concepts in the Treatment of Articular Cartilage Defects", Orthopedics, vol. 20., (1997), 525-538.
Mow, V C, et al., "Experimental Studies on Repair of Large Osteochondral Defects at a High Weight Bearing Area of the Knee Joint: A Tissue Engineering Study", Transactions of the ASME, Journal of Biomechanical Engineering, vol. 113, USA, (1991), 198-207.
Nixon, Alan J, et al., "Temporal matrix synthesis and histologic features of a chondrocyte-laden porous collagen cartilage analogue", American Journal of Veterinary Research, vol. 54, No. 2, USA, (1993), 349-356.
Oldshue, J Y, et al., "Comparison of Mass Transfer Characteristics of Radial and Axial Flow Impellers", Mixing Proceedings of the 6th European Conference, Pavia, Italy,, (1988), 345-350.
Papoutsakis, Eleftherios T, "Fluid-mechanical damage of animal cells in bioreactors", TibTech, vol. 9, Elsevier Science Publishers Ltd. (UK), (1991), 427-437.
Pavesio, Allesandra, et al., "Hyaluronan-based scaffolds (Hyalograft C) in the treatment of knee cartilage defects; preliminary clinical findings", Hyaluronan Scaffolds in Cartilage Repair, UK, (2003), 203-217.
Peer, Lyndon, "Diced Cartilage Grafts—New Method for Repair of Skull Defects, Mastoid Fistula and Other Deformities", Archives of Otolaryngology, vol. 38, No. 2, (1943), 156-165.
Peretti, G M, et al., "Meniscal repair using engineered tissue", J. Orthop Res, vol. 19, No. 2., (2001), 278-85.
Polettini, Bruno, "Su neoformazioni carilaginee ed ossee determinate da innesti di frammenti di cartilagine e d'osso fissati", (1922), 179-192.
Reginato, et al., "Formation of nodular structures resembling mature articular cartilage in long-term primary cultures of human fetal epiphyseal chondrocytes on a hydrogel substrate", Arthritis & Rheumatism, vol. 37, No. 9, (1994), 1338-1349.
Ronga, Mario, et al., "Arthroscopic Autologous Chondrocyte Implantation for the Treatment of a Chondral Defect in the Tibial Plateau of the Knee", Arthroscopy: The Journal of Arthroscopic and Related Surgery, vol. 20, No. 1, Italy, (2004), 79-84.
Ronga, Mario, et al., "Tissue Engineering Techniques for the Treatment of a Comples Knee Injury", Arthroscopy: The Journal of Arthroscopic and Related Surgery, vol. 22 No. 5, Italy, (2006), 576. e1-576.e3.

(56) References Cited

OTHER PUBLICATIONS

Rosier, R N, et al., "Transforming growth factor bela: an autocrine regulator of chondrocytes", Connective Tissue Research vol. 20., (1989), 295-301.
Rosselot, G, et al., "Development of a serum-free system to study the effect of growth hormone and insulinlike growth factor-I on cultured postembryonic growth plate chondrocytes", In Vitro Cell Dev Biol vol. 28A., (1992), 235-244.
Russlies, M., et al., "A cell-seeded biocomposite for cartilage repair", Annals of Anatomy vol. 184, Urban & Fischer Verlag, UK, (2002), 317-323.
Saini, Sunil, et al., "Concentric Cylinder Bioreactor for Production of Tissue Engineered Cartilage; Effect of Seeding Density and Hydrodynamic Loading on Construct Development", Biotechnol Prog., vol. 19, American Chemical Society and American Institute of Chemical Engineers, USA, (2003), 510-521.
Salter, Robert B, et al., "The Biological Concept of Continuous Passive Motion of Synovial Joints: The First 18 Years of Basic Research and Its Clinical Application", Articular Cartilage and Knee Joint Function : Basic Science and Arthroscopy, Raven Press, Ltd., NY, USA, (1990), 335-353.
Schmidt, Tannin A, et al., "Synthesis of Proteoglycan 4 by Chondrocyte Subpopulations in Cartilage Explants, Monolayer Cultures, and Resurfaced Cartilage Cultures", Arthritis & Rheumatism, vol. 50, No. 9, American College of Rheumatology, USA, (2004), 2849-2857.
Schwan, B L, "Human Amniotic Membrane Transplantation for the Treatment of Ocular Surface Disease", Human Amniotic Membrane Transplantation, (2002), 1-7.
Schwarz, Ray P, et al., "Cell Culture for Three-Dimensional Modeling in Rotating-Wall Vessels: An Application of Simulated Microgravity", Journal of Tissue Culture Meth., Tissue Culture Association, TX, USA, (1992), 51-58.
Shahgaldi, B F, et al., "Repair of Cartilage Lesions Using Biological Implants—A Comparative Histological and Biomechanical Study in Goats", Journal of Bone & Joint Surgery, vol. 73-5, UK, (1991), 57-64.
Smith, R. Lane, et al., "Effects of Fluid-Induced Shear on Articular Chondrocyte Morphology and Metabolism In Vitro", Journal of Orthopaedic Research, the Journal of Bone and Joint Surgery, Inc., vol. 13, USA, (1995), 824-831.
Sokoloff, L, et al., "In vitro culture of articular chondrocytes", Federation Proc vol. 32., (1973), 1499-1502.
Sokoloff, L., et al., "Sulfate Incorporation by Articular Chondrocytes in Monolayer Culture", Arthritis and Rheumatism vol. 13, No. 2., (1970), 118-124.
Song, C. X, et al., "Formulation and Characterization of Biodegradable Nanoparticles for Intravascular Local Drug Delivery", Journal of Controlled Release vol. 43, No. 2/03,, XP00632668, (Jan. 18, 1997), 197-212.
Spangenberg, K M, et al., "Histomorphometric Analysis of a Cell-Based Model of Cartilage Repair", Tissue Engineering, vol. 8, No. 5., (2002), 839-46.
Stathopoulos, N. A, et al., "Shear Stress Effects on Human Embryonic Kidney Cells in Vitro", Biotechnology and Bioengineering, vol. XXVII, John Wiley & Sons, Inc., USA, (1985), 1021-1026.
Stewart, Matthew C, et al., "Phenotypic Stability of Articular Chondrocytes In Vitro: The Effects of Culture Models, Bone Morphogenetic Protein 2, and Serum Supplemenation", Journal of Bone and Mineral Research, vol. 15, No. 1, (2000), 166-174.
Stiles, C. D, et al., "Dual control of cell growth by somatomedins and platelet-derived growth factor", PNAS vol. 76, No. 3., (1979), 1279-1283.
Stockwell, R. A, "The cell density of human articular and costal cartilage", J. Anal. vol. 101,No. 4., (1967), 753-763.
Thilly, W. G, et al., "Microcarrier Culture: A Homogeneous Environment for Studies of Cellular Biochemistry", Methods in Enzymology vol. LVIII, ISBN 0-12-181958-2, Academic Press, Inc., New York, New York, United States., (1979), 184-194.
Thilly, W. G, et al., "Microcarriers and the problem of high density cell culture", From Gene to Protein: Translation in Biotechnology vol. 19, Academic Press, Inc., New York, New York, United States., (1982), 75-103.
Trattnig, S., et al., "Differentiating normal hyaline cartilage from post-surgical repair tissue using fast gradient echo imaging in delayed gadolinium-enhanced MRI (dGEMRIC) at 3 Tesla", Eur Radial vol. 18., (2008), 1251-1259.
Trattnig, S., et al., "Quantitative T2 Mapping of Matrix-Associated Autologous Chondrocyte Transplantation at 3 Tesla an in vivo Cross-Sectional Study", Investigative Radiology vol. 42, No. 6., (2007), 442-448.
Trattnig, Siegfried, et al., "Matrix-based autologous chondrocyte implantation for cartilage repair: noninvasive monitoring by high-resolution magnetic resonance imaging", Magnetic Resonance Imaging, vol. 23, Elsevier, Austria, (2005), 779-787.
Vacanti, C. A, et al., "Synthetic Polymers Seeded with Chondrocytes Provide a Template for New Cartilage Formation", Plastic and Reconstructive Surgery, vol. 88, No. 5, (1991), 753-759.
Vanderploeg, E. J, et al., "Articular chondrocytes derived from distinct tissue zones differentially respond to in vitro oscillatory tensile loading", Osteoarthritis and Cartilage vol. 16., (2008), 1228-1236.
Venkat, Raghavan V, et al., "Study of Hydrodynamics in Microcarrier Culture Spinner Vessels: A Particle Tracking Velocimetry Approach", Biotechnology and Bioengineering, vol. 49, John Wiley & Sons, Inc., USA, (1996), 456-466.
Verwoerd, C.D.A., et al., "Wound Healing of Autologous Implants in the Nasal Septal Cartilage", Department of Otorhinolaryngology and Pathology, ORL vol. 53, (1991), 310-314.
Vishwakarma, G. K, et al., "Isolation & cryo-preservation of human foetal articular chondrocytes", Indian J. Med Res vol. 98., (1993), 309-313.
Von Schroeder, Herbert P, et al., "The use of polylatic acid matrix and periosteal grafts for the reconstruction of rabbit knee articular defects", Journal of Biomedical Materials Research, vol. 25, (1991), 329-339.
Willers, Craig, et al., "Articular cartilage repair: procedures versus products", Expert Rev. Med. Devices, vol. 4., No. 3, Future Drugs Ltd, US, (2007), 373-392.
Xu, et al., "Injectable Tissue-Engineered Cartilage with Different Chondrocyte Sources", vol. 113, (2004), 1361-1371.
Yoshihashi, Yuji, et al., "Tissue Reconstitution by Isolated Articular Chondrocytes in vitro", J. Jpn. Orthop. Assoc., vol. 58, (1983), pp. 629-641.
Zheng, M H, et al., "Matrix-induced autologous chondrocyte implantation (MACI): Biological and Histological Assessment", Tissue Engineering, vol. 13, No. 4., (2007), 737-746.
Zimber, M P, et al., "TGF—β Promotes the Growth of Bovine Chondrocytes in Monolayer Culture and the Formation of Cartilage Tissue on Three-Dimensional Scaffolds", Tissue Engineering, vol. 1, No. 3., (1995), 289-300.
US 8,382,851, 02/2013, Gage et al. (withdrawn)

\* cited by examiner

APPARATUS FOR FORMING AN IMPLANT

CROSS-REFERENCE TO RELATED APPLICATIONS

This application is a continuation of U.S. patent application Ser. No. 12/101,553, filed Apr. 11, 2008, which claims priority from provisional application no. 60/911,429, filed Apr. 12, 2007, the entire disclosures of which are herein incorporated by reference.

BACKGROUND OF THE INVENTION

The need for implants for repairing tissue defects, such as cartilage tissue defects, is ongoing. Materials have been developed to fill spaces comprising tissue defects, but have typically been two-dimensional, comprising, for example, a flat sheet cut to approximate the dimensions of a tissue defect, or a layer of cells grown in vitro, from which a two dimensional sheet of cells is applied to a tissue defect.

U.S. Pat. No. 5,067,964 to Richmond et al. discloses an articular cartilage repair piece and methods of forming. This patent discloses a repair piece which includes a backing layer of non-woven, felted fibrous material which is conformable to flat and curved surfaces.

U.S. Pat. Nos. 5,655,546 and 6,179,871 to Halpern disclose methods for repairing a cartilage defect, comprising the provision of apertures in the cartilage by drilling holes at the base of the cartilage defect. The holes may enter the mesenchymal depot. In these methods, a porous scaffold material containing a plurality of magnetic particles is introduced into the apertures. Subsequently and sequentially, magnetically-tagged cartilage growth promoting materials such as chondrocytes or growth factors are injected into the area of the defect.

U.S. Pat. No. 6,443,988 to Felt et al. discloses methods and apparatuses for repairing a tissue site. The method involves use of a curable polyurethane adapted to be mixed at time of use in order to provide a flowable composition and initiate cure.

U.S. Pat. Nos. 6,511,958 and 6,514,514 to Atkinson et al. disclose devices and products for repair of cartilage lesions, comprising a cartilage repair matrix suitable for conforming to a cartilage defect and a cartilage-inducing composition on or within the matrix.

U.S. Pat. Nos. 6,626,945, 6,632,246 and 6,852,125 to Simon et al describe cartilage plugs made from a biocompatible artificial material. These plugs are made according to pre-determined shapes.

BRIEF SUMMARY OF THE INVENTION

The aforementioned patents do not describe a biological implant having surface contours substantially conforming to those of a tissue defect such as a cartilage defect. In view of these considerations, the present inventors have developed methods, compositions, apparatuses and kits for repairing a tissue defect such as a cartilage defect.

In some embodiments of the present teachings, these methods comprise forming, on a tissue defect of a subject, a mold conforming to the contours of at least a portion of the tissue defect, removing the mold from the defect, forming in the mold an implant comprising one or more tissue particles and a biocompatible carrier, whereby the implant has a shape substantially conforming to the contours of at least the portion of the tissue defect, separating the implant from the mold, and applying the implant to at least the portion of the tissue defect.

In various aspects of the method and apparatus, the mold comprises for example a pliable substrate having shape memory, which in one embodiment is a sterile substrate. The substrate having shape memory is for example a metal foil such as aluminum foil, a plastic, or a polymer such as a polyurethane or a curable plastic. The substrate may be a material permeable to liquid. The one or more tissue particles are in one embodiment initially suspended in a liquid medium which can be a cell, tissue or organ storage medium. In one embodiment, forming the implant includes removing an amount of the liquid medium from the mold. The liquid medium may be removed by introducing one or more perforations in the mold, thereby promoting draining of the liquid medium from the mold. Alternatively, the mold is made of a substrate material initially having perforations therethrough, or of a substrate material that is permeable to liquid. The liquid medium may be further removed by contacting the mold with an absorbent pad. In one embodiment the method further comprises distributing the tissue particles substantially uniformly in the mold. The biocompatible carrier can include at least one biocompatible polymer such as a fibrinogen, a fibrin, a thrombin, a type I collagen, a type II collagen, a type III collagen, a gelatin, a fibronectin, a laminin, a hyaluronic acid, a hydrogel, a pegylated hydrogel or a chitosan. The biocompatible carrier may include at least one biocompatible adhesive such as a fibrin adhesive. The implant may further comprise at least one bioactive agent such as a growth factor. The growth factor can be selected for example from among a TGF-β, a bone morphogenetic protein, a growth differentiation factor, ADMP-1, a fibroblast growth factor, a hedgehog protein, an insulin-like growth factor, a platelet-derived growth factor, an interleukin, a colony-stimulating factor, an EGF and an activin. The at least one bioactive agent may be a bioactive peptide.

In one aspect, forming in the mold an implant comprises forming an implant including a first layer including the one or more tissue particles and a second layer comprising the biocompatible carrier. The second layer may further include at least one bioactive agent, which can be a growth factor which can be selected from among a TGF-β, a bone morphogenetic protein, a growth differentiation factor, ADMP-1, a fibroblast growth factor, a hedgehog protein, an insulin-like growth factor, a platelet-derived growth factor, an interleukin, a colony-stimulating factor, an EGF and an activin. The at least one bioactive agent in a second layer of the implant can be a bioactive peptide. In another aspect of the method, applying the implant to the tissue defect includes inserting the implant at the tissue defect. Applying the implant to the tissue defect can further comprise affixing the implant to the tissue defect. Inserting the implant at the tissue defect can include inserting the implant using a minimally invasive surgical technique, such as arthroscopically. In one embodiment, the biocompatible carrier can be a biocompatible gel, such as a starch gel, an agarose gel, a polyacrylamide gel or a combination thereof. The carrier that includes at least one biocompatible polymer may be autologous to the subject. In various aspects, the subject of treatment using the method is a non-human mammal, or is a human in need of treatment of the tissue defect. In one aspect, the contours of the tissue defect being treated are three-dimensional. In one aspect the contours of the tissue defect can be substantially cylindrical.

In another aspect, a method of repairing a tissue defect includes forming, on a tissue defect in a subject, a mold having a surface conforming substantially to contours of the tissue defect, wherein the mold comprises a bioabsorbable substrate having shape memory, removing the mold from the tissue defect, forming within the mold an implant comprising at least a first layer, wherein the first layer comprises one or more tissue particles and a biocompatible carrier, whereby the implant has a shape substantially conforming to the contours of the tissue defect; and applying the mold and implant to the tissue defect. The bioabsorbable substrate having shape memory is sterile. The bioabsorbable substrate having shape memory is for example a plastic, which can be a bioabsorbable polymer such as a bioabsorbable polyester. The bioabsorbable polymer can be a polyester selected from among a polylactic acid, a polyglycolic acid, and a co-polymer comprising a polylactic acid and a polyglycolic acid. In one aspect, the method may further include distributing the tissue particles substantially uniformly throughout the first layer. The second layer includes for example at least one biocompatible carrier. The second layer can include at least one bioactive agent such as a growth factor.

In another aspect a method is provided for repairing a tissue defect in a subject, which includes forming, on the tissue defect a mold having a surface substantially conforming to the contours of at least a portion of the tissue defect, removing the mold from the tissue defect, forming within the mold an implant comprising one or more tissue particles and a biocompatible carrier, whereby the implant has a shape substantially conforming to the contours of the portion of the tissue defect, applying the mold and implant together to the portion tissue defect, and separating the implant from the mold after applying to the tissue defect. Applying the implant to the tissue defect may include inserting the implant at the tissue defect and may further include affixing the implant to the tissue defect. Inserting the implant at the tissue defect may include inserting the implant using a minimally invasive surgical technique such as arthroscopically.

In another aspect, apparatus is provided for forming an implant for repairing a tissue defect, the apparatus including a mold having a shape substantially conforming to the contours of a tissue defect of a subject, and a composition including one or more tissue particles and a biocompatible carrier, the composition disposed in the mold wherein the shape of the composition substantially conforms to the contours of the tissue defect. The mold is formed from a substrate having shape memory such as for example a metal foil such as aluminum foil, a plastic, or a polymer such as a polyurethane or a curable plastic. The substrate may be for example a sterile substrate. The substrate may be a material permeable to liquid. The substrate may be a bioabsorbable substrate having shape memory such as a bioabsorbable polymer including a bioabsorbable polyester which may be selected from a polylactic acid, a polyglycolic acid, and a co-polymer comprising a polylactic acid and a polyglycolic acid. The mold may have one or more perforations therethrough for draining excess liquid medium. The tissue particles can be cartilage tissue particles such as neocartilage particles, juvenile cartilage particles, cadaver cartilage particles, or may be selected from among bone tissue particles, liver tissue particles, renal tissue particles, neuronal tissue particles, muscle tissue particles, adipose tissue particles, and a combination thereof. The apparatus includes in some aspects the tissue particles distributed substantially uniformly in the mold. The biocompatible carrier may include at least one biocompatible adhesive such as a fibrin adhesive. The biocompatible carrier can include at least one biocompatible polymer such as a fibrinogen, a fibrin, a thrombin, a type I collagen, a type II collagen, a type III collagen, a gelatin, a fibronectin, a laminin, a hyaluronic acid, a hydrogel, a pegylated hydrogel or a chitosan. A biocompatible polymer may be autologous to the subject. The biocompatible carrier may include at least one biocompatible adhesive such as a fibrin adhesive. The biocompatible carrier may include a biocompatible gel selected from a starch gel, an agarose gel, a polyacrylamide gel and a combination thereof. In one aspect, the apparatus includes an implant having a first and a second layer. The second layer can include at least one bioactive agent such as a growth factor as described elsewhere herein. The at least one bioactive agent may be a bioactive peptide.

In another aspect, a method of forming an implant for repairing a tissue defect includes providing a substrate having shape memory, forming the substrate into a mold of a tissue defect of a subject, wherein the mold substantially conforms to contours of at least a portion of the tissue defect, removing the mold from the tissue defect, and disposing in the mold a composition comprising at least one biological agent and a biocompatible carrier, thereby forming the implant having a shape substantially conforming to the contours of at least the portion of the tissue defect. The at least one biological agent can be a pharmaceutical compound. The biological agent is for example a plurality of tissue particles such as cartilage particles. The cartilage tissue particles may be neocartilage particles, juvenile cartilage particles, cadaver cartilage particles, or may be selected from among bone tissue particles, liver tissue particles, renal tissue particles, neuronal tissue particles, muscle tissue particles, adipose tissue particles, and a combination thereof. The method may further comprise mixing within the mold at least one bioactive agent. The bioactive agent can be a growth factor selected from among a TGF-β, a bone morphogenetic protein, a growth differentiation factor, ADMP-1, a fibroblast growth factor, a hedgehog protein, an insulin-like growth factor, a platelet-derived growth factor, an interleukin, a colony-stimulating factor, an EGF and an activin. The at least one bioactive agent may be a bioactive peptide. The at least one bioactive agent may be a plurality of cells which may be selected from chondrocytes, osteoblasts, mesenchymal stem cells, neuronal cells, T cells, B cells, neuronal cells, liver cells, mesenchymal stem cells, adipocytes, renal cells, lung cells or a combination thereof. The method may include growing the plurality of cells ex vivo.

In another aspect, an implant for repairing a tissue defect of a subject includes a biological agent and a biocompatible carrier, wherein the shape of the implant substantially conforms to the contours of at least a portion of a tissue defect of a subject. The biological agent is for example a plurality of tissue particles such as cartilage particles. The cartilage tissue particles may be neocartilage particles, juvenile cartilage particles, cadaver cartilage particles, or may be selected from among bone tissue particles, liver tissue particles, renal tissue particles, neuronal tissue particles, muscle tissue particles, adipose tissue particles, and a combination thereof. The at least one biological agent may be a population of cells such including for example a plurality of chondrocytes, fibroblasts or tendoncytes, or a combination thereof. The population of cells may include a plurality of cells selected from among bone cells, liver cells, and kidney cells. The at least one biological agent may include a pharmaceutical compound. In one aspect the implant includes a first layer comprising the tissue particles. The implant may further include at least one bioactive agent such as a growth factor or a bioactive peptide as described elsewhere herein. The implant may further include a second layer. The second layer includes for example at least one biocompatible carrier such as a biocompatible polymer. The second layer may further include at least one bioactive agent such as a growth factor or a bioactive peptide.

The biocompatible carrier of the second layer may include a biocompatible polymer such as a biocompatible gel selected from among a starch gel, an agarose gel, a polyacrylamide gel and a combination thereof.

In another aspect, a kit for forming an implant for repairing a tissue defect includes a pliable substrate having shape memory and which can be shaped to substantially conform to the contours of at least a portion of a tissue defect thereby serving as a mold of at least the portion of the tissue defect in a subject, a biological agent and a biocompatible carrier. The biological agent is for example a plurality of tissue particles such as cartilage particles or other tissue particles as described elsewhere herein. The tissue particles may be provided in a liquid medium and the pliable substrate material having shape memory and the biocompatible carrier are all as described elsewhere herein. The kit may further include at least one perforation tool such as a scalpel, an awl, a pin, a needle or a forceps for perforating the mold to remove an amount of liquid medium after introducing liquid medium to the mold. The kit may further include at least one absorbent pad also for removing liquid medium. The kit may also further include at least one biocompatible adhesive such as a fibrin adhesive and may include at least one bioactive agent as described elsewhere herein. The kit may further an amount of calcium chloride.

BRIEF DESCRIPTION OF THE SEVERAL VIEWS OF THE DRAWINGS AND FIGURES

DETAILED DESCRIPTION OF THE INVENTION

Figure 1:
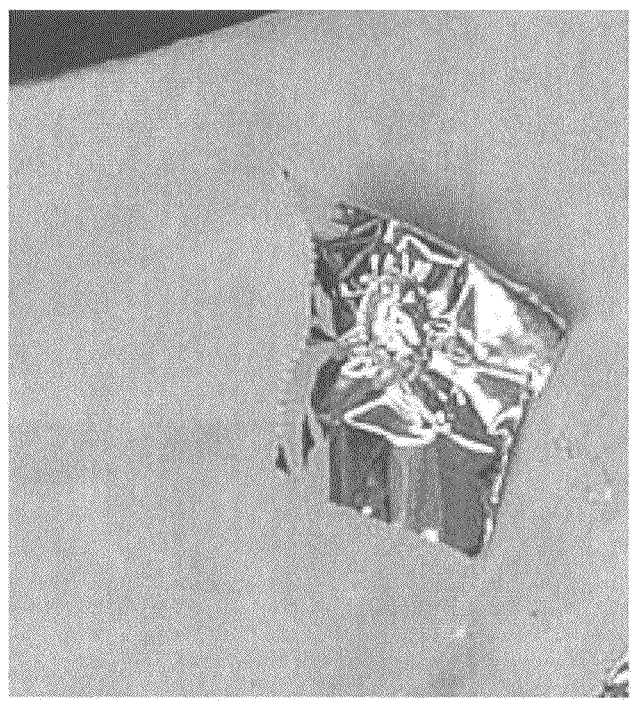
FIG. 1 illustrates an aluminum foil mold of the present teachings.

The following examples are provided for illustrative purposes only and are not to be construed as limiting the invention's scope in any manner. The description of an article, a composition, or a method in an example does not imply that the described article or composition has, or has not, been produced, or that that the described method has, or has not, been performed, regardless of verb tense. The methods and compositions described throughout this specification utilize laboratory techniques well known to skilled artisans and can be found in commonly available laboratory manuals describing for example use of biomolecules, cell culture and handling techniques, and use of antibodies.

The present inventors disclose herein molds and implants for repairing tissue defects, as well as methods of forming such molds and implants, and kits for forming and using the molds and implants.

In various embodiments of the present teachings, these methods comprise forming, on a tissue defect of a subject, a mold having a surface substantially conforming to contours of a tissue defect. In one embodiment, a tissue defect is, for example, a cartilage tissue defect such as an injury to a hyaline cartilage comprised by a subject, for example a torn knee cartilage. The tissue defect may alternatively be in any bodily tissue susceptible to repair or treatment of the defect using an implant, including musculoskeletal hard and soft tissues, oral and maxillofacial tissues, dermal tissues, and solid organ tissues. In the following detailed description, it should be understood that reference is made to cartilage tissue for illustrative purposes only and should not be taken as limiting the present mold, implant and related methods of making and using to cartilage tissue alone. It is contemplated that the present mold, implant and related methods of making and using will be comparably useful in repairing or treating other hard and soft bodily tissues.

In various configurations, a mold can be made of a pliable substrate material having shape memory, such as, without limitation, a polymer or a metal foil such as aluminum foil, a wax or other malleable material capable of retaining a particular shape The substrate material may alternatively be a liquid or fluid material such as a hydrogel or a wax in liquid phase capable of transitioning to a solid phase upon a triggering event such as exposure to a chemical agent or exposure to a change in temperature. For example, certain hydrogels are known which have a fluid phase that transitions to a solid or semi-solid phase upon exposure to a cross-linking agent. Wax in liquid phase can be disposed in the mold and then the combination cooled so that the wax resolidifies. It should be understood that in describing suitable pliable substrate materials as having shape memory, suitable substrate materials include those having the ability to adapt or conform to at the three-dimensional configuration of at least a portion of a tissue defect, and then to return to the shape conformation if briefly deformed upon removal from the defect after conforming thereto. The substrate may be a material permeable to liquid, such as liquid that may be part of a liquid storage medium for cells or tissue.

In the case of a metal foil, a medical caregiver such as a physician or surgeon can manually, with or without a surgical instrument, press the foil on to a tissue defect, such that the substrate material is substantially juxtaposed to contours of the defect (see examples below). In various configurations, a substrate material such as a foil can initially be sterile (e.g., as a result of autoclaving), and initially can be substantially flat. A foil can be of any available thickness and any convenient initial size and shape, such as, in non-limiting example, a square or rectangle of from about 5 cm to about 10 cm a side, or a circle of about 5 cm to about 10 cm diameter. In various configurations, a mold substrate such as a metal foil can have a thickness of from about 5 microns to about 200 microns; from about 10 microns to about 100 microns, from about 12 microns to about 30 microns, or from about 13 microns to about 25 microns. In some configurations, after a foil is molded to a tissue defect, the mold can have contours corresponding to those of the defect; it can further comprise walls that can aid in keeping added materials within the mold during formation of an implant.

In some aspects, a polymer such as a pliable plastic (such as a putty) can provide the substrate material for forming a mold. In these cases a medical caregiver such as a physician or surgeon can manually or otherwise mechanically using surgical instruments press the plastic on to the defect, such that the plastic is substantially juxtaposed to contours of the defect. If necessary, the material can be flattened by methods known to persons of skill in the art prior to application of the material to a tissue defect. Alternatively, an amount of a pliable solid substrate material such as a metal foil, meshed metal or plastic can initially be configured in a compact folded or pleated configuration for delivery to the site of the defect in vivo, and then mechanically expanded and applied to the defect site in order to conform thereto. For example, an amount of a pliable solid substrate material such as a metal foil may be configured in a "pleated skirt" configuration or any other folded or pleated configuration that achieves sufficient compaction of the material for it to be delivered to the defect site in vivo through limited access routes, for example using laparoscopic surgical catheters, and then expanded at the defect site so that it may be applied and conform to the defect site.

In other aspects, a curable plastic or other suitable liquid material such as a wax or a hydrogel can be applied to a tissue defect as a liquid, e.g. by flowing through a syringe. A curable plastic can be, for example, a polyurethane described in U.S. Pat. No. 6,443,988 to Felt et al., or an epoxy plastic in which a monomer is mixed with a catalyst prior to applying to applying to a tissue defect, and which polymerizes while in contact with the defect. In yet other examples, a plastic can be a bioabsorbable polymer, such as a polyester. In various configurations, a polyester can comprise a polylactic acid, a polyglycolic acid, and/or a co-polymer comprising a polylactic acid and a polyglycolic acid.

In an illustrative embodiment, following formation of the mold which has contours substantially conforming to the contours of a tissue defect, the mold is removed from the defect. Removal is accomplished manually, or otherwise mechanically with the aid of tools or surgical instruments such as forceps, or may be accomplished or assisted by exposure to a chemical or physical stimulus. For example, exposure to an increase in temperature can be used to accomplish or assist removal of a wax mold by partially melting the mold to the point that the mold is released from the implant. Alternatively, in the case of certain hydrogels, exposure to a chemical agent such as a cationic composition can break bonds between the mold and the implant. Because the mold comprises a substrate material having shape memory, if the mold is deformed during removal from the tissue defect, the mold regains the contours of the defect upon which it was formed. An implant can then be formed within the mold ex vivo.

In one embodiment, formation of the implant is accomplished by introducing into the mold a suitable biological agent such as tissue particles, cells, collagen, extracellular matrix (ECM) or tissue-engineered scaffold material. For example, the biological agent can be cartilage particles such as those described in U.S. Patent application publication 2005152882 (application Ser. No. 11/010,779 of Kizer et al., filed Dec. 13, 2004). The choice of what type of biological agent to use for forming the implant for a particular application may take into account, for example, whether a need exists for a longer shelf-life for the implant once formed. Use of tissue-engineered scaffold for forming the implant may be especially well-suited for applications where it is anticipated that the implant will remain in storage for a period of time. The scaffolding may later be populated with cells just before or at about the time the implant is being prepared for actual implantation.

In various embodiments, tissue particles or other biological agents or both are added to the mold along with liquid medium in which the particles or other agents are carried or suspended and maintained. Excess liquid medium can then be removed from the mold by aspiration, or, in some configurations, by piercing the mold to introduce one or more apertures so that the liquid can drain, or by a combination of aspiration and piercing. In various configurations, perforations can be introduced to the mold using any sharp tool or implement, such as, without limitation, a scalpel, a forceps, a needle, a pin or an awl. In other embodiments, the mold is formed of a substrate material that is perforated or is a mesh material that does not require additional piercing or perforation for draining excess liquid medium. Alternatively, the mold is formed of a substrate material that is otherwise permeable to liquid, such as a porous or semi-porous membrane, so that when tissue particles or cells in a liquid storage medium are introduced to the mold, excess liquid medium drains through the material without the need for perforations.

In some aspects, draining of liquid through perforations or mesh material can be promoted by contacting the mold with an absorbent body, such as, without limitation, a surgical sponge, paper towel, gauze or pad.

In other aspects, the tissue particles or other biological agent for forming the implant may be disposed in the mold without excess liquid medium. For example, excess liquid medium may be removed from tissue particles or other biological agent prior to disposing in the mold. Alternatively, the tissue particles or other biological agent may not have required combination with excess liquid medium in the first instance in order to be suitable for disposition in the mold. In either case, it will be appreciated that while excess liquid medium may assist in achieving a more uniform distribution of the tissue particles or other biological agent in the mold, excess liquid is not necessarily required for the distribution to be sufficient for formation of the implant. In particular, in certain cases autologous tissue that has been removed from the subject may be especially suitable for forming the implant, and such tissue may exist in a form such as a tissue core or plug reasonably well-suited to being disposed in the mold without the need to add liquid medium. In various embodiments, a biocompatible carrier is added to the mold. The carrier is added to the mold before, during or after adding the biological agent such as tissue particles, cells, collagen, ECM or a tissue-engineered scaffold. In various configurations, a carrier can be added to a mold as a liquid. Such a carrier can embed the one or more tissue particles, and can also form a solid. In various aspects, a liquid carrier can fill space within the mold and therefore can have a shape substantially conforming to the contours of the mold. Because the mold has a shape substantially conforming to the contours of the defect, the carrier can have a shape substantially conforming to contours of the tissue defect. In various aspects, a carrier can be a biological adhesive such as a fibrin glue. As used herein, "fibrin" and "fibrin glue" include fibrin generators such as mixtures of fibrinogen and thrombin (Gibble, J W and Ness, P M, Transfusion 30: 741-747, 1990; Alston, S M et al., Translational Research 149: 187-195, 2007). In non-limiting example, a fibrin glue can be a commercially available fibrin glue such as Tisseel® VH fibrin sealant (Baxter Healthcare Corporation, Westlake Village, Calif.), which can be prepared for use according to manufacturer's instructions. In other configurations, a biocompatible carrier can comprise at least one biocompatible polymer, such as, without limitation, a fibrinogen, a thrombin, a fibrin, a type I collagen, a type II collagen, a type III collagen, a gelatin, a fibronectin, a laminin, a hyaluronic acid, a hydrogel, a pegylated hydrogel, a chitosan or a combination thereof. In addition, in some aspects, a biocompatible polymer can be autologous to the intended recipient of an implant, and can be, without limitation, an autologous plasma protein such as autologous thrombin, autologous fibrinogen, autologous fibrin and/or autologous fibronectin. In addition or alternatively, in various configurations, a biocompatible carrier can comprise a biocompatible gel, which can be, without limitation, a starch gel, an agarose gel, a polyacrylamide gel or a combination thereof. In various configurations, a biological agent such as tissue particles within a mold can be arranged such that the particles are distributed substantially uniformly within the mold. In various configurations, instruments and tools such as forceps and needles can be used to arrange the particles. In some configurations, the particles and the carrier can together comprise a first layer, within which the particles can be distributed substantially uniformly. In various aspects, the carrier can congeal, thereby forming an implant having contours substantially corresponding to those of the mold and hence to a tissue defect. In various aspects, the distributing can be effected before or after removal of the liquid, or after addition of a biocompatible carrier (see below). In some aspects, combining a biological agent such as tissue particle and a biocompatible carrier such as a fibrin glue can form a composite. Thus, an implant or a first layer thereof can comprise particles which are immobilized and distributed substantially uniformly throughout a biocompatible carrier.

In various configurations, a second or additional layer can be formed in a mold. Such a layer can be added adjacent to a first layer, for example, by adding a layer of fibrin glue over a previously formed layer comprising fibrin glue and tissue particles. A second or additional layer can comprise components which are the same or different from those of the first layer. In various aspects, a second or additional layer can comprise at least one biocompatible carrier. In various aspects, a second layer can also comprise one or more bioactive agents such as one or more growth factors, one or more bioactive peptides, and/or cell populations. In various aspects, a second layer can comprise a biocompatible gel, and/or tissue particles such as cartilage tissue particles.

Because an implant will also retain its shape after it is formed, the implant and the mold can be separated in various aspects. Separation can be effected using methods well known to skilled artisans and will depend in part on the material used for the mold. For example, one or more slits can be made in a mold with a scalpel, and pieces of the mold can be pulled away from the implant with the aid of forceps. In some aspects, such as with a mold made of pre-perforated material, the mold may be torn or peeled away from the implant with or without the aid of a surgical instrument. In the case of a mold made of a wax for example, the mold may be melted for removal. In other aspects, certain mold materials such as for example hydrogels may be readily susceptible to being dissolved away using a chemical agent. It is further contemplated that other physical methods and tools such as those involving laser or electrocautery may be sued to remove the mold from the implant.

In some aspects, an implant can be flexible yet resilient to deformation, so that it can return substantially to its original shape following a deformation, for example after passaging through a hollow needle. Following separation of an implant from a mold, the implant can be applied to the tissue defect. In various aspects of the methods described herein, applying an implant to a tissue defect such as a cartilage defect can comprise inserting the implant at the tissue defect. In some aspects, a method can further include affixing the implant to the tissue defect. In some aspects, affixing an implant can include securing the implant to the tissue defect using methods and materials well known to skilled artisans such as, for example, biocompatible glues, sutures, staples, or pins. In non-limiting example, a biological glue can be used to affix an implant to a tissue defect after the contours of the implant are apposed to the corresponding contours of the defect.

In some alterative aspects, a mold can comprise a bioabsorbable substrate material such as a polyester. Moreover, it is envisioned that a mold formed at the site of a defect in vivo may also be withdrawn from the defect site, for example through a hollow needle, and upon returning substantially to its original shape following deformation, is then used ex vivo for formation of the implant. The mold and implant are then together introduced to the defect site through the hollow needle and together applied to the defect site. In such cases, a combination of mold and implant can be applied to a tissue defect without separating the mold from the implant. In aspects in which an implant is deformable, an implant can be administered to a subject by injecting the implant into the subject at the site of the tissue defect using a syringe and a hypodermic needle. In aspects in which a combination of a mold and implant is inserted at a tissue defect, the mold can be separated from the implant by standard surgical procedures known to skilled artisans, such as, without limitation, slicing of the mold followed by removal of the mold from the defect.

In various methods of the present teachings, tissue particles can be initially carried or suspended in a liquid medium. Such a liquid medium is, in various aspects, a cell, tissue or organ storage medium, such as, without limitation, a medium disclosed in U.S. Patent application publication 2005152882 (the disclosure of which is herein incorporated by reference in its entirety), for example Dulbecco's Modified Eagle's Medium (DMEM) or Roswell Park Memorial Institute Medium (RPMI).

In some configurations, an implant and/or a mold of the present teachings can further comprise at least one bioactive agent, such as, without limitation, a hormone, a growth factor, a pharmaceutical compound, a bioactive peptide, a nucleotide such as an RNAi molecule, a vector, a plurality of cells, and the like. The bioactive agent can be a constituent of any layer of an implant. A growth factor can be, without limitation, a TGF-β, a bone morphogenetic protein, a growth differentiation factor, ADMP-1, a fibroblast growth factor, a hedgehog protein, an insulin-like growth factor, a platelet-derived growth factor, an interleukin, a colony-stimulating factor, an EGF or an activin. A pharmaceutical compound can be, without limitation, an analgesic, an anesthetic such as a local anesthetic, or a cyclooxygenase inhibitor. A bioactive peptide can be, without limitation, neuropeptide Y, secretin, cholecystokinin, or a cell-penetrating peptide such as penetratin, substance P or R9 or for example any bioactive peptide with antimicrobial activity. In some aspects, a bioactive agent can comprise a plurality of cells. Such cells can be, without limitation, chondrocytes, osteoblasts, mesenchymal stem cells, neuronal cells, T cells, B cells, neuronal cells, liver cells, mesenchymal stem cells, adipocytes, renal cells, lung cells and combinations thereof. In some aspects, the cells can be autologous to an intended recipient of an implant, and can be obtained directly from the intended recipient or grown in vitro prior to adding to an implant. In some aspects, the bioactive agent may comprise a nucleotide. A nucleotide can be a naturally occurring sequence of DNA or RNA, synthetic DNA or RNA, or chemically modified DNA or RNA, such as chemically modified otherwise naturally occurring RNAi molecules. In some aspects, the bioactive agent may comprise a vector, for example for introducing a genetic sequence to the implant. A vector can be for example a viral vector.

In various embodiments of the present teachings, a subject can be a mammal, which can be a human or a non-human mammal. In some configurations, a human subject can be a human in need of treatment of a tissue defect, such as a cartilage defect. In some configurations, a human subject can have a degenerate or damaged cartilage such as a hyaline cartilage comprised by a joint.

In various aspects of the present teachings, a mold and an implant formed therein can be three dimensional, such as when its shape corresponds to the contours of a tissue defect. Thus, the present teachings provide implants which are not limited to two-dimensional structures, such as films or laminates. In other aspects, a mold and implant formed therein can be substantially cylindrical in shape, such as, without limitation, when a tissue defect such as a cartilage defect is prepared by a surgeon to include a substantially cylindrical aperture. In these configurations, a caregiver such as a surgeon can, prior to forming a mold, prepare a tissue defect such as a cartilage defect for receiving an implant by removing tissue from the defect, such that a circular or cylindrical defect remains. Hence, in some configurations, the methods can include preparing a tissue defect for receiving an implant. The preparation can comprise modifying the defect to comprise a substantially cylindrical aperture. However, it will be noted that an advantage of the present mold, implant and related methods and kits is the ability to adapt the shape of the mold and ultimately the shape of the implant to any shape that helps repair the defect while also preserving the greatest amount of healthy tissue. The site-specific mold and implant can avoid the need to remove healthy tissue to adapt the shape of the defect to a particular predetermined shape of the implant. In addition, the present mold, implant, related methods and kits are well-suited for use in a "tiling" approach using multiple implants at a defect site.

In some embodiments of the present teachings disclosing implants comprising a mixture of at least one biological agent and a biocompatible carrier, as well as methods for forming such implants, a biological agent can comprise a plurality of tissue particles, such as cartilage particles. In other aspects, a biological agent can comprise a population of cells. A population of cells of these embodiments can comprise, without limitation, a population of chondrocytes, a population of fibroblasts, a population of tendoncytes, a population of bone cells such as osteoblasts, a population of kidney cells, a population of lymphocytes such as T lymphocytes or B lymphocytes, a population of hepatocytes, and/or a population of stem cells such as mesenchymal stem cells or embryonic stem cells, or a combination of any such cell populations. In various configurations, the inserting and the affixing of an implant to a tissue defect can be accomplished using methods well known to skilled artisans, such as inserting the implant using a minimally invasive surgical technique (MIS), such as arthroscopically. An MIS, for example, includes a mini-open arthrotomy with minimal disruption of the surrounding joint structure, typically involving a smaller incision than incisions required in regular open cartilage repair surgeries. In other aspects, the present mold, implant and related methods of forming and using same contemplate their application in situations involving defects to bone tissue underlying all or a portion of the tissue defect, for example the cartilage tissue defect. For example, alternative materials such as engineered bone tissue and/or trabecular metal may be used to reconstruct a bone tissue defect underlying a cartilage tissue defect.

FIG. 1 is a flow diagram illustrating the steps in a method 100 for repairing tissue defects according to the present teachings. By using an in vivo molding approach to determine the shape and dimensions of the implant, the method provides implants that are very well fit to the specific tissue defect. In a first step 101, a surgeon, technician or other individual trained in orthopedic surgical techniques, applies the substrate material having shape memory, to all or a portion of the tissue defect to be repaired. The tissue defect is, for example, a cartilage tear in a major joint such as the knee. Thus the mold is prepared in vivo in the subject having the tissue defect. The process of applying the substrate material to all or a portion of the tissue defect, for example by manually pressing with or without aid of a surgical instrument, conforms 102 the substrate material to the contours of the tissue defect or portion thereof.

Depending on the substrate material being used, a wait period (not itemized in FIG. 1) may be required in order to allow the substrate material to undergo processes necessary for the material to retain the contours of the tissue defect or portion thereof to which the substrate material has been applied. For example, if the substrate material is a curable plastic or polymerizing plastic, typically a period of time that varies with the type of plastic used should elapse before the material attains properties sufficient to retain the geometry of the tissue defect. Commercially available epoxies and other curable or polymerizing plastics for such purposes are well known and should be used according to manufacturer's instructions for the process of curing or polymerizing. If the substrate material being used is a metal foil, the foil immediately retains the geometry of the tissue defect to which it has been firmly applied. In any case, once the individual preparing the mold ascertains that the substrate material has attained sufficient shape memory of the tissue defect or portion thereof, the individual removes 103 the mold from the tissue defect, typically by simply using gloved fingers or with a sterile surgical instrument. The implant will be formed ex vivo using the mold formed in vivo.

To form the implant 104, at least a first layer of implant material is placed 105 into the mold. The implant material includes at least a biological agent such as tissue particles. The tissue particles, e.g. cartilage particles, may be further maintained in a liquid medium as described elsewhere herein. The liquid medium can facilitate delivery of the tissue particles into the mold. If a liquid medium is used, it is removed from the mold by aspiration, or by piercing or perforating the mold to drain the liquid after the tissue particles are placed in the mold. In one embodiment, the substrate material is perforated to start with, or is a mesh type material sufficient to initially receive an implant material including a liquid constituent, and then to allow the liquid constituent to drain from the mold after a short period of time during which the implant material is distributed within the mold. In another illustrative embodiment, a biocompatible carrier is also added to the mold to form a first layer of the implant. It should be noted however that the biocompatible carrier may be added to the mold before, during or after placing the tissue particles in the mold. For example, in one aspect fibrin can be combined directly with cartilage tissue particles with or without medium. In alternative embodiments, forming the mold may also include adding a bioactive agent or agents to the mold, thereby forming another layer of the implant, or as part of the first layer. As described elsewhere herein, adding a bioactive agent or agents may include adding growth factors or hormones, pharmaceutical compounds, bioactive peptides, nucleotides, vectors, or other cells.

Referring again to FIG. 1, ultimately the implant is separated from the mold 106, and the implant is applied 107 to the tissue defect or portion thereof to which the implant now conforms. It should be noted that the implant may be applied to the tissue defect together with the mold first, and the mold then separated from the implant after implantation, or the mold may be removed from the implant before the implant is applied to the tissue defect. In either case, the implant comprising at least the tissue particles and a biocompatible carrier, is made contour-specific for the particular tissue defect and therefore very well fit to the tissue defect. It is believed that the high fit specificity of the implant improves recovery speed and outcomes.

In another aspect, the present teachings encompass a kit for forming the aforementioned mold and implant for repairing a tissue defect. The mold materials and implant materials may be advantageously provided in kit form including separately packaged amounts of each type of material. In a kit the amounts of each material can be for example amounts sufficient for the treatment or repair of a defect of a predetermined size. In one aspect, a kit includes an amount of the pliable substrate for forming the mold as described herein, and the biological agent such as a plurality of cells or tissue particles. In another aspect, the kit may further comprise an amount of the biocompatible carrier. Alternatively, a kit can include an amount of the pliable substrate and an amount of the carrier, with the biological agent such as tissue particles or cells to be provided from another source. In an exemplary embodiment of a kit, each component of the kit is packaged separately in sterile packaging or in packaging susceptible to sterilization. The biological agent such as cells or tissue particles may be in a container such as a glass or plastic vial and may further be carried or suspended in a liquid storage medium suitable for maintaining cells, tissues or organs. In any kits containing cells or tissue particles in liquid storage medium, the kits may further include an absorbent material in the form for example of a pad or wipe for absorbing excess liquid medium from the mold after the biological agent has been introduced to the mold. The pliable substrate can be wrapped or sealed separately in a paper or plastic wrapper, sterilized blister pack or the like. The biocompatible carrier, for example fibrin, can also be contained in a separate glass or plastic vial or other compact container. The kit may optionally further include one or more syringes or other delivery device(s) for introducing the implant material and carrier to the mold. Kits may optionally further include one or more additional containers each storing a bioactive agent such as growth factor or a pharmaceutical agent that may be added to the implant. The kit further includes, for example, printed instructions for forming the mold and the implant and for using the implant to repair a tissue defect. All elements of the kit are provided together in suitable amounts in a box or other suitable packaging.

EXAMPLES

The following examples are provided for illustrative purposes only and are not to be construed as limiting of claim scope. The description of an article, a composition, or a method in an example does not imply that the described article or composition has, or has not, been produced, or that that the described method has, or has not, been performed, regardless of verb tense. The methods and compositions described throughout this specification utilize laboratory techniques well known to skilled artisans such as can be found in routinely available laboratory manuals.

Example 1

This example illustrates formation of a mold.

In this example, a sterile piece of aluminum foil having sufficient moldability and rigidity (shape memory) is applied by physician to a cartilage injury. In this case, the physician uses her fingers or a surgical instrument such as a spatula to press the aluminum foil into the cartilage defect so that the foil is in extensive contact with the base and side walls of the defect. This shaping results in a mold which can be used to form an implant which matches the size and shape of the defect (FIG. 1).

Example 2

This example illustrates formation of an implant of the present teachings using a mold.

Figure 2:
FIG. 2 illustrates formation of an implant in a mold of the present teachings.

In this example, a syringe is used to transfer cartilage tissue fragments and storage medium to the base of an aluminum foil mold of a cartilage defect, such as the mold illustrated in Example 1. Excess fluid is removed by aspiration, and also by introducing holes in the base of the mold using a scalpel. The mold is contacted with an absorbent sterile pad to absorb liquid through the holes. However, enough fluid remains so that the particulate tissue pieces are not clumped together (FIG. 2). The pieces distribute evenly across the surface of the base of the foil mold. A layer of fibrin is then gently added to embed the cartilage particles within the mold. More fibrin is then overlaid on the first layer to increase the thickness of the implant. The skirt of the foil mold is then gently pulled to straighten the foil, or pulled or peeled away using a surgical instrument such as a forceps This action releases the implant from the foil mold, which is now available for implantation at a cartilage defect.

Example 3

This example illustrates formation of an implant in an alternative aspect of the present teachings.

Example 2 above describes formation of a implant using a multiple step process including first the introduction of cartilage tissue fragments to the mold followed by introduction of fibrin to the mold. In this example, an implant is formed in a "single-step" process. Cartilage tissue fragments are combined with fibrin and the combination is introduced to the mold, also using a syringe. A pharmaceutical agent such as a growth factor is optionally added to the combination before introducing the combination the mold. This approach is well-suited for carrier materials that have a well-defined and predictable setting time.

Example 4

This example illustrates transfer of an implant to a tissue defect.

Figure 3:
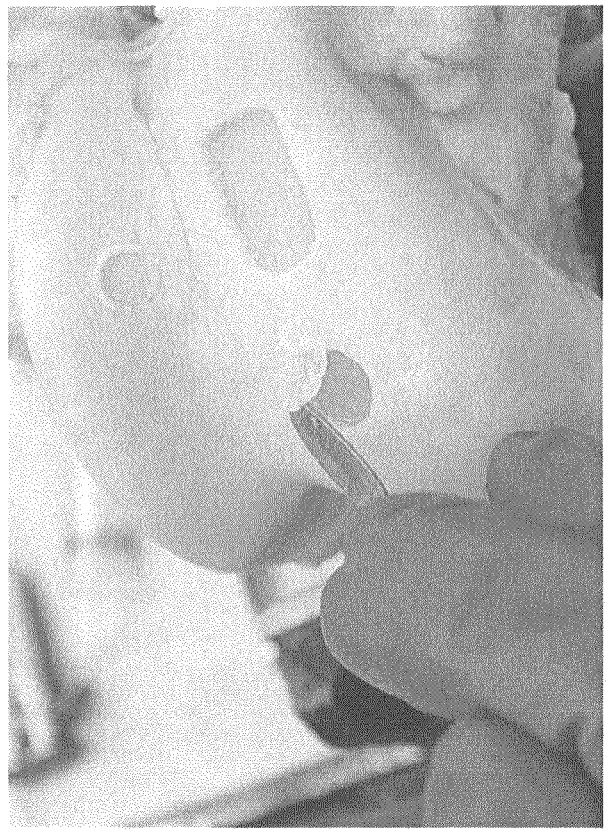
FIG. 3 illustrates application of an implant of the present teachings to a cartilage defect.
Figure 4:
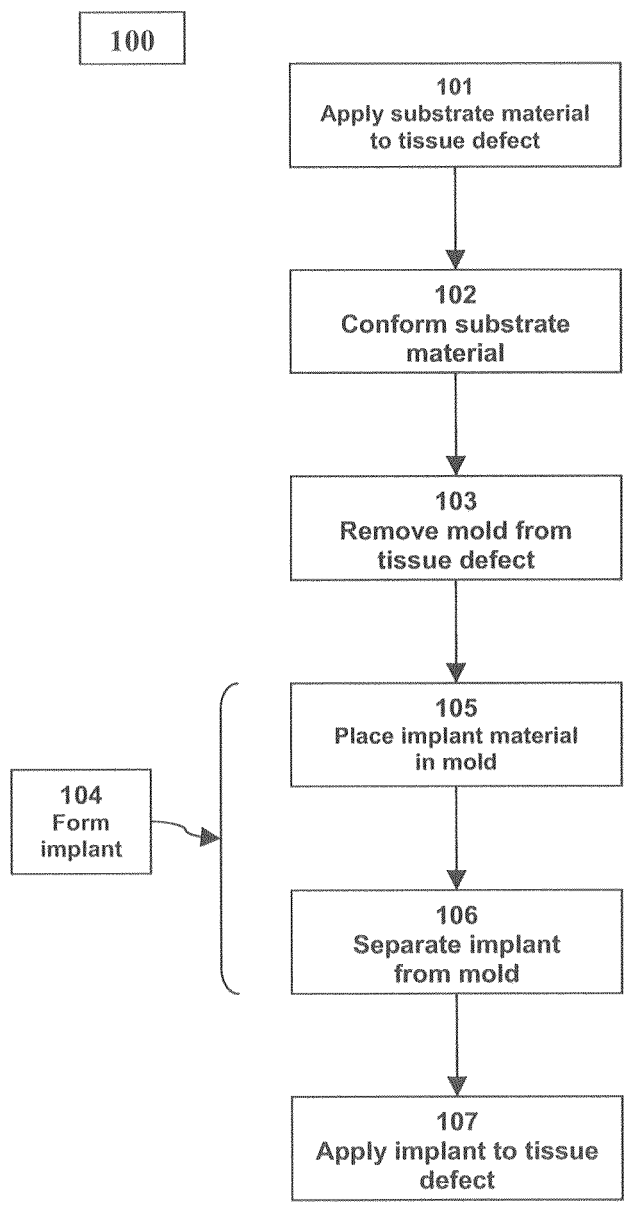
FIG. 4 is a flow diagram illustrating a method for repairing tissue defects according to the present teachings.

In this example, a cartilage defect in a cadaver is exposed. A fibrin adhesive is applied to the base of the cartilage defect, and the implant of Example 2 is gently lifted with a spatula and placed into the defect such that contours of the defect and the implant correspond (FIG. 3). The implant is then gently pressed against the defect and pulled with forceps so that the implant fits snugly in the defect. Optionally, more fibrin is then added around and over the implant to fill the defect to the extent needed.

Example 5

This example illustrates transfer of an implant to a tissue defect.

In this example, a cartilage defect in a cadaver is exposed. A fibrin adhesive is applied directly to the intended contact surface of the implant of Example 2, and the implant of is gently lifted with a spatula and placed into the defect such that contours of the defect and the implant bearing the previously applied layer of fibrin adhesive correspond. The implant is then gently pressed against the defect and pulled with forceps so that the implant fits in the defect. More fibrin is optionally then added around and over the implant to fill the defect as may be needed.

Example 6

This example illustrates a protocol for treating a cartilage defect.

In this example, an autologous fibrin adhesive is prepared at least one week in advance of surgery. Alternatively, a commercially prepared fibrin as obtained off the shelf. A medial or lateral parapatellar mini-arthrotomy is performed using a tourniquet (which need not be inflated). The defect area is marked with a sterile surgical marker. The cartilage tissue is removed within the defect area with a curette, thereby creating a well-defined vertical defect perimeter. The defect base is then cleared to remove the calcified cartilage layer, taking care to avoid violating the subchondral cortical bone plate. If subchondral bone bleeding occurs, it must be stopped before implantation of an implant of the present teachings. The defect and surrounding tissue are irrigated frequently with normal saline during the surgery.

Sub-chondral bleeding: methods for controlling and stopping subchondral bleeding include: a) use of neuro-patties soaked with a dilute 1:1000 epinephrine and sterile saline solution; b) direct application of thrombin to the site of bleeding; c) electrocautery using a needle-tipped electrocautery device to cauterize only the bleeding points, not the entire base of the defect. Electrocautery can be used, particularly if bleeding is especially difficult to control, for example in a patient who had previous marrow stimulation.

Defect sizing: with the aid of a sterile flat-ended rod, a sterile thin foil is pressed into the defect so that the outer shape of the foil fits snugly into the defect base and vertical wall. The approximate surface area of the defect is measured to determine the approximate amount of cartilage particles needed. If DeNovo® NT particles (Isto Technologies, Inc., St. Louis, Mo. and Zimmer, Inc., Warsaw, Ind.) are used, one pack of particles is needed for each about 0.5 to about 3.0 cm$^2$ defect or for an average of about 2.5 cm$^2$ defect. The foil mold is removed from the defect and placed on sterile gauze or a sterile absorbent plant. The defect may be documented photographically, including a ruler showing two dimensions at 90 degrees to each other.

Implant Preparation: A clear sterile piece of plastic tubing, at least 30 mm in length, is attached to a sterile syringe with a luer tip orifice of <1 mm. The lid of a package of DeNovo® NT particles is opened, and the cartilage tissue particles and medium are aspirated using the syringe. The cartilage particles will be contained within the tubing, while the storage medium will be aspirated into the syringe barrel. The cartilage and the storage medium are transferred to the foil old. Excess storage medium is aspirated by aspiration until only a shallow pool of the medium remains. This is done so that the cartilage pieces are not clumped together. The tissue pieces are then distributed evenly across the surface base of the foil mold with the tip of the syringe. Remaining liquid is removed by aspiration while avoiding further movement of the cartilage pieces. A sharp tip tool such as a scalpel is also used to make small perforations in the foil at various locations to allow excess liquid to be absorbed by an absorbent sterile gauze or pad underlying the foil mold. A layer of fibrin glue is then gently applied to embed the particulate tissue pieces. More fibrin is then applied, such that the tissue/fibrin composite fills to about ¾ the depth of the mold. The fibrin is then set for 5-10 minutes in accordance with fibrin preparation instructions. The edges of the foil mold are then gently pulled to straighten the foil so that the tissue/fibrin implant separates from the vertical walls of the foil mold. The implant can then be lifted from the mold base using a sterile flat instrument such as a spatula. The implant is now ready for implantation.

Alternatively, the implant is prepared using the single-step process in which the fibrin is added directly to the cartilage particles in the syringe tubing by aspirating the fibrin after any excess storage medium is aspirated. The fibrin may otherwise be added directly to the cartilage particles and medium in the tubing and syringe in the case where no excess storage medium is aspirated. In either case, the cartilage tissue particles together with the fibrin may be gently agitated using the action of the syringe plunger within the syringe barrel to promote gentle mixing of the fibrin with the cells and any remaining medium. The mixture of cartilage particles, fibrin and any remaining medium is then introduced across the surface base of the foil mold with the tip of the syringe. Remaining steps for removal and use of the implant thus formed are as described above.

Fixation of an implant into a cartilage defect: Initially, the defect area and the implant are gently dried using sterile surgical gauze. A very thin layer of fibrin glue, approx. 0.01-0.1 ml to cover then entire base of the defect. The implant is then placed on the defect, ensuring a matched fit between the contours of the defect and those of the implant. The implant is then gently held in close contact with the base and edges of the defects (e.g., using a finger). The implant should be recessed by approximately 0.5 mm relative to surrounding native cartilage. The implant is held against the defect and gently stretched (using instruments such as a pair of surgical forceps) so that the implant fits snugly to the defect wall. The fibrin is allowed to cure for at least 5 minutes, and care must be taken not to manipulate or dislodge the implant during the curing. The transfer of the implant to the defect can be documented photographically.

Wound closure: Based upon the physician's judgment and standard of care, drains can be inserted within the wound site. The joint capsule, fascial layers and skin can be closed using standard suture and surgical techniques.

It is to be understood that the specific embodiments of the present teachings as set forth herein are not intended as being exhaustive or limiting, and that many alternatives, modifications, and variations will be apparent to those of ordinary skill in the art in light of the foregoing examples and detailed description. Accordingly, the present teachings are intended to embrace all such alternatives, modifications, and variations that fall within the spirit and scope of the following claims.

All publications, patents, patent applications and other references cited in this application are herein incorporated by reference in their entirety as if each individual publication, patent, patent application or other reference were specifically and individually indicated to be incorporated by reference.

What is claimed is:

1. An apparatus for forming a cartilage implant, comprising:
   a pliable metal foil substrate shapeable to substantially conform to one or more contours of a cartilage defect and having a releasable surface, the one or more contours forming a substrate cavity at least partially surrounded by the releasable surface; and
   a biocompatible carrier disposed in the substrate cavity and having an outer portion in contact with the releasable surface, the carrier comprising human juvenile cartilage particles including viable chondrocytes for combining with the biocompatible carrier, the biocompatible carrier, when cured, removable from the substrate and defining a size and shape complementing a size and shape of the substrate cavity.

2. The apparatus of claim 1, wherein the pliable substrate serves as a mold of at least a portion of the cartilage defect.

3. The apparatus of claim 2, wherein the mold has one or more perforations there through.

4. The apparatus of claim 1, wherein the pliable metal foil substrate comprises aluminum.

5. The apparatus of claim 1, wherein the pliable metal foil substrate is sterile.

6. The apparatus of claim 1, wherein the cartilage particles are obtained from a cadaver.

7. The apparatus of claim 6, wherein the cartilage particles are allogenic to a recipient thereof.

8. The apparatus of claim 1, wherein the cartilage particles are derived from cartilage generated in vitro from human juvenile chondrocytes.

9. The apparatus of claim 1, wherein the cartilage particles are articular cartilage.

10. The apparatus of claim 1, wherein the cartilage particles have a dimension from about one to about three millimeters.

11. The apparatus of claim 1, wherein the cartilage particles range in size from about 1 to about 27 mm$^3$.

12. The apparatus of claim 1, wherein the cartilage particles are from donors less than fifteen years of age.

13. The apparatus of claim 12, wherein the cartilage particles are from donors less than two years of age.

14. The apparatus of claim 12, wherein the cartilage particles are from donors from about 20 weeks to about 13 years of age.

15. The apparatus of claim 1, wherein the cartilage particles are disposed in a liquid medium.

16. The apparatus of claim 15, wherein the liquid medium is a cell, tissue or organ storage medium.

17. The apparatus of claim 1, wherein the biocompatible carrier comprises at least one biocompatible adhesive.

18. The apparatus of claim 17, wherein the biocompatible adhesive comprises a fibrin.

19. The apparatus of claim 1, wherein the implant further comprises at least one bioactive agent.

20. The apparatus of claim 19, wherein the at least one bioactive agent is a growth factor thereof.

* * * * *